United States Patent
Fu et al.

(10) Patent No.: US 11,608,319 B2
(45) Date of Patent: Mar. 21, 2023

(54) BETA-AMINO ACID DERIVATIVE, KINASE INHIBITOR AND PHARMACEUTICAL COMPOSITION CONTAINING THE SAME, AND METHOD FOR PERFORMING AN IN VIVO RELATED APPLICATION THAT BENEFITS FROM THE INHIBITION OF A KINASE

(71) Applicant: Industrial Technology Research Institute, Hsinchu (TW)

(72) Inventors: Chih-Wei Fu, Taoyuan (TW); Chih-Peng Liu, Hsinchu (TW); Yi-Hsun Chen, Hsinchu (TW); Chia-Mu Tu, Taipei (TW); Chiu-Lien Hung, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 17/117,615

(22) Filed: Dec. 10, 2020

(65) Prior Publication Data
US 2022/0363645 A1    Nov. 17, 2022

Related U.S. Application Data

(60) Provisional application No. 62/955,683, filed on Dec. 31, 2019.

(51) Int. Cl.
| | | |
|---|---|---|
| *C07D 231/12* | (2006.01) | |
| *C07D 403/12* | (2006.01) | |
| *A61P 27/06* | (2006.01) | |

(52) U.S. Cl.
CPC ............ *C07D 231/12* (2013.01); *A61P 27/06* (2018.01); *C07D 403/12* (2013.01)

(58) Field of Classification Search
CPC ............................ C07D 231/12; C07D 403/12
See application file for complete search history.

(56) References Cited

U.S. PATENT DOCUMENTS

| | | |
|---|---|---|
| 8,504,218 B2 | 8/2013 | Mollet et al. |
| 10,201,520 B2 | 2/2019 | Kambe et al. |
| 10,392,402 B2 | 8/2019 | Wang et al. |
| 2012/0135984 A1 | 5/2012 | Delong et al. |

FOREIGN PATENT DOCUMENTS

| | | |
|---|---|---|
| TW | I643619 B | 12/2018 |
| WO | WO 2010/036316 A1 | 4/2010 |
| WO | WO 2014/134391 A1 | 9/2014 |
| WO | WO 2018/094362 A1 | 5/2018 |

OTHER PUBLICATIONS

Registry No. 1787595-11-2, entered in STN on Jun. 24, 2015; Retrieved from Chemical Library; Supplier: Aurora Fine Chemicals.*
Registry No. 1787986-75-7, entered in STN on Jun. 24, 2015; Retrieved from Chemical Library; Supplier: Aurora Fine Chemicals.*

(Continued)

*Primary Examiner* — Shawquia Jackson
(74) *Attorney, Agent, or Firm* — Birch, Stewart, Kolasch & Birch, LLP

(57) ABSTRACT

A compound represented by Formula (I), a pharmaceutically acceptable salt or ester, hydrate, solvate or crystalline form thereof is provided:

Formula (I)

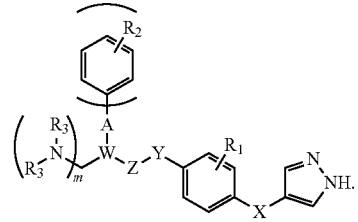

The compound represented by Formula (I) is a β-amino acid derivative, and in Formula (I) X is a single bond or O; Y is NH or C=O; Z is C=O, C=S, NH,

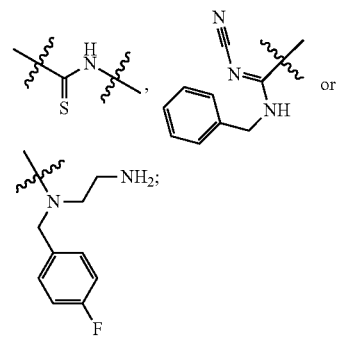

W is C or N; A is a single bond, O, OH, OCH$_2$, a heterocycle or N$_3$; R$_1$ is H or F; R$_2$ is H, F, OH, CF$_3$, CH$_2$OH, CHO or

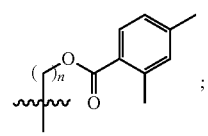

R$_3$ is H; n is 0 or 1; and m is 0 or 1.

17 Claims, 9 Drawing Sheets
(3 of 9 Drawing Sheet(s) Filed in Color)

(56) References Cited

OTHER PUBLICATIONS

Registry No. 1506916-17-1, entered in STN on Dec. 30, 2013; Retrieved from Chemical Library; Supplier: Aurora Fine Chemicals.*

Glaucoma [online], retrieved from the internet on Jan. 10, 2022. URL https://www.nei.nih.gov/learn-about-eye-health/eye-conditions-and-diseases/glaucoma.*

No new references.*

Borghi, V., et al. "A Novel Nitric Oxide Releasing Prostaglandin Analog, NCX 125, Reduces Intraocular Pressure in Rabbit, Dog, and Primate Models of Glaucoma," J. Ocul. Pharmacol. Ther., 2010, vol. 26, No. 2, pp. 125-131.

Feng, Y., et al, "Discovery of Substituted 4-(Pyrazol-4-y1)-phenylbenzodioxane-2-carboxamides as Potent and Highly Selective Rho Kinase (ROCK-II) Inhibitors," J. Med. Chem., 2008, vol. 51, pp. 6642-6645.

Yin. Y., et al, "Synthesis and Biological Evaluation of Urea Derivatives as Highly Potent and Selective Rho Kinase Inhibitors," J. Med. Chem., 2013, vol. 56, pp. 3568-3581.

Anonymous. "RHOPRESSA (netarsudil ophthalmic solution) Label, NDA 208254,Reference ID:4194833" Dec. 1, 2017.

Taiwan Office Action issued in corresponding Taiwan Application No. 109143679, dated Oct. 8, 2021.

The Extended European Search Report (ESSR) issued in corresponding European application No. 20213242.9, dated Apr. 16, 2021.

\* cited by examiner 0.1% Compound 20

0.02% AR-13324

1 hour    4 hours    6 hours    8 hours

BETA-AMINO ACID DERIVATIVE, KINASE INHIBITOR AND PHARMACEUTICAL COMPOSITION CONTAINING THE SAME, AND METHOD FOR PERFORMING AN IN VIVO RELATED APPLICATION THAT BENEFITS FROM THE INHIBITION OF A KINASE

CROSS REFERENCE TO RELATED APPLICATION

This application claims priority to U.S. Provisional Application Ser. No. 62/955,683, filed on Dec. 31, 2019, the entirety of which is incorporated by reference herein.

TECHNICAL FIELD

The present disclosure relates to a novel compound, and particularly to a novel β-amino acid derivative, kinase inhibitor and pharmaceutical composition containing the same, and uses thereof.

BACKGROUND

In order to keep the eyeball in a certain shape to maintain the optical function and metabolism of the eye, the ciliary body will secrete aqueous humor to perform this work. When the drainage route of aqueous humor is blocked and aqueous humor accumulates, an increase in intraocular pressure will be the result, which is the biggest risk factor for glaucoma.

At present, it is known that aqueous humor drainage mainly occurs in the following three ways: (1) Schlemm's canal pathway (major, conventional pathway); (2) Uvea-sclera pathway (small amount), about 10%-20%; and (3) Absorption on the surface of the iris (minor amount). The mechanisms of reducing intraocular pressure of commonly used glaucoma drugs are: (a) reducing the production of aqueous humor, such as β-receptor blockers, carbonic anhydrase inhibitors, and α-receptor agonists; and (b) increasing the drainage of aqueous humor (Uveoscleral pathway), such as prostaglandin analogs, alpha receptor agonists, etc.

The Rho/ROCK pathway plays an important role in the regulation of the cytoskeleton. Rho/ROCK inhibitors can regulate the functions of the actin cytoskeleton, extracellular matrix and Schlemm's tube endothelial cells in the trabecular meshwork tissue, thereby reducing the intraocular pressure.

Currently, some pharmaceutical companies have begun to explore the impact of ROCK inhibitors on reducing intraocular pressure in humans, and have successively developed new drugs. After evaluating the clinical safety and effectiveness for humans, current commercial ROCK inhibitors for reducing intraocular pressure include Ripasudil (K-115) and Netarsudil (AR-13324). In the phase III clinical trial of Ripasudil, it was found that mild conjunctival hyperemia was the most common adverse reaction, with an incidence of up to 75%, and conjunctivitis and punctate keratitis also occurred. Netarsudil (AR-13324) is a ROCK/norepinephrine transporter (NET) inhibitor compound. In addition to acting as a ROCK inhibitor, it also has the effect of inhibiting norepinephrine and has the ability to continuously reduce intraocular pressure, and has good local tolerance, but it still has conjunctival hyperemia. In addition, Netarsudil (AR-13324) in Phase III clinical trials ROCKET1 and ROCKET2 (total 1,167 patients) is not as effective as the conventional glaucoma treatment drug Timolol in patients with intraocular pressure >25 mmHg, but in patients <25 mmHg, the efficacy is comparable to Timolol.

Currently known ROCK inhibitors still have various side effects when applied to reducing intraocular pressure, and the long-term use of single-mechanism drugs may lead to the problem of reduced drug efficacy, making it impossible for patients to use a single drug for a long time. Therefore, it is still needed to develop new intraocular pressure reducing drugs with new targets or multiple targets to effectively reduce intraocular pressure and reduce side effects.

SUMMARY

The present disclosure provides a compound represented by Formula (I), a pharmaceutically acceptable salt or ester, hydrate, solvate or crystalline form thereof:

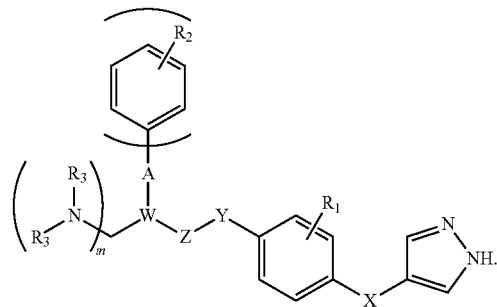

Formula (I)

The compound represented by Formula (I) is a β-amino acid derivative, and in Formula (I) X is a single bond or O; Y is NH or C=O; Z is C=O, C=S, NH,

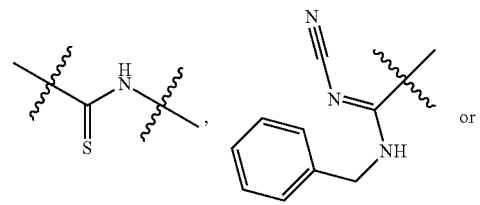

or

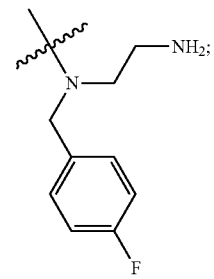

is C or N; A is a single bond, O, OH, OCH$_2$, a heterocycle or N$_3$; R$_1$ is H or F; R$_2$ is H, F, OH, CF$_3$, CH$_2$OH, CHO or

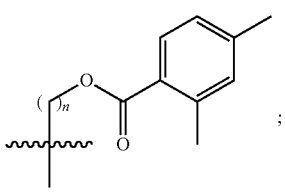

$R_3$ is H; n is 0 or 1; and m is 0 or 1.

The present disclosure also provides a kinase inhibitor comprising the compound represented by Formula (I), or a pharmaceutically acceptable salt or ester, hydrate, solvate or crystalline form thereof mentioned above.

The present disclosure further provides a pharmaceutical composition comprising the compound represented by Formula (I), or a pharmaceutically acceptable salt or ester, hydrate, solvate or crystalline form thereof mentioned above.

Moreover, the present disclosure provides a use of the compound represented by Formula (I), or a pharmaceutically acceptable salt or ester, hydrate, solvate or crystalline form thereof mentioned above as a kinase inhibitor.

The present disclosure also provides a use of the compound represented by Formula (I), or a pharmaceutically acceptable salt or ester, hydrate, solvate or crystalline form thereof mentioned above in the manufacture of a medicament, wherein the medicament is used for an in vivo related application that benefits from the inhibition of a kinase, and the kinase is at least one selected from a group consisting of: myosin light chain kinase 4; mitogen-activated protein kinase 19; and a Rho-associated protein kinase.

In addition, the present disclosure also provides a use of the compound represented by Formula (I), or a pharmaceutically acceptable salt or ester, hydrate, solvate or crystalline form thereof mentioned above in the manufacture of a medicament for reducing intraocular pressure.

A detailed description is given in the following embodiments with reference to the accompanying drawings.

BRIEF DESCRIPTION OF DRAWINGS

The patent or application file contains at least one drawing executed in color. Copies of this patent or patent application publication with color drawing will be provided by the USPTO upon request and payment of the necessary fee.

The present invention can be more fully understood by reading the subsequent detailed description and examples with references made to the accompanying drawings, wherein.

DETAILED DESCRIPTION

Figure 1A:
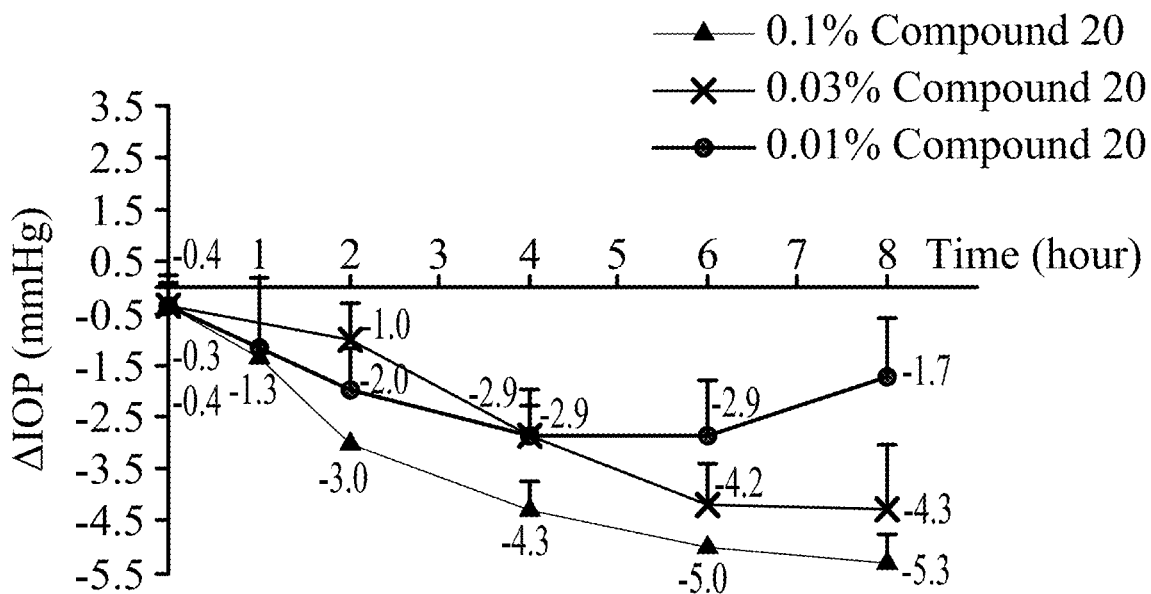
FIG. 1A shows the results of intraocular pressure measurements for administration of the compound of the present disclosure with a different concentration in rabbit eyes with normal intraocular pressure on the Day 1.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure provides a novel β-amino acid derivative and provides a pharmaceutically acceptable salt or ester, hydrate, solvate or crystalline form of the novel β-amino acid derivative at the same time.

The β-amino acid derivative mentioned above may comprise a compound represented by Formula (I), but it is not limited thereto:

Formula (I)

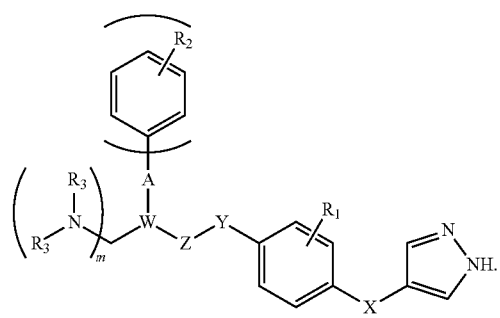

in Formula (I) shown above, X may be a single bond or O; Y may be NH or C=O; Z may be C=O, C=S, NH

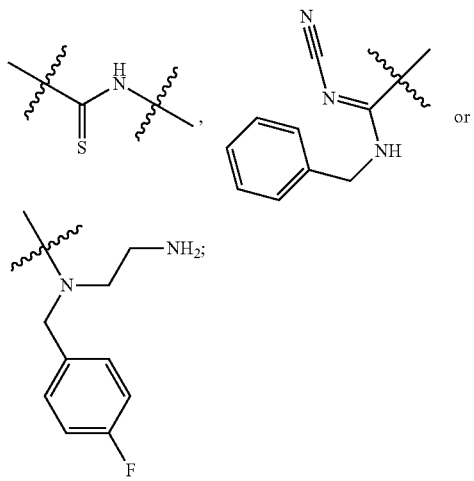

W may be C or N; A may be a single bond, O, OH, OCH$_2$, a heterocycle or N$_3$; R$_1$ may be H or F; R$_2$ may be H, F, OH, CF$_3$, CH$_2$OH, CHO or

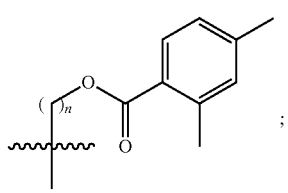

R$_3$ may be H; n may be 0 or 1; and m may be 0 or 1.

In the present disclosure, the compound represented by Formula (I) mentioned above may be present in the form of the individual optical isomers, a mixture of the individual enantiomers or a racemate, and may comprise, but is not limited to, a compound shown in the following Table 1.

TABLE 1

Examples for a compound represented by Formula (I)

| Compound Number | Compound 1 | Compound 2 |
|---|---|---|
| Structure | 1 | 2 |

| Compound Number | Compound 3 | Compound 4 |
|---|---|---|
| Structure | 3 | 4 |

TABLE 1-continued
Examples for a compound represented by Formula (I)
| Compound Number | Compound 5 | Compound 6 |
|---|---|---|
| Structure | 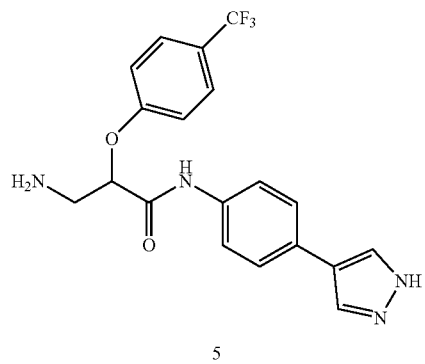 [SMILES: NCC(Oc1ccc(C(F)(F)F)cc1)C(=O)Nc1ccc(-c2cn[nH]c2)cc1]<br>5 | 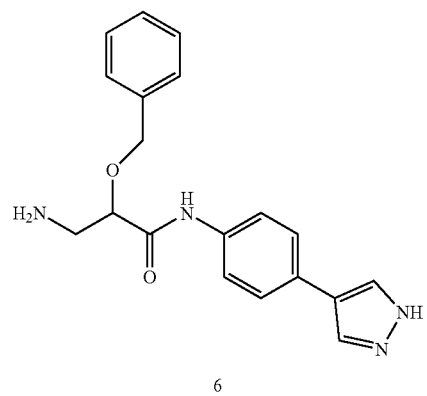 [SMILES: NCC(OCc1ccccc1)C(=O)Nc1ccc(-c2cn[nH]c2)cc1]<br>6 |
| Compound Number | Compound 7 | Compound 8 |
| Structure | 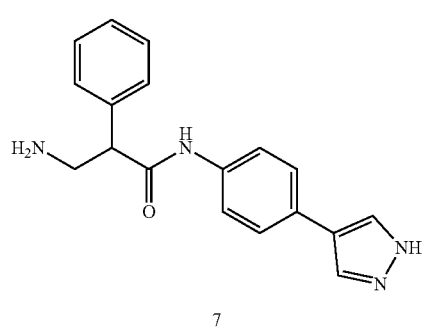 [SMILES: NCC(C(=O)Nc1ccc(-c2cn[nH]c2)cc1)c1ccccc1]<br>7 | 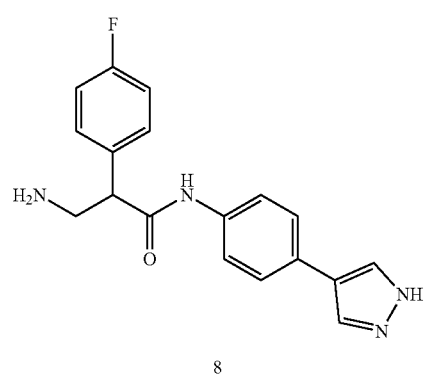 [SMILES: NCC(C(=O)Nc1ccc(-c2cn[nH]c2)cc1)c1ccc(F)cc1]<br>8 |
| Compound Number | Compound 9 | Compound 10 |
| Structure | 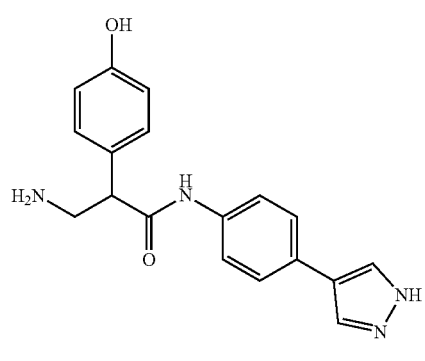<br>9 | 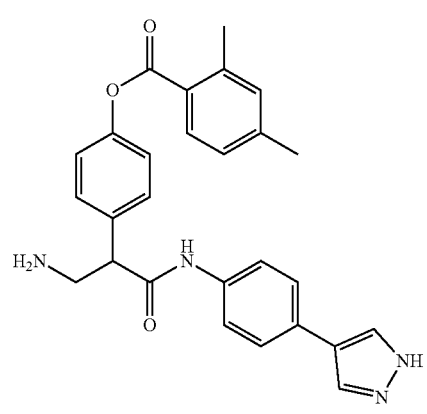<br>10 |

TABLE 1-continued
Examples for a compound represented by Formula (I)
| Compound Number | Compound 11 | Compound 12 |
|---|---|---|
| Structure | 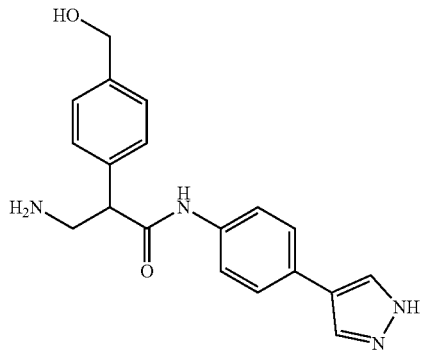 | 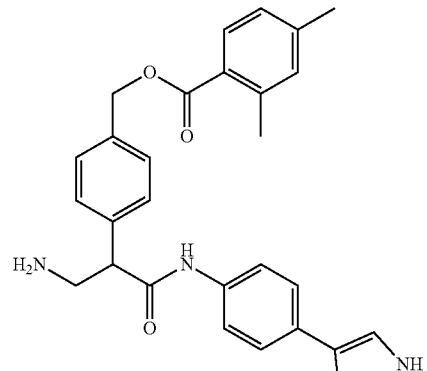 |
| Compound Number | Compound 13 | Compound 14 |
|---|---|---|
| Structure | 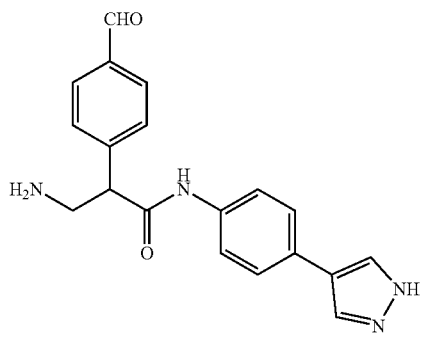 | 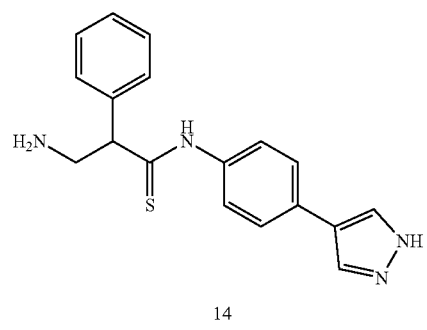 [SMILES: NCC(C(=S)Nc1ccc(-c2cn[nH]c2)cc1)c1ccccc1] |
| Compound Number | Compound 15 | Compound 16 |
|---|---|---|
| Structure | 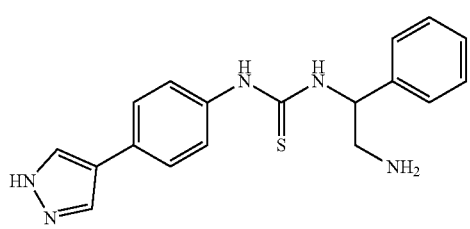 | 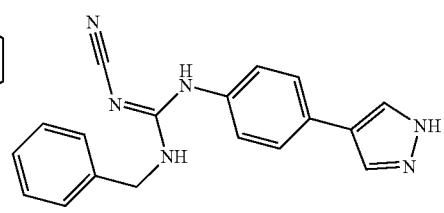 |

TABLE 1-continued

Examples for a compound represented by Formula (I)

| Compound Number | Compound 17 | Compound 18 |
|---|---|---|
| Structure | 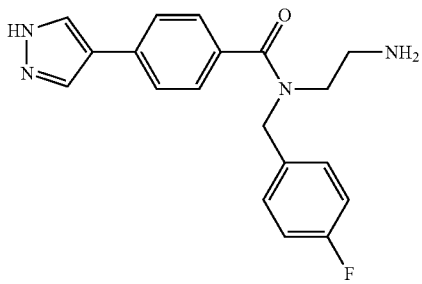<br>17 | 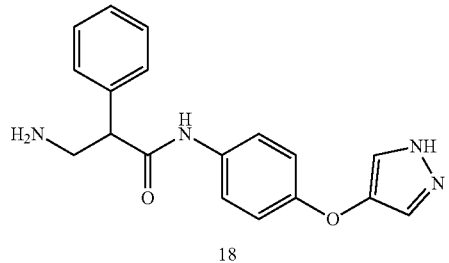 [SMILES: NCC(C(=O)Nc1ccc(Oc2cn[nH]c2)cc1)c1ccccc1]<br>18 |

| Compound Number | Compound 19 | Compound 20 |
|---|---|---|
| Structure | 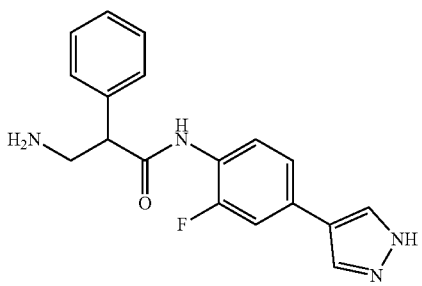<br>19 | 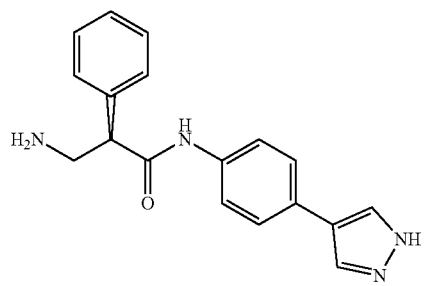<br>20 |

| Compound Number | Compound 21 |
|---|---|
| Structure | 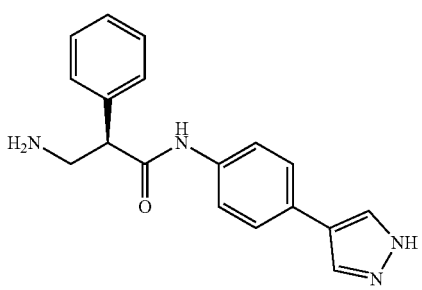<br>21 |

In one embodiment, the compound represented by formula (I) of the present disclosure may be the Compound 7 mentioned above, which is a racemic compound. In another embodiment, the compound represented by formula (I) of the present disclosure may be the Compound 20 mentioned above, which is an S-form compound, and more specifically, is an S-enantiomer.

In one embodiment, the novel β amino acid derivative of the present disclosure mentioned above or a pharmaceutically acceptable salt or ester, hydrate, solvate or crystalline form of the novel β amino acid derivative may have an effect of inhibiting a kinase, but it is not limited thereto. Example of the aforementioned kinase may comprise, but is not limited to, myosin light chain kinase 4 (MYLK-4), mitogen-activated protein kinase 19 (MAPK19, YSK-4), a Rho-associated protein kinase (ROCK) or any combination thereof. The Rho-associated protein kinase (ROCK) may comprise, but is not limited to, Rho-associated protein kinase-1 (ROCK-1).

In one embodiment, the novel β amino acid derivative of the present disclosure mentioned above or a pharmaceutically acceptable salt or ester, hydrate, solvate or crystalline form of the novel β amino acid derivative may have an effect of inhibiting myosin light chain kinase 4.

Furthermore, the novel β amino acid derivative of the present disclosure mentioned above or a pharmaceutically acceptable salt or ester, hydrate, solvate or crystalline form of the novel β amino acid derivative may have a synergistic target inhibiting effect. Therefore, in another embodiment, the novel β amino acid derivative of the present disclosure mentioned above or a pharmaceutically acceptable salt or ester, hydrate, solvate or crystalline form of the novel β amino acid derivative may have an effect of inhibiting mitogen-activated protein kinase 19.

Moreover, in another embodiment, the novel β amino acid derivative of the present disclosure mentioned above or a pharmaceutically acceptable salt or ester, hydrate, solvate or crystalline form of the novel β amino acid derivative may have an effect of simultaneously inhibiting myosin light chain kinase 4 and a Rho-associated protein kinase.

Also, in another embodiment, in another embodiment, the novel β amino acid derivative of the present disclosure mentioned above or a pharmaceutically acceptable salt or ester, hydrate, solvate or crystalline form of the novel β amino acid derivative may have an effect of simultaneously inhibiting mitogen-activated protein kinase 19 and a Rho-associated protein kinase.

In addition, the novel β amino acid derivative of the present disclosure mentioned above or a pharmaceutically acceptable salt or ester, hydrate, solvate or crystalline form of the novel β amino acid derivative may have an effect of simultaneously inhibiting myosin light chain kinase 4, mitogen-activated protein kinase 19 and a Rho-associated protein kinase.

In another embodiment, the novel β amino acid derivative of the present disclosure mentioned above or a pharmaceutically acceptable salt or ester, hydrate, solvate or crystalline form of the novel β amino acid derivative may have an effect of reducing intraocular pressure. In a specific embodiment, the novel β amino acid derivative of the present disclosure mentioned above or a pharmaceutically acceptable salt or ester, hydrate, solvate or crystalline form of the novel β amino acid derivative may achieve an effect of reducing intraocular pressure through myosin light chain kinase 4, mitogen-activated protein kinase 19, a Rho-associated protein kinase or any combination thereof.

Since the novel β amino acid derivative of the present disclosure mentioned above or a pharmaceutically acceptable salt or ester, hydrate, solvate or crystalline form of the novel β amino acid derivative may have an effect of reducing intraocular pressure, it may be applied to a treatment and/or prevention of ocular hypertension or a disease with ocular hypertension. The above-mentioned ocular hypertension refers to a symptom of an intraocular pressure greater than a normal range. For example, human normal intraocular pressure is about 10-21 mmHg, and ocular hypertension is a symptom of intraocular pressure greater than about 21 mmHg, such as greater than about 22 mmHg, greater than about 25 mmHg, greater than about 30 mmHg, etc., but it is not limited thereto.

In one embodiment, the novel β amino acid derivative of the present disclosure mentioned above or a pharmaceutically acceptable salt or ester, hydrate, solvate or crystalline form of the novel β amino acid derivative may be applied to a treatment and/or prevention of ocular hypertension with an intraocular pressure greater than about 25 mmHg, such as greater than about 30 mmHg.

Based on the foregoing, the present disclosure also provides a kinase inhibitor, which may comprise any of the novel β amino acid derivative of the present disclosure mentioned above or a pharmaceutically acceptable salt or ester, hydrate, solvate or crystalline form of the novel β amino acid derivative, but it not limited thereto.

In the kinase inhibitor of the present disclosure, the novel β amino acid derivative of the present disclosure mentioned above or a pharmaceutically acceptable salt or ester, hydrate, solvate or crystalline form of the novel β amino acid derivative may have an effect of inhibiting a kinase, and the kinase described herein may comprise, but is not limited to, myosin light chain kinase 4, mitogen-activated protein kinase 19, a Rho-associated protein kinase or any combination thereof. The Rho-associated protein kinase may comprise, but is not limited to, Rho-associated protein kinase-1.

In the kinase inhibitor of the present disclosure, in one embodiment, the novel β amino acid derivative of the present disclosure mentioned above or a pharmaceutically acceptable salt or ester, hydrate, solvate or crystalline form of the novel β amino acid derivative may have an effect of inhibiting myosin light chain kinase-4 and/or mitogen-activated protein kinase-19. In the kinase inhibitor of the present disclosure, in another embodiment, the novel β amino acid derivative of the present disclosure mentioned above or a pharmaceutically acceptable salt or ester, hydrate, solvate or crystalline form of the novel β amino acid derivative, in addition to an effect of inhibiting myosin light chain kinase-4 and/or mitogen-activated protein kinase-19, may also have an effect of inhibiting a Rho-associated protein kinase.

In one embodiment, the kinase inhibitor of the present disclosure may comprise the foregoing Compound 7 (which is a racemic compound) or Compound 20 (which is an S-form compound). In this specific embodiment, the kinase inhibitor of the present disclosure may have an effect of simultaneously inhibiting myosin light chain kinase 4, mitogen-activated protein kinase 19 and a Rho-associated protein kinase.

In addition, based on the foregoing, the present disclosure can also provide a use of the novel β amino acid derivative of the present disclosure mentioned above or a pharmaceutically acceptable salt or ester, hydrate, solvate or crystalline form of the novel β amino acid derivative as a kinase inhibitor.

In the use of the present disclosure, regarding the relevant description for the kinase inhibitory effect of the novel β amino acid derivative of the present disclosure mentioned above or a pharmaceutically acceptable salt or ester, hydrate, solvate or crystalline form of the novel β amino acid derivative is the same as that described above, and thus is not repeated herein.

In this use of the present disclosure, in a specific embodiment, the novel β amino acid derivative of the present disclosure mentioned above may be the foregoing Compound 7 (which is a racemic compound) or Compound 20 (which is an S-form compound). In this specific embodiment, the kinase inhibitor mentioned above may have an effect of simultaneously inhibiting myosin light chain kinase 4, mitogen-activated protein kinase 19 and a Rho-associated protein kinase.

In addition, the present disclosure also provides a pharmaceutical composition, which may comprise, but is not limited to, any of the novel β amino acid derivative of the present disclosure mentioned above or a pharmaceutically acceptable salt or ester, hydrate, solvate or crystalline form of the novel β amino acid derivative, but it not limited thereto.

In the pharmaceutical composition of the present disclosure, regarding all for the kinase inhibitory effect of the novel β amino acid derivative of the present disclosure mentioned above or a pharmaceutically acceptable salt or ester, hydrate, solvate or crystalline form of the novel β amino acid derivative are the same as those described above, and thus are not repeated herein.

In one embodiment, the pharmaceutical composition of the present disclosure may comprise the foregoing Compound 7 which is a racemic compound. In another embodiment, the pharmaceutical composition of the present disclosure may comprise the foregoing Compound 20 which is an S-form compound.

Moreover, in one embodiment, the above-mentioned pharmaceutical composition of the present disclosure may also comprise a pharmaceutically acceptable carrier or salt, but it is not limited thereto.

The pharmaceutically acceptable carrier mentioned above may comprise, but is not limited to, a solvent, a dispersion medium, a coating, an antibacterial and antifungal agent, or an isotonic and absorption delaying agent, etc. which is suitable for pharmaceutical administration. The pharmaceutical composition can be formulated into dosage forms for different administration routes utilizing conventional methods.

Moreover, the pharmaceutically acceptable salt mentioned above may comprise, but is not limited to, salts including inorganic cation, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also be organic salt, such as dicyclohexylamine salt, methyl-D-glucamine, and amino acid salt such as arginine, lysine, histidine, or glutamine.

Furthermore, the pharmaceutical composition of the present disclosure can be administered to a subject in need thereof, but is not limited thereto. The administration route of the pharmaceutical composition of the present disclosure may include parenteral manner, oral manner, via inhalation spray, or by implanted reservoir, but is not limited thereto. The parenteral methods may comprise, but is not limited to, smearing affected region, subcutaneous, intracutaneous, intravenous, intramuscular, intra-articular, intra-arterial, intrasynovial, intrasternal, intrathecal, intraleaional injection, external ophthalmic use, and intraocular injection, as well as infusion techniques, etc.

Topical use form for smearing may include ointment, emulsion, liquid, gel, etc., but it is not limited thereto. In addition, external use form for eye may include, but is not limited to, eye drops, eye ointment, eye gel, etc.

The subject in need to be administrated the pharmaceutical composition mentioned above may comprise, but is not limited to, a vertebrate. The vertebrate mentioned above may comprise a fish, an amphibian, a reptile, a bird or a mammal, but it is not limited thereto. Examples of the mammal may comprise, but are not limited to a human, an orangutan, a monkey, a horse, a donkey, a dog, a cat, a rabbit, a guinea pig, a rat and a mouse. In one embodiment, the said subject may be a human.

In one embodiment, the above-mentioned pharmaceutical composition of the present disclosure can be used to any in vivo-related application that benefits from the inhibition of a kinase, such as benefiting from treatment and/or prevention of any disease or symptom that benefits from the inhibition of a kinase, and example of the kinase described herein may include, but are not limited to, myosin light chain kinase-4, mitogen-activated protein kinase-19, a Rho-associated protein kinase, or any combination thereof.

In addition, the aforementioned in vivo-related application may include, but are not limited to, an ophthalmology-related application and/or a lung-related application, etc. Example of the ophthalmology-related application may include, protection of optic nerve, and/or prevention and/or treatment of high intraocular pressure, glaucoma, ocular stroke, macular degeneration, macular edema, diabetic retinopathy, Fuchs endothelial corneal dystrophy (FECD), corneal fibrosis or any combination thereof, etc., but it is not limited to thereto. Among them, glaucoma may include exfoliation glaucoma (XFG), open angle glaucoma, angle-closure glaucoma, secondary glaucoma, congenital glaucoma, etc., but not it is not limited to thereof. In addition, example of the lung-related application mentioned above may include, but is not limited to, prevention and/or treatment of pulmonary hypertension, chronic obstructive pulmonary disease (COPD), idiopathic pulmonary fibrosis (IPF), pulmonary emphysema, lung cancer, or any combination thereof, etc.

Moreover, the pharmaceutical composition of the present disclosure can be formulated into a pharmaceutical preparation, but is not limited thereto. In one embodiment, the pharmaceutical composition of the present disclosure can be formulated into an ophthalmic preparation, but it is not limited thereto. Example of the aforementioned ophthalmic preparation mentioned above may include, but is not limited to, an eye drop, an ophthalmic ointment, an ophthalmic gel, an intraocular injection formulation, etc. In a specific embodiment, the pharmaceutical composition of the present disclosure can be formulated into an eye drop.

In addition, the present disclosure can also provide a use of any of the novel amino acid derivative of the present disclosure mentioned above or a pharmaceutically acceptable salt or ester, hydrate, solvate or crystalline form of the novel β amino acid derivative in the manufacture of a medicament, wherein the medicament is used for an in vivo related application that benefits from the inhibition of a kinase. Example of the above-mentioned kinase may include, but is not limited to, myosin light chain kinase-4, mitogen-activated protein kinase-19, a Rho-associated protein kinase, or any combination thereof.

In one embodiment, in the above-mentioned use of the present disclosure, what is used is Compound 7, which is a racemic compound. In one embodiment, in the above-mentioned use of the present disclosure, what is used is the Compound 20, which is an S-form compound.

Furthermore, in the above-mentioned use of the present disclosure, the foregoing in vivo-related application may include, but are not limited to, an ophthalmology-related application and/or a lung-related application, etc. Example of the ophthalmology-related application may include, protection of optic nerve, and/or prevention and/or treatment of high intraocular pressure, glaucoma, ocular stroke, macular degeneration, macular edema, diabetic retinopathy, Fuchs endothelial corneal dystrophy (FECD), corneal fibrosis or any combination thereof, etc., but it is not limited to thereto. Among them, glaucoma may include exfoliation glaucoma, open angle glaucoma, angle-closure glaucoma, secondary glaucoma, congenital glaucoma, etc., but not it is not limited to thereof. In addition, example of the lung-related application mentioned above may include, but is not limited to, prevention and/or treatment of pulmonary hypertension, chronic obstructive pulmonary disease (COPD), idiopathic pulmonary fibrosis (IPF), pulmonary emphysema, lung cancer, or any combination thereof, etc.

In one embodiment, in the above-mentioned use of the present disclosure, the foregoing in vivo-related application may be the prevention and/or treatment of glaucoma.

In the above-mentioned use of the present disclosure, in another embodiment, a pharmaceutically acceptable carrier or salt may be together with any of the novel β amino acid derivative of the present disclosure mentioned above or a pharmaceutically acceptable salt or ester, hydrate, solvate or crystalline form of the novel β amino acid derivative to prepare the medicament mentioned above.

With regard to the pharmaceutically acceptable carrier or salt described herein, please refer to the relevant description of the pharmaceutically acceptable carrier or salt in the pharmaceutical composition of the present disclosure above, and thus is not repeated herein.

Moreover, the present disclosure also provides a use of any of the novel β amino acid derivative of the present disclosure mentioned above or a pharmaceutically acceptable salt or ester, hydrate, solvate or crystalline form of the novel β amino acid derivative in the manufacture of a medicament for reducing intraocular pressure.

In one embodiment, in the above-mentioned use of the present disclosure, what is used is Compound 7, which is a racemic compound. In one embodiment, in the above-mentioned use of the present disclosure, what is used is the Compound 20, which is an S-form compound.

Furthermore, in one embodiment, in the above-mentioned use of the present disclosure, the foregoing medicament for reducing intraocular pressure may be used for prevention and/or treatment of ocular hypertension or a disease with ocular hypertension. Regarding the relevant descriptions of the ocular hypertension or a disease with ocular hypertension, please refer to the above descriptions, and thus are not repeated herein.

In one embodiment, in the above-mentioned use of the present disclosure, the foregoing medicament for reducing intraocular pressure may be a medicament for treating glaucoma. The glaucoma mentioned above may include, but is not limited to, exfoliation glaucoma, open angle glaucoma, angle-closure glaucoma, secondary glaucoma, congenital glaucoma, etc.

In addition, in one embodiment, in the above-mentioned use of the present disclosure, the foregoing medicament for reducing intraocular pressure may be an ophthalmic preparation. The ophthalmic preparations may include, but are not limited to, an eye drop, an ophthalmic ointment, an ophthalmic gel, an intraocular injection formulation, etc. In a specific embodiment, the foregoing medicament for reducing intraocular pressure may be may be an eye drop.

In the above-mentioned use of the present disclosure, in another embodiment, a pharmaceutically acceptable carrier or salt may be together with any of the novel β amino acid derivative of the present disclosure mentioned above or a pharmaceutically acceptable salt or ester, hydrate, solvate or crystalline form of the novel β amino acid derivative to prepare the medicament for reducing intraocular pressure mentioned above.

With regard to the pharmaceutically acceptable carrier or salt described herein, please refer to the relevant description of the pharmaceutically acceptable carrier or salt in the pharmaceutical composition of the present disclosure above, and thus is not repeated herein.

EXAMPLES

Example 1

Synthesis of β-Amino Acid Derivatives

1. Synthesis of Compound 1 and Compound 2

The synthesis scheme of Compound 1 and Compound 2 is shown in the following Scheme 1.

Scheme 1

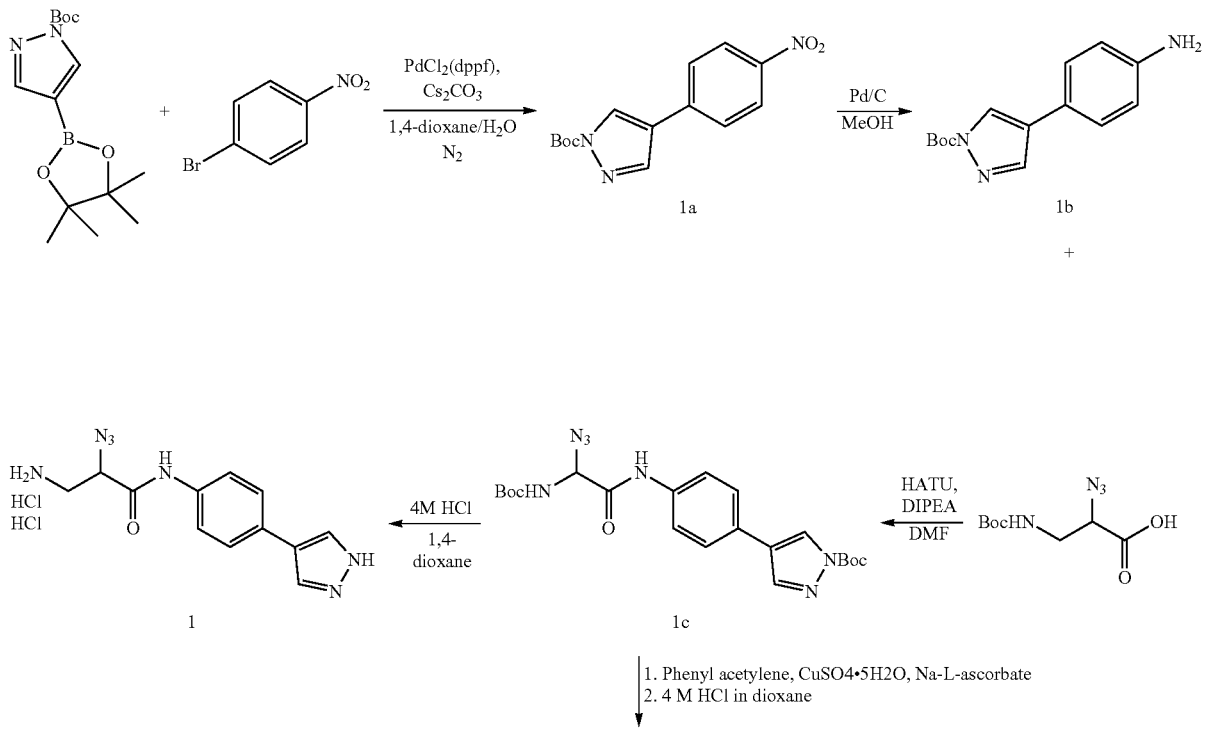

-continued

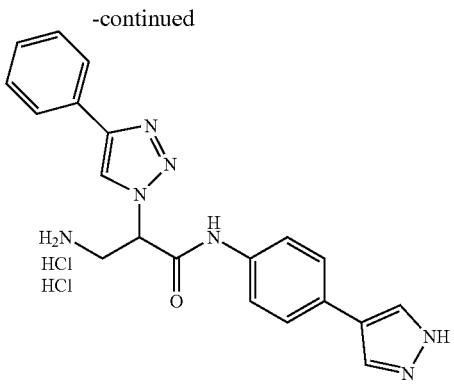

2

(1) Synthesis Example 1

To a mixture of 1-bromo-4-nitrobenzene (210 mg, 1.04 mmol), 1-Boc-4-pyrazoleboronic acid pinacol ester (305 mg, 1.04 mmol), $PdCl_2(dppf)$ (76 mg, 103.76 µmol) and $Cs_2CO_3$ (676 mg, 2.08 mmol) in a sealed tube, a mixed solvent (dioxane/$H_2O$=10/1, 6 mL) was injected under argon, and then the mixture mentioned above was stirred at 90° C. for 6 hours. After cooling to room temperature, the solvent was removed by rotary evaporation, and the residue was added with water and extracted with EtOAc (15 mL×3). The combined organic layers were washed with brine, dried over anhydrous $Na_2SO_4$ and filtered. The filtrate was concentrated and the residue was purified by flash chromatography (EtOAc/Hex=15%) on silica gel to give tert-butyl 4-(3-(2-(dimethylamino)ethoxy)-4-nitrophenyl)-1H-pyrazole (1a) which was a white solid (249 mg, 64%).

To a solution of tert-butyl 4-(3-(2-(dimethylamino)ethoxy)-4-nitrophenyl)-1H-pyrazole (1a) (360 mg) in MeOH (8 mL), 10% Pd/C was added, and the reaction mixture mentioned above was stirred at room temperature under $H_2$ balloon atmosphere for 1 hour. The mixture was filtered, and the filtrate was evaporated by rotary evaporation to give tert-butyl-(4-amino-3-(2-(dimethylamino)ethoxy)phenyl)-1H-pyrazole (1b) as brown solid (320 mg, 97%). $^1$H-NMR (500 MHz, $CDCl_3$) δ: 8.44 (s, 1H), 8.27 (d, J=9.0 Hz, 2H), 8.06 (s, 1H), 7.69-7.68 (m, 4H), 1.68 (s, 9H), 1.59 (s, 9H).

2-azido-3-((tert-butoxycarbonyl)amino)propanoic acid (1.2 eq), HATU (1.5 eq) and DIPEA (2 eq) were dissolved in DMF (0.1M), and tert-butyl-(4-amino-3-(2-(dimethylamino)ethoxy)phenyl)-1H-pyrazole (1b) (1.0 eq) was added thereto to form a mixture and stirred at room temperature for 1 hour. The reaction was workup by water and extracted with EtOAc. The organic layer was collected and dried over $Na_2SO_4$, and the extract was condensed under reduced pressure. The residue was purified with silica gel (EtOAc/Hex=20%), and the desired compound tert-butyl 4-(4-(2-azido-3-((tert-butoxycarbonyl)amino)propanamido)phenyl)-1H-pyrazole-1-carboxylate (1c) was given. $^1$H-NMR (500 MHz, $CDCl_3$) δ: 8.41 (s, 1H), 8.25 (s, 1H), 7.94 (s, 1H), 7.58 (d, J=9.0 Hz, 2H), 7.47 (d, J=9.0 Hz, 2H), 5.07 (s, 1H), 4.27 (m, 1H), 3.72 (m, 1H), 3.60 (m, 1H), 1.65 (s, 9H), 1.43 (s, 9H).

4 M HCl in 1,4-dioxane (20 eq) and tert-butyl 4-(4-(2-azido-3-((tert-butoxycarbonyl) amino)propanamido)phenyl)-1H-pyrazole-1-carboxylate (1c) (1 eq) were stirred at room temperature for 1 hour. The white solid was collected by filtration, washed with 1,4-dioxane and DCM. The white solid was dried by vacuum to give N-(4-(1H-pyrazol-4-yl) phenyl)-3-amino-2-azidopropanamide dihydrochloride (1). $^1$H-NMR (500 MHz, D2O) δ: 8.30 (s, 2H), 7.67 (m, 2H), 7.55 (m, 2H), 4.76 (m, 1H), 3.57 (dd, J=13.5, 4.5 Hz, 1H), 3.44 (dd, J=13.5, 7.5 Hz, 1H), 3.60 (m, 1H).

(2) Synthesis Example 2

Tert-butyl 4-(4-(2-azido-3-((tert-butoxycarbonyl)amino) propanamido)phenyl)-1H-pyrazole-1-carboxylate (1c) (1 eq), phenyl acetylene (1.1 eq), copper(II) sulfate (0.2 eq) and (+)-Na-L-ascorbate (0.2 eq) were stirred in THF and 2-3 drops $H_2O$. The mixture was stirred at room temperature overnight, and then the solvent was removed. The residue was purified with silica gel (EtOAc/Hex=20%), and the desired compound tert-butyl 4-(4-(3-((tert-butoxycarbonyl) amino)-2-(4-phenyl-1H-1,2,3-triazol-1-yl) propanamido) phenyl)-1H-pyrazole-1-carboxylate was given. $^1$H-NMR (500 MHz, $CDCl_3$) δ: 8.98 (s, 1H), 8.24 (s, 1H), 8.11 (s, 1H), 7.94 (s, 1H), 7.83 (d, J=7.5 Hz, 2H), 7.58 (d, J=8.5 Hz, 2H), 7.46 (d, J=8.5 Hz, 2H), 7.42 (t, J=7.0 Hz, 2H), 7.34 (t, J=7.0 Hz, 1H), 5.61 (s, 1H), 5.15 (s, 1H), 4.10-4.06 (m, 1H), 3.96-3.95 (m, 1H), 1.65 (s, 9H), 1.40 (s, 9H).

The preparation method for Compound 2 was similar to that for Compound 1. The distinction therebetween was that the compound tert-butyl 4-(4-(2-azido-3-((tert-butoxycarbonyl)amino)propanamido)phenyl)-1H-pyrazole-1-carboxylate was replace with the compound tert-butyl 4-(4-(3-((tert-butoxycarbonyl)amino)-2-(4-phenyl-1H-1,2,3-triazol-1-yl) propanamido)phenyl)-1H-pyrazole-1-carboxylate to obtain the product N-(4-(1H-pyrazol-4-yl)phenyl)-3-amino-2-(4-phenyl-1H-1,2,3-triazol-1-yl) propenamide dihydrochloride (2). $^1$H-NMR (500 MHz, $CD_3OD$) δ: 8.63 (s, 1H), 8.61 (s, 1H), 7.88 (d, J=7.5 Hz, 2H), 7.74 (d, J=8.5 Hz, 2H), 7.67 (d, J=8.5 Hz, 2H), 7.45 (t, J=8.5 Hz, 2H), 7.37 (t, J=8.5 Hz, 1H), 5.97 (t, J=6.0 Hz, 1H), 5.54 (s, 1H), 3.92 (d, J=6.0 Hz, 2H), 3.34 (s, 2H).

2. Synthesis of Compound 3 to Compound 5

The synthesis scheme of Compound 3 to Compound 5 is shown in the following Scheme 2.

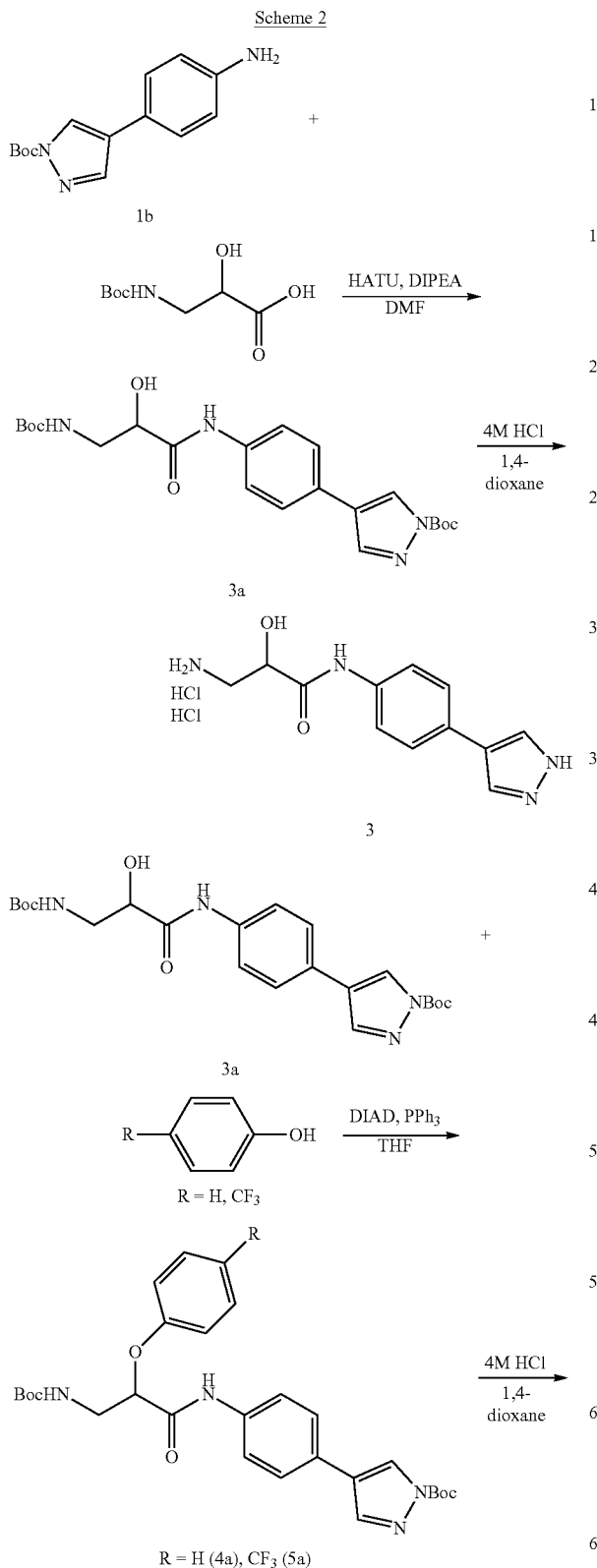

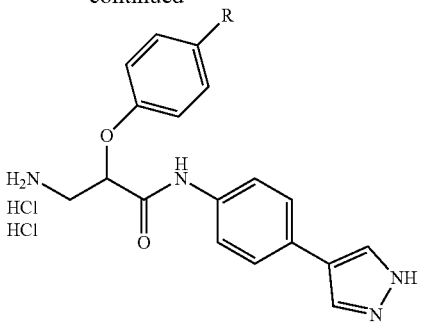

(3) Synthesis Example 3

The preparation method for Compound 3a was similar to that for Compound 1c. The distinction therebetween was that the compound 2-azido-3-((tert-butoxycarbonyl)amino) propanoic acid was replace with the compound 3-((tert-butoxycarbonyl)amino)-2-hydroxypropanoic acid to obtain the product tert-butyl 4-(4-(3-((tert-butoxycarbonyl)amino)-2-hydroxypropanamido)phenyl)-1H-pyrazole-1-carboxylate (3a). The synthesis method for the final product N-(4-(1H-pyrazol-4-yl)phenyl)-3-amino-2-hydroxypropanamide dihydrochloride (3) synthesis was similar to that for Compound 1. $^1$H-NMR (500 MHz, D$_2$O) δ: 8.20 (s, 2H), 7.70 (d, J=8.0, 2H), 7.56 (d, J=8.0, 2H), 4.64 (dd, J=8.5, 4.5 Hz, 1H), 3.51 (dd, J=13.5, 4.5 Hz, 1H), 3.36-3.31 (m, 1H).

(4) Synthesis Example 4

To a zero degree solution of compound 3a (1 eq), phenol (1 eq), PPh$_3$ (2 eq) in 10 mL THF, DIAD (1.5 eq) was added dropwise. The mixture mentioned above was stirred at room temperature for 2 hours. The solvent was removed by reduced pressure, and the crude product was purified by column chromatography (EtOAc/Hex=10%) to get tert-butyl 4-(4-(3-((tert-butoxycarbonyl)amino)-2-phenoxypropanamido)phenyl)-1H-pyrazole-1-carboxylate (4a) which was an oil. $^1$H-NMR (500 MHz, CDCl$_3$) δ: 8.26 (s, 2H), 7.96 (s, 1H), 7.58 (d, J=9.0 Hz, 2H), 7.48 (d, J=9.0 Hz, 2H), 7.35 (t, J=8.0 Hz, 2H), 7.09-6.99 (m, 3H), 5.03 (brs, 1H), 4.76 (t, J=5.0 Hz, 1H), 3.81-3.78 (m, 1H), 3.73-3.70 (m, 1H), 1.68 (s, 9H), 1.45 (s, 9H). The synthesis method for the final product N-(4-(1H-pyrazol-4-yl)phenyl)-3-amino-2-phenoxypropanamide dihydrochloride (4) was similar to that for Compound 1. $^1$H-NMR (500 MHz, CD$_3$OD) δ: 8.30 (s, 2H), 7.66 (d, J=9.0 Hz, 2H), 7.59 (d, J=9.0 Hz, 2H), 7.36 (d, J=8.5 Hz, 2H), 7.12 (d, J=8.5 Hz, 1H), 7.07 (t, J=7.0 Hz, 1H), 7.01-6.98 (m, 1H), 3.75-3.66 (m, 1H), 3.60-3.50 (m, 2H).

(5) Synthesis Example 5

The synthesis method for the compound N-(4-(1H-pyrazol-4-yl)phenyl)-3-amino-2-(4-(trifluoromethyl) phenoxy) propenamide dihydrochloride (5) was similar to that for Compound 4. $^1$H-NMR (500 MHz, CD$_3$OD) δ: 8.14 (br, 2H), 7.68 (d, J=9.0, 2H), 7.63 (d, J=6.5, 2H), 7.58 (d, J=6.5, 2H), 7.26 (d, J=9.0, 2H), 5.21 (m, 1H), 3.60-3.58 (m, 2H). $^1$H-NMR (500 MHz, CD$_3$OD) δ: 8.14 (br, 2H), 7.68 (d, 2H), 7.63 (d, 2H), 7.58 (d, 2H), 7.26 (d, J=9.0, 2H), 5.21 (m, 1H), 3.60-3.58 (m, 2H).

3. Synthesis of Compound 6

The synthesis scheme of Compound 6 is shown in the following Scheme 3:

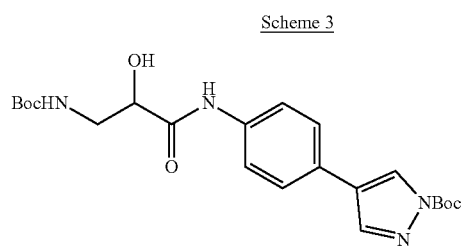

(6) Synthesis Example 6

To a zero degree solution of compound 3a (1 eq) in 10 mL THF, NaH (1.5 eq) was add. The mixture mentioned above was stirred at zero degree for 1 hour, and then BnBr (1.5 eq) was added dropwise thereto. The reaction mixture mentioned above was stirred at room temperature for 6 hours. The reaction was workup by water and extracted with EtOAc. The organic layer was collected and dried over Na$_2$SO$_4$, and then the extract was removed under reduced pressure. The residue was purified with silica gel (EtOAc/Hex=5% to 15%) to give the desired compound tert-butyl 4-(4-(2-(benzyloxy)-3-((tert-butoxycarbonyl)amino)propanamido)phenyl)-1H-pyrazole-1-carboxylate (6a). $^1$H-NMR (500 MHz, CDCl$_3$) δ: 8.44 (s, 1H), 8.27 (s, 1H), 7.97 (s, 1H), 7.56 (d, J=8.5 Hz, 2H), 7.48 (d, J=8.5 Hz, 2H), 7.41-7.35 (m, 5H), 4.93 (brs, 1H), 4.82 (d, J=8.5 Hz, 1H), 4.66 (d, J=11.0 Hz, 1H), 4.06 (t, J=5.0 Hz, 1H), 3.65-3.61 (m, 2H), 1.68 (s, 9H), 1.44 (s, 9H).

The synthesis method for the final product N-(4-(1H-pyrazol-4-yl)phenyl)-3-amino-2-(benzyloxy) propanamidedihydrochloride (6) was similar to that for Compound 1. $^1$H-NMR (500 MHz, CD$_3$OD) δ: 8.46 (s, 2H), 7.69-7.66 (m, 4H), 7.49 (d, J=7.5 Hz, 2H), 7.38 (t, J=7.5 Hz, 2H), 7.34-7.31 (m, 1H), 4.78 (d, J=11.5 Hz, 1H), 4.75 (d, J=11.5 Hz, 1H), 4.36-4.34 (m, 1H), 3.36-3.31 (m, 2H).

4. Synthesis of Compound 7 and Compound 8

The synthesis scheme of Compound 7 and Compound 8 is shown in the following Scheme 4.

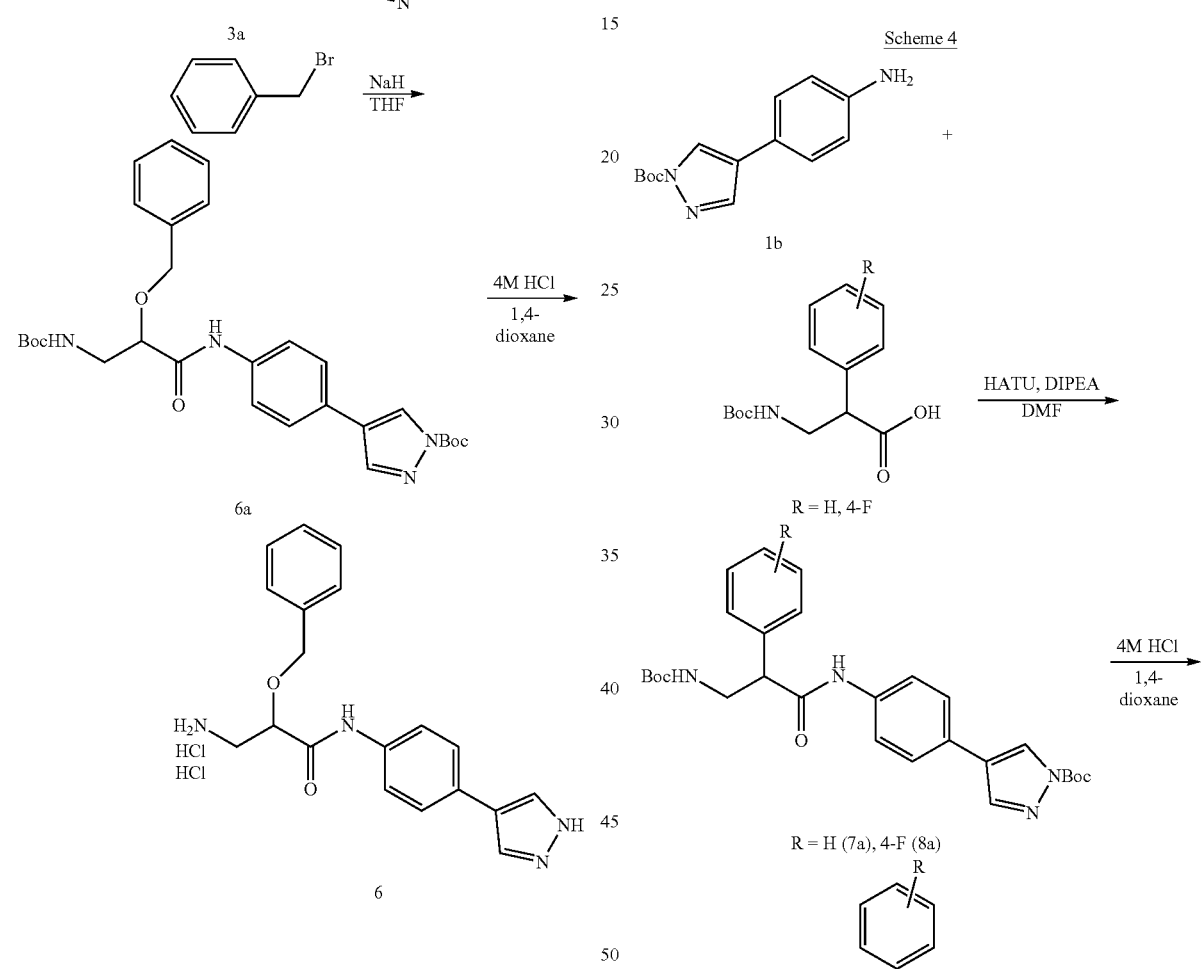

(7) Synthesis Example 7

The preparation methods for the intermediate compounds 7a and 8a were similar to that for Compound 1c.

The intermediate compound tert-butyl 4-(4-(3-((tert-butoxycarbonyl)amino)-2-phenylpropanamido)phenyl)-1H- pyrazole-1-carboxylate 7a was white powder. ¹H-NMR (500 MHz, CDCl₃) δ: 8.22 (s, 1H), 7.92 (s, 1H), 7.49 (d, J=8.5 Hz, 2H), 7.42 (d, J=8.5 Hz, 2H), 5.14 (s, 1H), 3.90 (m, 1H), 3.65 (m, 1H), 3.55 (m, 1H), 1.64 (s, 9H), 1.40 (s, 9H).

The intermediate compound tert-butyl 4-(4-(3-((tert-butoxycarbonyl)amino)-2-(4-fluorophenyl)propanamido)phenyl)-1H-pyrazole-1-carboxylate 8a was white powder. ¹H-NMR (CDCl₃, 500 MHz) 8.25 (s, 1H), 7.94 (s, 1H), 7.53-7.51 (m, 3H), 7.45 (d, J=8.5 Hz, 2H), 7.34 (t, J=8.5 Hz, 2H), 7.05 (t, J=8.5 Hz, 2H), 5.13 (brs, NH, 1H), 3.92 (s, 1H), 3.65-3.64 (m, 1H), 3.54-3.51 (m, 1H), 1.67 (s, 9H), 1.47 (s, 9H).

The preparation methods for the final Compounds 7 and 8 were similar to that for Compound 1.

The final compound N-(4-(1H-pyrazol-4-yl)phenyl)-3-amino-2-phenylpropanamide dihydrochloride (7) was white powder. ¹H-NMR (500 MHz, CD₃OD) δ: 8.55 (br, 2H), 7.69 (d, J=8.5, 2H), 7.63 (d, J=8.5, 2H), 7.47-7.34 (m, 5H), 4.15-4.17 (m, 1H), 3.61 (dd, J=12.5, 9.5 Hz, 1H), 3.25 (dd, J=12.5, 5.5 Hz, 1H), 3.60 (m, 1H).

The final compound N-(4-(1H-pyrazol-4-yl)phenyl)-3-amino-2-(4-fluorophenyl) propanamide dihydrochloride (8) was white powder. ¹H-NMR (500 MHz, D₂O) δ: 8.07 (s, 2H), 7.42 (d, J=8.5 Hz, 2H), 7.34 (dd, J=5.5, 8.5 Hz, 2H), 7.26 (d, J=8.5 Hz, 2H), 7.08 (t, J=8.5 Hz, 2H), 4.06 (t, J=7.5 Hz, 1H), 3.52 (dd, J=7.5, 13.0 Hz, 1H), 3.33 (dd, J=7.5, 13.0 Hz, 1H).

5. Synthesis of Compound 9

(8) Synthesis Example 8

The synthetic scheme of Compound 9f is shown in the following Scheme 5.

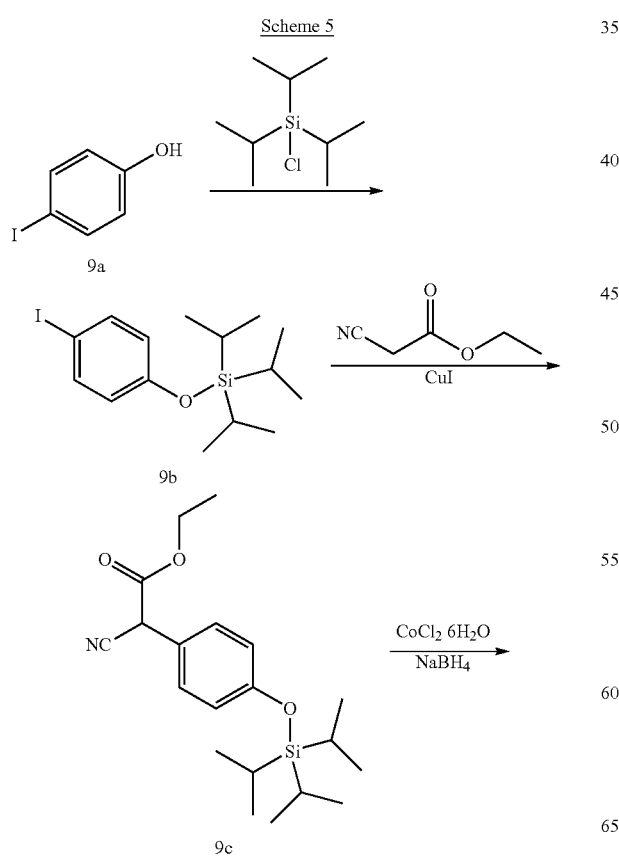

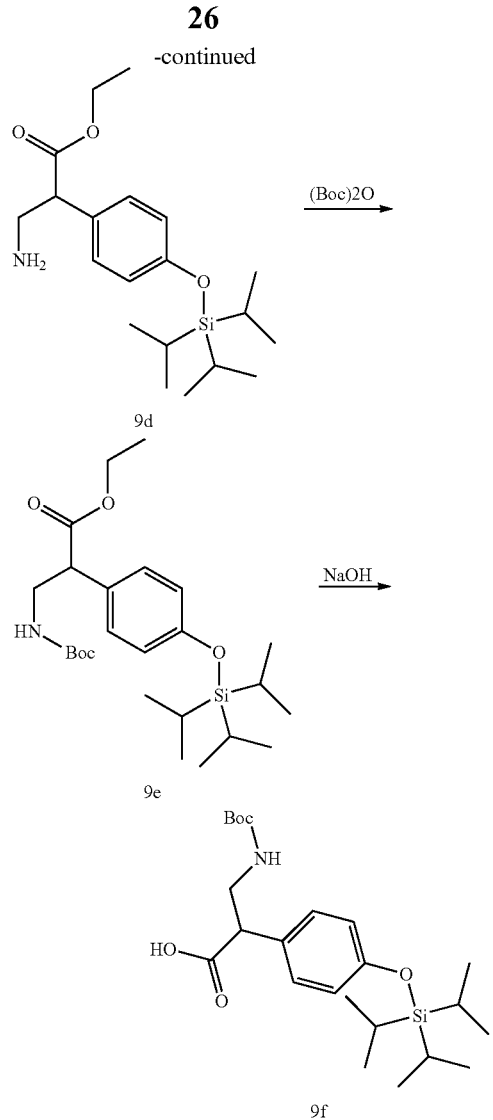

To a solution of iodophenol (9a) (100 g, 454.5 mmol) in DCM (1000 mL), imidazole (68 g, 999.9 mmol) was added, followed by dropwise addition of TIPSCl (87.3 g, 454.5 mmol). The mixture mentioned above was stirred for 16 hours and poured into ice/water, and extracted with DCM. The organic layers were washed with brine, dried over Na₂SO₄ and concentrated. The residue was purified by silica gel column chromatography (eluting solvent: ethyl acetate/petroleum ether=1/50) to give Compound 9b (170 g, 99.1%), which was colorless oil. ¹H-NMR (CDCl₃, 400 MHz): δ: 1.05-1.08 (d, 18H), 1.20-1.28 (m, 3H), 6.64-6.66 (m, 2H), 7.47-7.49 (m, 2H).

To a solution of Compound 9b (140 g, 372.3 mmol) in dioxane (1500 mL), ethyl 2-cyanoacetate (63.1 g, 558.8 mmol), picolinic acid (13.8 g, 111.7 mmol), Cs₂CO₃ (242 g, 744.6 mmol) and CuI (21.2 g, 111.7 mmol) were added. The mixture was mentioned above stirred for 2 hours at 90° C. and filtered. The organic layer was concentrated and purified by silica gel column chromatography (eluting solvent: ethyl acetate/petroleum ether=1/20) to give Compound 9c (44 g, 32.7%), which was white solid.

To a solution of compound 9c (22 g, 60.9 mmol) in MeOH/THF (2:1, 660 mL), CoCl₂6 H₂O (44 g, 184.9 mmol) and NaBH₄ (33 g, 868.4 mmol) were added at −20° C. The mixture mentioned above was stirred for 30 minutes and filtered to obtain a filtrate. To the filtrate, (Boc)₂O (40 g, 183.5 mmol) was added, and stirred for 0.5 hours at room temperature. Next, the mixture mentioned above was poured into ice/water and extracted with EtOAc. The organic layer was washed with brine, dried over Na₂SO₄ and concentrated. The residue was purified by silica gel column chromatography (eluting solvent: ethyl acetate/petroleum ether=1/30) to give compound 9e (10.5 g, 35.9%), which was yellow oil. ¹H-NMR (CDCl₃, 400 MHz): δ: 1.53-1.09 (t, 18H), 1.17-1.28 (m, 6H), 1.42 (s, 9H), 3.46-3.56 (m, 2H), 3.77-3.80 (t, 1H), 4.11-4.18 (m, 2H), 4.82 (s, 1H), 6.81-6.83 (d, 2H), 7.09-7.11 (d, 2H).

To a solution of Compound 9e (10 g, 21.5 mmol) in EtOH/H₂O (10:1, 220 mL), NaOH (2 g, 49.5 mmol) was added and stirred for 1 hour at room temperature. The mixture mentioned above was neutralized with 1 N HCl and extracted with EtOAc. The organic layer was washed with brine, dried over Na₂SO₄ and concentrated. The residue was purified by silica gel column chromatography (eluting solvent: ethyl acetate/petroleum ether=1/10) to give compound 9f (2.5 g, 26.6%), which was a white solid. ¹H-NMR (DMSO-d6, 400 MHz): δ: 1.08-1.10 (d, 18H), 1.22-1.32 (m, 3H), 1.37 (s, 9H), 3.23-3.28 (m, 1H), 3.42-3.46 (t, 1H), 3.69-3.73 (t, 1H), 6.85-6.87 (d, 3H), 7.16-7.18 (d, 2H).

(9) Synthesis Example 9

The synthesis scheme of Compound 9 is shown in the following Scheme 6.

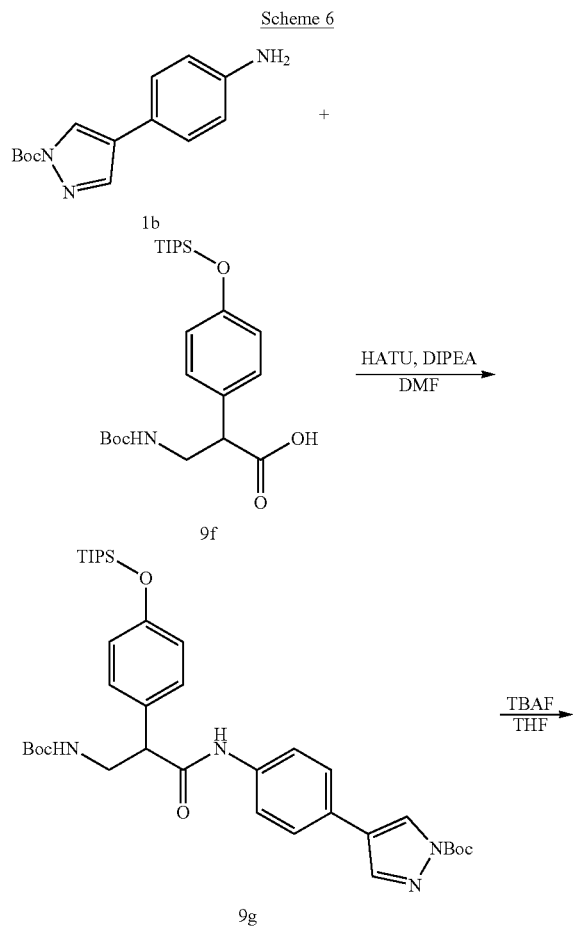

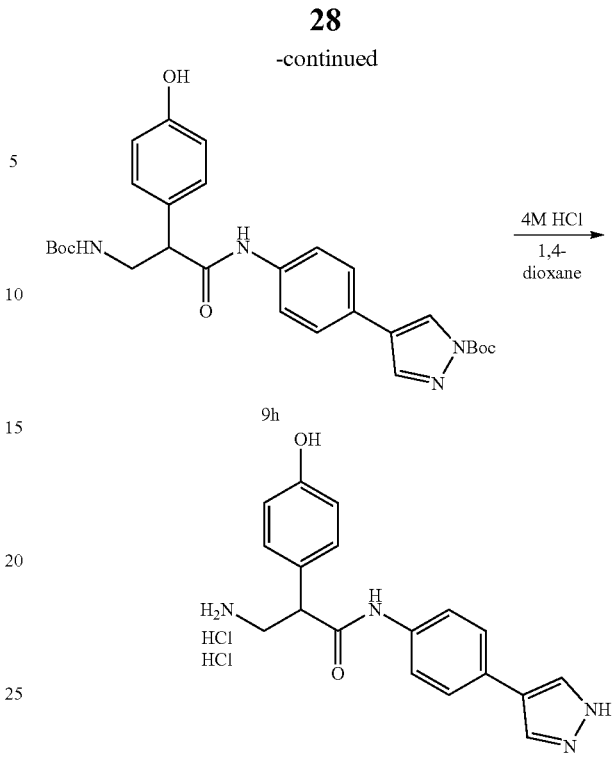

The preparation method for the intermediate Compounds 9g was similar to that for Compound 1c.

The intermediate compound tert-butyl 4-(4-(3-((tert-butoxycarbonyl)amino)-2-(4-((triisopropylsilyl)oxy)phenyl) propanamido)phenyl)-1H-pyrazole-1-carboxylate 9g was white powder. ¹H-NMR (CDCl₃, 500 MHz) 8.25 (s, 1H), 7.94 (s, 1H), 7.49 (d, J=8.5 Hz, 2H), 7.44 (d, J=8.5 Hz, 2H), 7.30 (brs, NH, 1H), 7.19 (d, J=8.5 Hz, 2H), 6.87 (d, J=8.5 Hz, 2H), 5.17 (brs, NH, 1H), 3.82 (s, 1H), 3.64-3.62 (m, 1H), 3.56-3.53 (m, 1H), 1.67 (s, 9H), 1.43 (s, 9H), 1.30-1.20 (m, 3H), 1.09 (d, J=7.0 Hz, 18H).

To a stirred solution of tert-butyl 4-(4-(3-((tert-butoxycarbonyl)amino)-2-(4-((triisopropylsilyl)oxy)phenyl)propanamido)phenyl)-1H-pyrazole-1-carboxylate (9g) (1030 mg, 1.52 mmol) in THF (10 mL), 1 M TBAF in THF solution (3.03 mL, 3.03 mmol) was added. The resulting mixture was stirred at room temperature for 1 hour. The reaction was workup by water and extracted with EtOAc. The organic layer was collected and dried over Na₂SO₄, and the extract was condensed under reduced pressure. The residue was purified with preparative reverse HPLC (80% ACN, 20% H₂O), and then lyophilized to get tert-butyl 4-(4-(3-((tert-butoxycarbonyl)amino)-2-(4-hydroxyphenyl) propanamido)phenyl)-1H-pyrazole-1-carboxylate (9h) (600 mg, 76%), which was white powder. ¹H-NMR (CDCl₃, 500 MHz) 8.25 (s, 1H), 7.94 (s, 1H), 7.50 (d, J=8.5 Hz, 2H), 7.45-7.43 (m, 3H), 7.15 (d, J=8.5 Hz, 2H), 6.81 (d, J=8.5 Hz, 2H), 5.26 (brs, NH, 1H), 3.80 (s, 1H), 3.62 (s, 1H), 3.55-3.53 (m, 1H), 1.67 (s, 9H), 1.62 (brs, OH, 1H), 1.43 (s, 9H).

The preparation method for the final Compound 9 was similar to that for Compound 1.

The final compound N-(4-(1H-pyrazol-4-yl)phenyl)-3-amino-2-(4-hydroxyphenyl) propanamide dihydrochloride (9) was white powder. ¹H-NMR (500 MHz, D₂O) δ: 8.06 (s, 2H), 7.39 (d, J=8.5 Hz, 2H), 7.24 (d, J=8.5 Hz, 2H), 7.20 (d, J=8.5 Hz, 2H), 6.82 (d, J=8.5 Hz, 2H), 3.97 (t, J=7.5 Hz, 1H), 3.49 (dd, J=7.5, 13.0 Hz, 1H), 3.30 (dd, J=7.5, 13.0 Hz, 1H).

6. Synthesis of Compound 10

(10) Synthesis Example 10

The synthesis scheme of compound 10 is shown in the following Scheme 7.

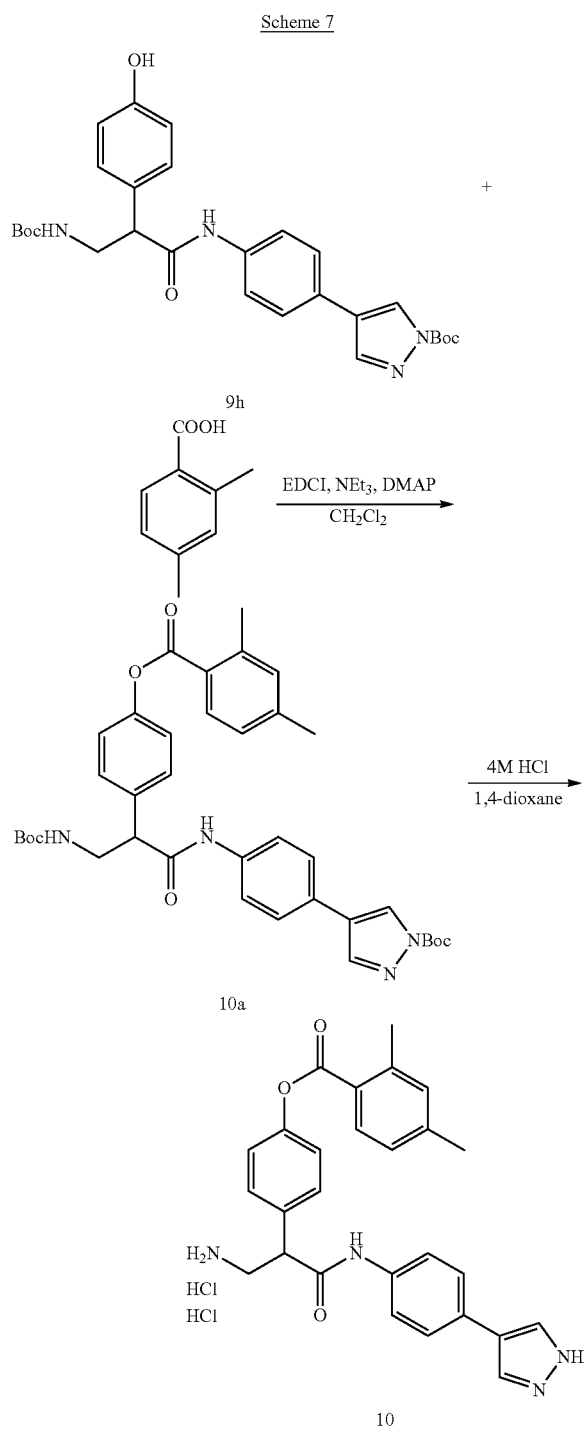

To a stirred solution of tert-butyl 4-(4-(3-((tert-butoxycarbonyl)amino)-2-(4-hydroxyphenyl)propanamido)phenyl)-1H-pyrazole-1-carboxylate (9h) (356 mg, 0.68 mmol), 2,4-dimethylbenzoic acid (103 mg, 0.68 mmol) and NEt₃ (143 ul, 1.02 mmol) in $CH_2Cl_2$ (20 mL), EDCI (196 mg, 1.02 mmol) and DMAP (25 mg, 0.21 mmol) were added. The resulting mixture was stirred for 16 hours. The reaction was workup by saturated citric acid and extracted with EtOAc. The organic layer was collected and dried over $Na_2SO_4$, and the solvent was removed under reduced pressure. The residue was purified with preparative reverse HPLC (100% ACN), and then lyophilized to get tert-butyl 4-(4-(3-((tert-butoxycarbonyl)amino)-2-(4-((2,4-dimethylbenzoyl)oxy)phenyl)propanamido)phenyl)-1H-pyrazole-1-carboxylate (10a) (355 mg, 80%), which was white powder. $^1$H-NMR ($CDCl_3$, 500 MHz) 8.26 (s, 1H), 8.06 (d, J=8.0 Hz, 1H), 7.96 (s, 1H), 7.53 (d, J=8.5 Hz, 2H), 7.52-7.42 (m, 5H), 7.21 (d, J=8.5 Hz, 2H), 5.15 (brs, NH, 1H), 3.95 (s, 1H), 3.68-3.67 (m, 1H), 3.58-3.55 (m, 1H), 2.63 (s, 3H), 2.40 (s, 3H), 1.67 (s, 9H), 1.44 (s, 9H).

In the 20 mL vial, tert-butyl 4-(4-(3-((tert-butoxycarbonyl)amino)-2-(4-(2,4-dimethylbenzoyl)oxy)phenyl)propanamido)phenyl)-1H-pyrazole-1-carboxylate (l0a) (350 mg, 0.54 mmol) and 4 M HCl in dioxane (2.7 mL) were charged. The resulting mixture was stirred at room temperature for 1 hour. The solvent was removed under reduced pressure to give the desired product 4-(1-((4-(1H-pyrazol-4-yl)phenyl)amino)-3-amino-1-oxopropan-2-yl)phenyl 2,4-dimethylbenzoate dihydrochloride (10) which was as white powder (271 mg, 96%). $^1$H-NMR (500 MHz, DMSO) δ10.47 (s, 1H), 8.08 (brs, 3H), 8.02 (s, 2H), 7.94 (d, J=8.5 Hz, 1H), 7.61 (d, J=9.0 Hz, 2H), 7.53 (d, J=8.5 Hz, 2H), 7.50 (d, J=8.5 Hz, 2H), 7.28 (d, J=8.5 Hz, 2H), 7.19 (d, J=9.0 Hz, 2H), 4.18 (dd, J=5.5, 8.5 Hz, 1H), 3.15-3.06 (m, 1H), 2.52 (s, 3H), 2.34 (s, 3H).

7. Synthesis of Compound 11

(11) Synthesis Example 11

The synthesis scheme of Compound 11g is shown in the following Scheme 8.

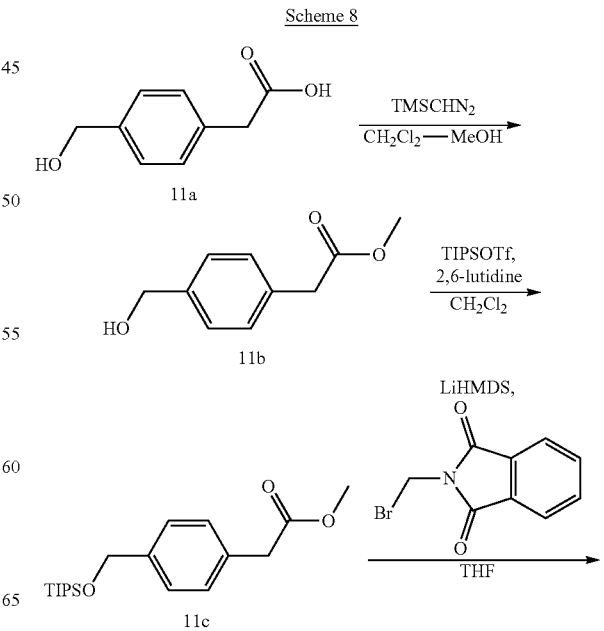

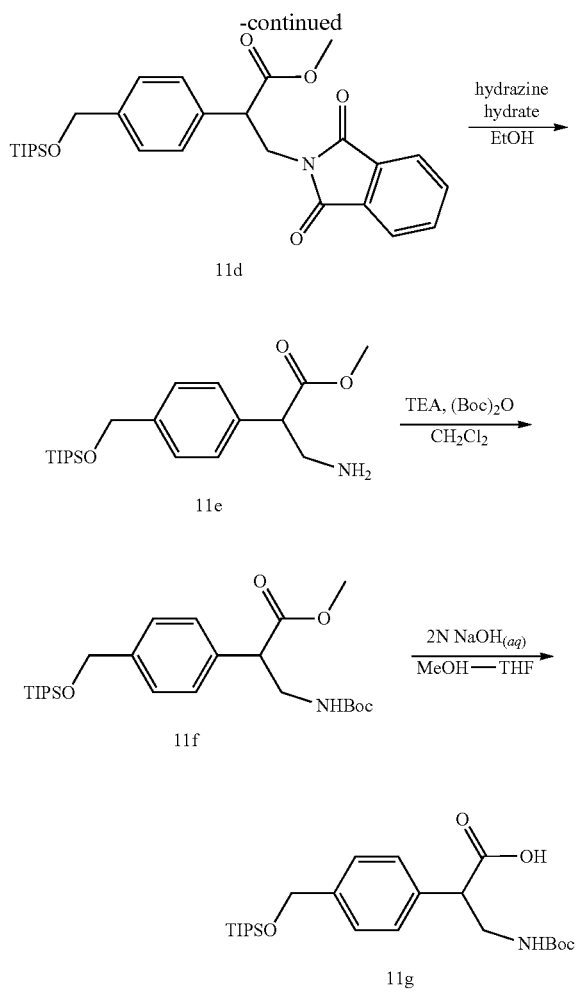

To a zero degree solution of 2-(4-(hydroxymethyl)phenyl)acetic acid (5233 mg, 31.49 mmol) in CH$_2$Cl$_2$ (25 mL) and MeOH (6 mL), TMS diazomethane (23.6 mL of a 2 M solution in hexanes, 47.23 mmol) was added dropwise. After 15 minutes, the reaction was quenched by the addition of HOAc (1 mL). The reaction mentioned above was diluted with EtOAc (100 mL) and washed with saturated NaHCO$_3$ (2×25 mL) and brine (25 mL). The organic layer was dried (Na$_2$SO$_4$), filtered and concentrated. The residue was purified by flash chromatography (0 to 33 percent EtOAc/hexanes) to afforded methyl 2-(4-(hydroxymethyl)phenyl)acetate (11b). $^1$H-NMR (500 MHz, CDCl$_3$): δ: 7.33 (d, J=7.5 Hz, 2H), 7.27 (d, J=7.5 Hz, 2H), 4.68 (s, 2H), 3.69 (s, 3H), 3.63 (s, 2H).

To a zero degree solution of methyl 2-(4-(hydroxymethyl)phenyl)acetate (11b) (5674 mg, 31.49 mmol) in CH$_2$Cl$_2$ (50 mL), 2,6-lutidine (5.47 mL, 47.23 mmol) and TIPS-OTf (14.48 g, 47.23 mmol) were added. The ice bath was removed and the solution was allowed to warm to room temperature and stirred. After 2 hours, the reaction was quenched by the addition of NH$_4$Cl$_{(aq)}$ (50 mL). The reaction was diluted with CH$_2$Cl$_2$ (100 mL) and washed with H$_2$O (2×50 mL) and brine (50 mL). The organic layer was dried (Na$_2$SO$_4$), filtered and concentrated. The residue was purified by flash chromatography (0 to 5 percent EtOAc/hexanes) to afforded methyl 2-(4-(((triisopropylsilyl)oxy)methyl)phenyl)acetate (11c). $^1$H-NMR (500 MHz, CDCl$_3$): δ 7.31 (d, J=8.0 Hz, 2H), 7.24 (d, J=8.0 Hz, 2H), 4.82 (s, 2H), 3.69 (s, 3H), 3.62 (s, 2H), 1.21-1.15 (m, 3H), 1.10-1.06 (m, 18H).

To a −78° C. solution of methyl 2-(4-(((triisopropylsilyl)oxy)methyl)phenyl)acetate (11c) (10.60 g, 31.49 mmol) in THF (50 mL), LiHMDS (47.30 mL, 47.23 mmol) was added dropwise. After 30 minutes, the bromo–methyl phthalimide (11.34 g, 47.23 mmol) in THF (50 mL) was added dropwise at the same temperature. The −78° C. bath was removed and the solution was allowed to warm to room temperature and stirred. After 2 hours, the reaction was quenched by the addition of NH$_4$Cl$_{(aq)}$ (40 mL) and extracted with EtOAc (100 mL). The organic layer was dried (Na$_2$SO$_4$), filtered and concentrated. The residue was purified by flash chromatography (0 to 10 percent EtOAc/hexanes) to afforded methyl 3-(1,3-dioxoisoindolin-2-yl)-2-(4-(((triisopropylsilyl)oxy)methyl)phenyl) propanoate (11d). $^1$H-NMR (500 MHz, CDCl3): δ 7.79-7.76 (m, 2H), 7.69-7.67 (m, 2H), 7.30-7.28 (m, 4H), 4.77 (s, 2H), 4.31 (t, J=7.5 Hz, 1H), 4.26-4.15 (m, 2H), 3.66 (s, 3H), 1.17-1.06 (m, 3H), 1.05-1.02 (m, 18H).

To a stirred solution of methyl 3-(1,3-dioxoisoindolin-2-yl)-2-(4-(((triisopropylsilyl) oxy)methyl)phenyl)propanoate (11d) (4.39 g, 8.86 mmol) in MeOH (30 mL) and EtOH (50 mL), hydrazine hydrate (2.22 g, 44.29 mmol) was added, and the solution was refluxed for 2 hours. The solids were filtered and the solvents were evaporated. The residue was purified by flash chromatography (0 to 50 percent EtOAc/hexanes) to afforded methyl 3-amino-2-(4-(((triisopropylsilyl)oxy)methyl)phenyl)propanoate (11e).

To a stirred solution of methyl 3-amino-2-(4-(((triisopropylsilyl)oxy)methyl) phenyl)propanoate (11e) (3.19 g, 8.74 mmol) in CH$_2$Cl$_2$ (50 mL), TEA (2.44 mL, 17.47 mmol) and (Boc)$_2$O (17.47) were added. The solution was stirred at room temperature for 4 hours, and then poured into CH$_2$Cl$_2$/NaHCO$_{3(aq)}$. The aqueous layers were further extracted with CH$_2$Cl$_2$, dried (Na$_2$SO$_4$), filtered and evaporated. The residue was purified by flash chromatography (0 to 4 percent EtOAc/hexanes) to afforded methyl 3-((tert-butoxycarbonyl)amino)-2-(4-(((triisopropylsilyl)oxy)methyl)phenyl)propanoate (11f). $^1$H-NMR (500 MHz, CDCl$_3$): δ 7.32 (d, J=7.5 Hz, 2H), 7.22 (d, J=7.5 Hz, 2H), 4.86-4.82 (m, 1H), 4.77 (s, 2H), 3.88-3.83 (m, 1H), 3.68 (s, 3H), 3.63-3.57 (m, 1H), 3.51-3.48 (m, 1H), 1.42 (s, 9H), 1.21-1.14 (m, 3H), 1.10-1.08 (m, 18H).

To a solution of methyl 3-((tert-butoxycarbonyl)amino)-2-(4-(((triisopropylsilyl) oxy)methyl)phenyl)propanoate (11f) (2.07 g, 4.44 mmol) in THF/MeOH (1:1, 40 mL), NaOH (8.88 mL, 17.76 mmol) was added, and stirred for 2 hours at room temperature. The mixture was neutralized with 1 N HCl and extracted with EtOAc. The organic layer was washed with brine, dried over Na$_2$SO$_4$ and concentrated. The residue was purified by silica gel column chromatography (eluting solvent: EtOAc/Hexanes=1/3) to give 3-((tert-butoxycarbonyl)amino)-2-(4-(((triisopropylsilyl) oxy)methyl)phenyl)propanoic acid (11g) (1.84 g, 92%), which was a white solid. $^1$H-NMR (500 MHz, CDCl$_3$): δ 7.35 (d, J=7.5 Hz, 2H), 7.28 (d, J=7.5 Hz, 2H), 6.77 (brs, 0.5H), 4.92 (brs, 0.5H), 4.82 (s, 2H), 3.91-3.80 (m, 1H), 3.59-3.50 (m, 2H), 1.46-1.42 (m, 9H), 1.21-1.14 (m, 3H), 1.10-1.08 (m, 18H).

(12) Synthesis Example 12

The synthesis scheme of Compound 11 is shown in the following Scheme 9.

Scheme 9

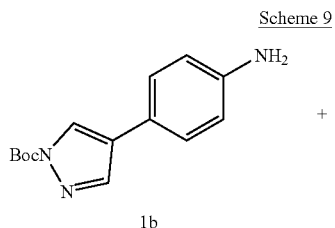

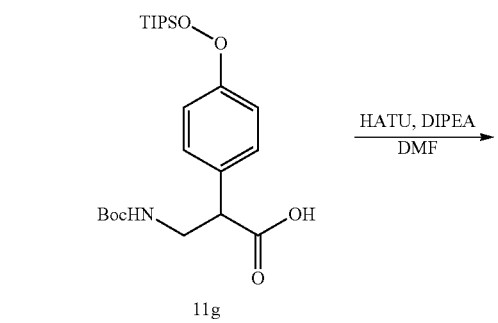

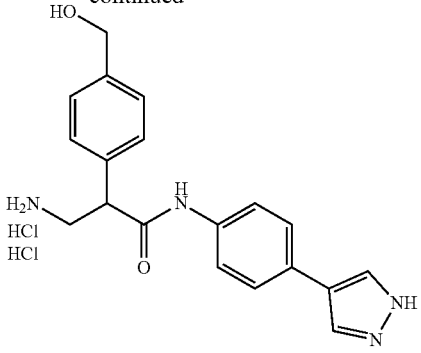

The synthesis method for the final Compound 11 was similar to that for Compound 9.

The compound tert-butyl 4-(4-(3-((tert-butoxycarbonyl)amino)-2-(4-(((triisopropylsilyl)oxy)methyl)phenyl)propanamido)phenyl)-1H-pyrazole-1-carboxylate (11h) was white powder. $^1$H-NMR (500 MHz, CDCl$_3$): δ 8.25 (s, 1H), 7.95 (s, 1H), 7.50 (d, J=7.5 Hz, 2H), 7.45 (d, J=7.5 Hz, 2H), 7.37 (d, J=7.5 Hz, 2H), 7.33-7.31 (m, 3H), 5.15 (brs, 1H), 4.83 (s, 2H), 3.90 (brs, 1H), 3.68 (brs, 1H), 3.58-3.55 (m, 1H), 1.67 (s, 9H), 1.43 (s, 9H), 1.26-1.14 (m, 3H), 1.10-1.08 (m, 18H).

The compound tert-butyl 4-(4-(3-((tert-butoxycarbonyl)amino)-2-(4-(hydroxymethyl)phenyl)propanamido)phenyl)-1H-pyrazole-1-carboxylate (11i) was white powder. $^1$H-NMR (500 MHz, CDCl$_3$): δ 8.25 (s, 1H), 7.94 (s, 1H), 7.51 (d, J=8.0 Hz, 2H), 7.46-7.44 (m, 3H), 7.39-7.37 (m, 4H), 5.15 (brs, 1H), 3.92 (brs, 1H), 3.67-3.66 (m, 1H), 3.56-3.54 (m, 1H), 1.67-1.64 (m, 10H), 1.43 (s, 9H).

The final compound N-(4-(1H-pyrazol-4-yl)phenyl)-3-amino-2-(4-(hydroxymethyl) phenyl)propenamide dihydrochloride (11) was white powder. $^1$H-NMR (500 MHz, D$_2$O) δ: 8.05 (s, 2H), 7.44 (d, J=9.0 Hz, 2H), 7.35 (s, 4H), 7.27 (d, J=9.0 Hz, 2H), 4.53 (s, 2H), 4.08 (t, J=6.5 Hz, 1H), 3.56 (dd, J=6.5, 13.0 Hz, 1H), 3.36 (dd, 13.0 Hz, 1H).

8. Synthesis of Compound 12

(13) Synthesis Example 13

The synthesis scheme of Compound 12 is shown in the following Scheme 10.

Scheme 10

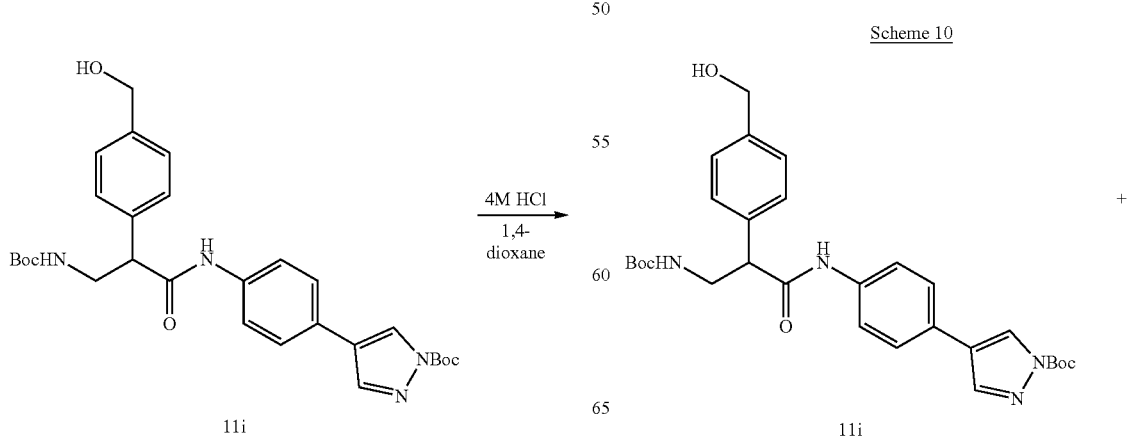

35

-continued

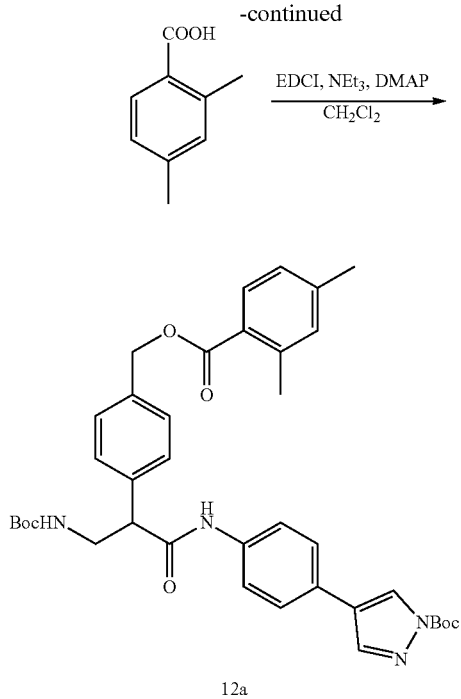

12a

12

The synthesis method for the final Compound 12 was similar to that for Compound 10.

The compound tert-butyl 4-(4-(3-((tert-butoxycarbonyl)amino)-2-(4-(((2,4-dimethylbenzoyl)oxy)methyl)phenyl)propanamido)phenyl)-1H-pyrazole-1-carboxylate (12a) was white powder. ¹H-NMR (CDCl₃, 500 MHz) 8.25 (s, 1H), 7.94 (s, 1H), 7.86 (d, J=7.5 Hz, 1H), 7.52 (d, J=8.0 Hz, 2H), 7.46-7.44 (m, 4H), 7.41-7.37 (m, 3H), 7.06-7.03 (m, 3H), 5.31 (s, 2H), 5.14 (brs, 1H), 3.93 (brs, 1H), 3.68-3.67 (m, 1H), 3.59-3.55 (m, 1H), 2.60 (s, 3H), 2.37 (s, 3H), 1.67 (s, 9H), 1.43 (s, 9H).

The compound 4-(1-((4-(1H-pyrazol-4-yl)phenyl)amino)-3-amino-1-oxopropan-2-yl) benzyl 2,4-dimethylbenzoate dihydrochloride (12) was white powder. ¹H-NMR (500 MHz, DMSO) δ: 10.40 (s, NH, 1H), 8.03 (brs, NH, 3H), 8.00 (s, 2H), 7.75 (d, J=8.0 Hz, 1H), 7.58 (d, J=9.0 Hz, 2H), 7.51 (d, J=9.0 Hz, 2H), 7.47-7.44 (m, 4H), 7.12 (s, 1H), 7.09 (d, J=8.0 Hz, 1H), 5.26 (s, 2H), 4.13 (dd, J=5.5, 9.0 Hz, 1H), 3.07-3.02 (m, 1H), 2.47 (s, 3H), 2.29 (s, 3H).

36

9. Synthesis of Compound 13

(14) Synthesis Example 14

The synthesis scheme of Compound 13 is shown in the following Scheme 11.

Scheme 11

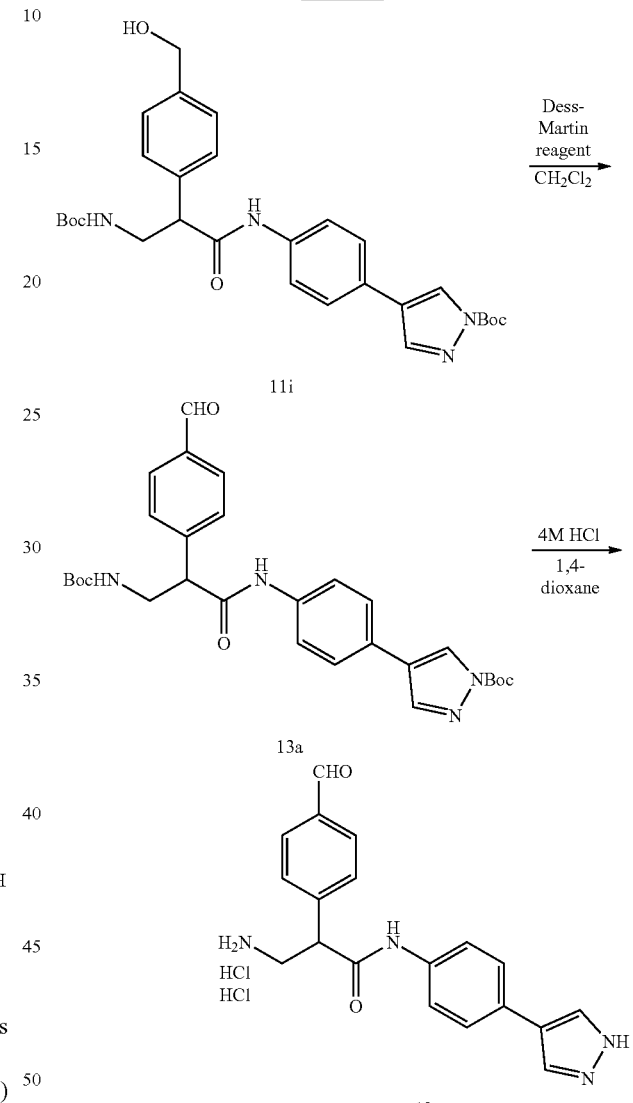

To a stirred solution of tert-butyl 4-(4-(3-((tert-butoxycarbonyl)amino)-2-(4-(hydroxymethyl)phenyl)propanamido)phenyl)-1H-pyrazole-1-carboxylate (11i) (100 mg, 0.19 mmol) in CH₂Cl₂ (10 mL), Dess-Martin reagent (166 mg, 0.37 mmol) was added. The resultant solution was stirred at room temperature for 1 hour. The solvent was evaporated under reduced pressure, and the crude product was purified by column chromatography (EtOAc/Hexanes=25% to 50%) to get tert-butyl 4-(4-(3-((tert-butoxycarbonyl)amino)-2-(4-formylphenyl)propanamido)phenyl)-1H-pyrazole-1-carboxylate (13a) which was white powder. ¹H-NMR (CDCl₃, 500 MHz) 10.01 (s, CHO, 1H), 8.26 (s, 1H), 7.95 (s, 1H), 7.88 (d, J=8.0 Hz, 2H), 7.62 (brs, 1H), 7.58-7.53 (m, 4H), 7.46 (d, J=8.0 Hz, 2H), 5.12 (brs, 1H), 4.13-4.05 (m, 1H), 3.74-3.70 (m, 1H), 3.60-3.56 (m, 1H), 1.66 (s, 9H), 1.43 (s, 9H).

In the 4 mL vial, tert-butyl 4-(4-(3-((tert-butoxycarbonyl) amino)-2-(4-formylphenyl)propanamido)phenyl)-1H-pyrazole-1-carboxylate (13a) (52 mg, 0.10 mmol) and 4 M HCl in dioxane (1.0 mL) was charged. The resulting mixture was stirred at room temperature for 1 hour. The solvent was removed under reduced pressure to give the desired product N-(4-(1H-pyrazol-4-yl)phenyl)-3-amino-2-(4-formylphenyl)propanamide dihydrochloride (13) (44 mg, 90%). $^1$H-NMR (500 MHz, D$_2$O) δ: 9.79 (s, CHO, 1H), 7.94 (s, 2H), 7.84 (d, J=8.5 Hz, 2H), 7.53 (d, J=8.5 Hz, 2H), 7.39 (d, J=8.5 Hz, 2H), 7.25 (d, J=8.5 Hz, 2H), 4.19 (t, J=7.0 Hz, 1H), 3.60 (dd, J=7.0, 12.5 Hz, 1H), 3.38 (dd, 12.5 Hz, 1H).

10. Synthesis of Compound 14

(15) Synthesis Example 15

The synthesis scheme of Compound 14 is shown in the following Scheme 12.

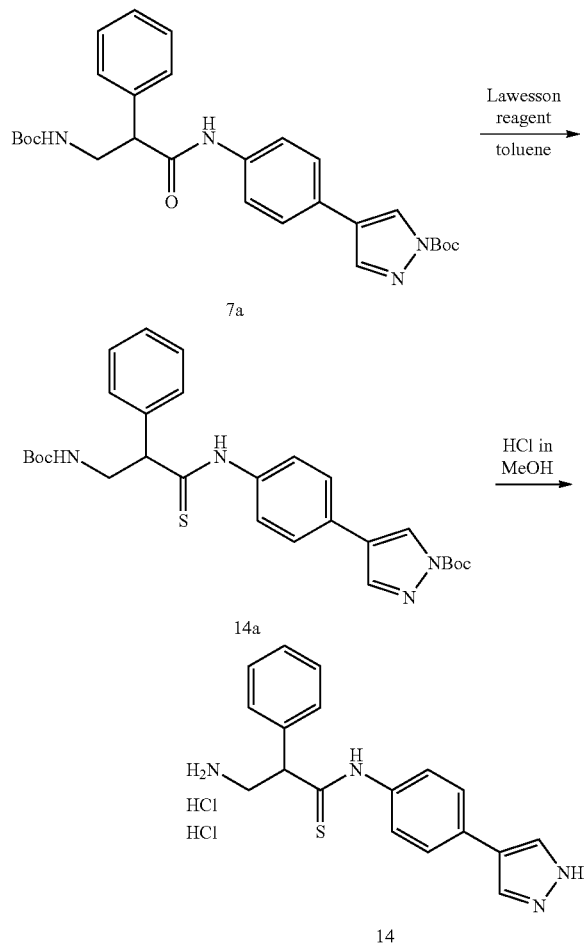

A mixture of tert-butyl 4-(4-(3-((tert-butoxycarbonyl) amino)-2-phenylpropanamido)phenyl)-1H-pyrazole-1-carboxylate (7a) (506 mg, 1.0 mmol, 1.0 equiv) and Lawesson reagent (808 mg, 2.0 mmol, 2.0 equiv) in toluene (5 mL) was heated to 120° C. for 16 hours under N$_2$ atmosphere. The reaction mixture mentioned above was cooled and concentrated to afford the crude compound tert-butyl 4-(4-(3-((tert-butoxycarbonyl) amino)-2-phenylpropanethioamido)phenyl)-1H-pyrazole-1-carboxylate (14a) (520 mg, yield: 100%) which could be used to the next step without further purification. LCMS (ES, m/z): [M+H]+=523.3.

Tert-butyl 4-(4-(3-((tert-butoxycarbonyl)amino)-2-phenylpropanethioamido)phenyl)-1H-pyrazole-1-carboxylate (14a) (520 mg, 1.0 mmol, 1.0 eq) was dissolved in 1 mL MeOH to be added to HCl/MeOH (3 M, 5 mL), and stirred at room temperature for 3 hours. The reaction mixture mentioned above was concentrated. The residue was purified by flash (DCM/MeOH from 100% to 10%) to obtain the crude product (110 mg), and that was crystallized with DCM and MeOH and adjusted pH to 5.0 with 1 N HCl to afford N-(4-(1H-pyrazol-4-yl)phenyl)-3-amino-2-phenylpropanethioamide dihydrochloride (Compound 14) (75 mg, yield: 23% for two steps), which was a yellow solid. LCMS (ES, m/z): [M+H]+=323.2. $^1$H-NMR (400 MHz, DMSO-d$_6$): 12.08 (s, 1H), 8.06-7.99 (m, 5H), 7.77 (d, J=8.4 Hz, 2H), 7.63-7.59 (m, 4H), 7.41-7.31 (m, 3H), 4.54-4.50 (m, 1H), 3.88-3.78 (m, 1H), 3.31-3.24 (m, 1H).

11. Synthesis of Compound 15

(16) Synthesis Example 16

The synthesis scheme of Compound 15 is shown in the following Scheme 13.

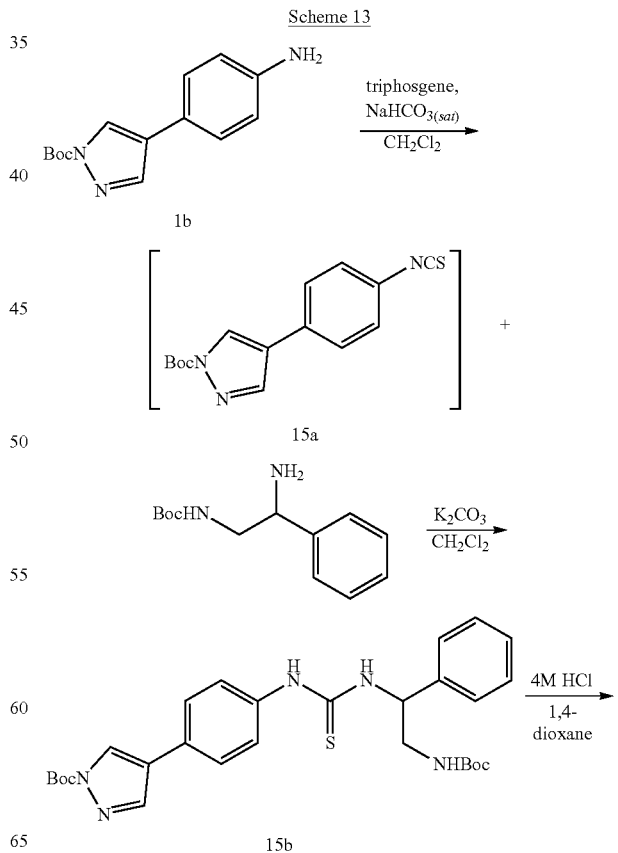

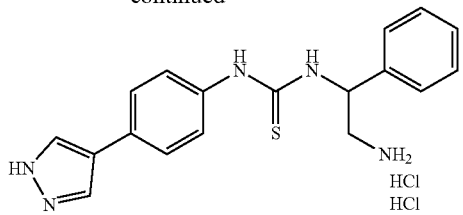

15

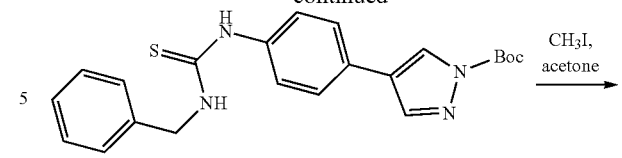

16a

To the solution of tert-butyl-(4-amino-3-(2-(dimethylamino)ethoxy)phenyl)-1H-pyrazole (200 mg, 0.85 mmol, 1.0 eq) in CH$_2$Cl$_2$ (4 mL), a saturated solution of NaHCO$_3$ (2 mL, 0.4M) was added. Next, the thiophosgene (97 mg, 0.85 mmol, 1.0 eq) was added slowly and stirred for 3 hours. The organic layer was dried over anhydrous sodium sulfate and the solvent was removed under reduced pressure to obtain a crude product 15a. In the residue 15a, tert-butyl (2-amino-2-phenylethyl)carbamate (220 mg, 0.85 mmol, 1.0 eq) and K$_2$CO$_3$ (235 mg, 1.70 mmol, 2.0 eq) in CH$_2$Cl$_2$ (4.0 mL) were added. The reaction was workup by water and extracted with CH$_2$Cl$_2$. The organic layer was collected and dried over Na$_2$SO$_4$, the extract solution was condensed under reduced pressure. The residue was purified with silica gel (EtOAc/Hex=20%) to obtain the compound tert-butyl 4-(4-(3-(2-((tert-butoxycarbonyl)amino)-1-phenylethyl)thioureido)phenyl)-1H-pyrazole-1-carboxylate (15b) (353 mg, 85%) which was a pale yellow solid. $^1$H-NMR (500 MHz, CDCl3) δ: 8.30 (s, 1H), 8.02 (s, 1H), 7.98 (s, 1H), 7.63 (s, 1H), 7.57 (d, J=8.0 Hz, 2H), 7.38-7.34 (m, 4H), 7.30-7.24 (m, 3H), 5.63 (s, 1H), 4.85 (s, 1H), 3.55-3.44 (m, 2H), 1.68 (s, 9H), 1.31 (s, 9H).

In the 20 mL vial, the compound tert-butyl 4-(4-(3-(2-((tert-butoxycarbonyl)amino)-1-phenylethyl)thioureido)phenyl)-1H-pyrazole-1-carboxylate (15b) (353 mg, 0.66 mmol) and 4 M HCl in dioxane (3.3 mL) were charged. The resulting mixture was stirred at room temperature for 1 hour. The solvent was removed under reduced pressure to obtain the compound 1-(4-(1H-pyrazol-4-yl)phenyl)-3-(2-amino-1-phenylethyl)thiourea dihydrochloride (15) which presented as pale yellow powder (244 mg, 90%). $^1$H-NMR (500 MHz, CD$_3$OD) δ: 8.56 (brs, 2H), 7.65 (d, J=8.0, 2H), 7.60-7.58 (m, 2H), 7.48-7.39 (m, 4H), 7.38-7.37 (m, 1H), 6.08 (dd, J=9.0, 5.0 Hz, 1H), 3.49 (dd, J=13.0, 9.0 Hz, 1H), 3.36 (dd, J=13.0, 5.0 Hz, 1H).

12. Synthesis of Compound 16

(17) Synthesis Example 17

The synthesis Scheme of Compound 16 is shown in the following Scheme 14.

Scheme 14

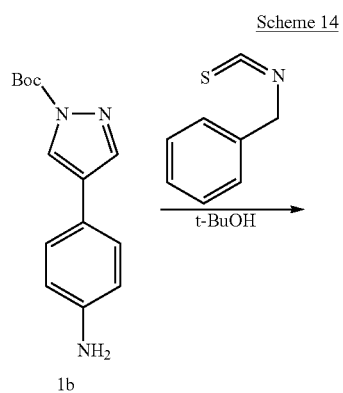

A mixture of tert-butyl 4-(4-aminophenyl)-1H-pyrazole-1-carboxylate (1b) (400 mg, 1.54 mmol, 1.0 equiv) and (isothiocyanatomethyl)benzene (276 mg, 1.85 mmol, 1.2 equiv) in t-BuOH (10 mL) was stirred at 85° C. overnight under N$_2$. The reaction mixture mentioned above was cooled and concentrated. The residue was purified by silica gel column and eluted with ethyl acetate/petroleum ether (1:1) to afford tert-butyl 4-(4-(3-benzylthioureido)phenyl)-1H-pyrazole-1-carboxylate (16a) (410 mg, yield: 65%), which was a yellow solid. LCMS (ES, m/z): [M+H]$^+$=409.3.

A mixture of tert-butyl 4-(4-(3-benzylthioureido)phenyl)-1H-pyrazole-1-carboxylate (16a) (410 mg, 1.00 mmol, 1.0 equiv) and CH$_3$I (214 mg, 1.51 mmol, 1.5 equiv) in acetone (15 mL) was stirred at 30° C. for 3 hours under N$_2$. The reaction mixture mentioned above was filtered. The filter cake was collected to afford tert-butyl 4-(4-(((benzylamino)(methylthio)methylene)amino)phenyl)-1H-pyrazole-1-carboxylate (16b) (370 mg, yield: 87%) as a white solid. LCMS (ES, m/z): [M+H]$^+$=423.3.

A mixture of tert-butyl 4-(4-(((benzylamino)(methylthio)methylene)amino)phenyl)-1H-pyrazole-1-carboxylate (16b) (370 mg, 0.88 mmol, 1.0 equiv), cyanamide (110 mg, 2.63 mmol, 3.0 equiv) and 1,4-diazabicyclo[2.2.2]octane (98 mg, 0.88 mmol, 1.0 equiv) in t-BuOH (10 mL) was stirred at 90° C. overnight under N$_2$ and then stirred at 130° C. for 3 hours. The reaction mixture mentioned above was cooled and concentrated. The residue was treated with dichloromethane (10 mL) and filtered. The filtered cake was purified by Prep-HPLC (H$_2$O: CH$_3$CN=7:3) to afford 1-(4-(1H-pyrazol-4-yl)phenyl)-3-benzyl-2-cyanoguanidine hydrochloride (16) (53 mg, yield: 19%), which was a white solid. LCMS (ES, m/z): [M+H]$^+$=317.2 $^1$H-NMR (400 MHz, DMSO-d$_6$): 9.08 (s, 1H), 8.03 (s, 2H), 7.64-7.62 (m, 1H), 7.57 (d, J=8.4 Hz, 2H), 7.32 (t, J=7.4 Hz, 2H), 7.28-7.23 (m, 3H), 7.17 (d, J=8.8 Hz, 2H), 4.36 (d, J=5.6 Hz, 2H).

13. Synthesis of Compound 17

(18) Synthesis Example 18

The synthesis scheme of Compound 17 is shown in the following Scheme 15.

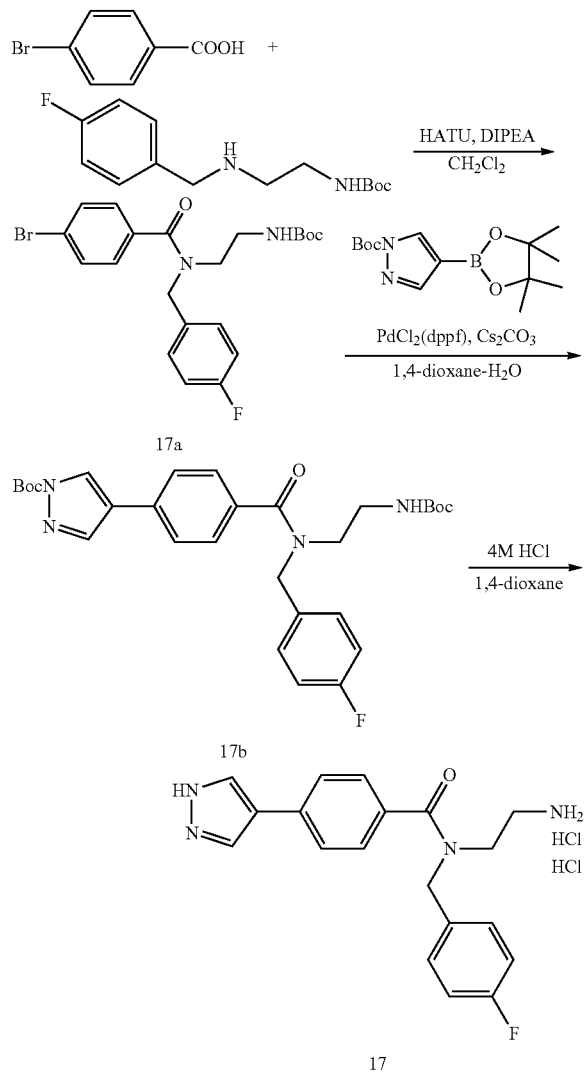

To a stirred solution of 4-bromobenzoic acid (322 mg, 1.60 mmol) and tert-butyl (2-((4-fluorobenzyl)amino)ethyl) carbamate (430 mg, 1.60 mmol) in CH$_2$Cl$_2$ (5 mL), DIPEA (698 μL, 4.01 mmol) and HATU (732 mg, 1.92 mmol) were added. The reaction mixture mentioned above was stirred at room temperature for 2 hours. The solvent was removed by reduced pressure, and the residue was purified by column chromatography to afford tert-butyl (2-(4-bromo-N-(4-fluorobenzyl)benzamido)ethyl)carbamate (17a) (537 mg, 75%) as oil. $^1$H-NMR (CDCl$_3$, 500 MHz) 7.53 (s, 1H), 7.31-7.29 (m, 2H), 7.10-7.04 (m, 4H), 5.01-4.75 (m, 1H), 4.53 (s, 2H), 3.58-3.19 (m, 4H), 1.44 (s, 9H).

A mixture of tert-butyl (2-(4-bromo-N-(4-fluorobenzyl)benzamido)ethyl)carbamate (17a) (537 mg, 1.19 mmol), tert-butyl 4-(4,4,5,5-tetramethyl-1,3,2-dioxaborolan-2-yl)-1H-pyrazole-1-carboxylate (350 mg, 1.19 mmol), PdCl$_2$(dppf) (87 mg, 0.12 mmol) and Cs$_2$CO$_3$ (775 mg, 2.38 mmol) was added in a sealed tube, a mixed solvent (dioxane/H$_2$O=10/1, 6 mL) was then injected thereto under argon, and the mixture was stirred at 90° C. for 2 hours. After cooling to room temperature, the solvent was removed by rotary evaporation, and the residue was added with water and extracted with EtOAc (15 mL×3). The combined organic layers were washed with brine, dried over anhydrous Na$_2$SO$_4$ and filtered. The filtrate was concentrated and the residue was purified by flash chromatography on silica gel (EtOAc/Hex=25% to 67%) to give tert-butyl 4-(4-((2-((tert-butoxycarbonyl)amino)ethyl)(4-fluorobenzyl)carbamoyl) phenyl)-1H-pyrazole-1-carboxylate (17b) which was white powder (385 mg, 60%). $^1$H-NMR (CDCl3, 500 MHz) 8.32 (s, 1H), 7.59 (s, 1H), 7.53 (s, 1H), 7.47 (s, 2H), 7.14-7.04 (m, 4H), 5.07-4.78 (m, 1H), 4.58 (s, 2H), 3.60-3.33 (m, 4H), 1.68 (s, 9H), 1.45 (s, 9H).

To a mixture of tert-butyl 4-(4-((2-((tert-butoxycarbonyl)amino)ethyl)(4-fluorobenzyl)carbamoyl)phenyl)-1H-pyrazole-1-carboxylate (17b) (300 mg, 0.56 mmol) and 1,4-dioxane (1 mL), 4 M HCl in 1,4-dioxane (2.78 mL) was added. The reaction mixture mentioned above was stirred at room temperature for 1 hour. The reaction mixture was concentrated. The residue was treated with DCM (6 mL) and filtered. The filtered cake was collected to afford N-(2-aminoethyl)-N-(4-fluorobenzyl)-4-(1H-pyrazol-4-yl)benzamide dihydrochloride (17) (200 mg, 87%) which was a pale yellow solid. $^1$H-NMR (500 MHz, D$_2$O) δ: 7.99 (s, 2H), 7.40-7.32 (m, 4H), 7.04-6.97 (m, 4H), 4.41 (s, 2H), 3.64 (s, 2H), 3.06 (s, 2H).

14. Synthesis of Compound 18

(19) Synthesis Example 19

The synthesis scheme of Compound 18 is shown in the following Scheme 16.

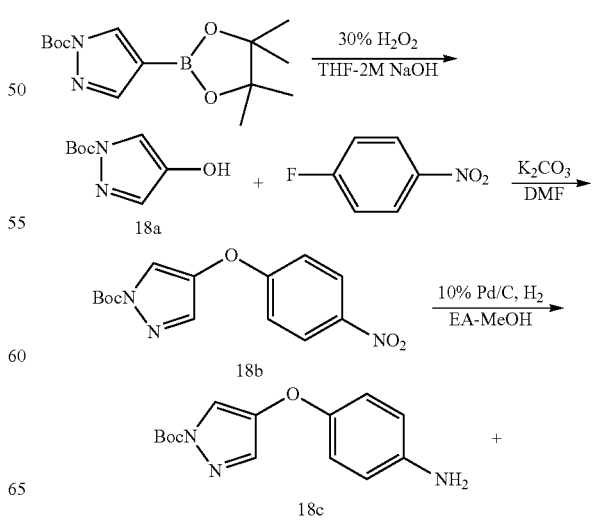

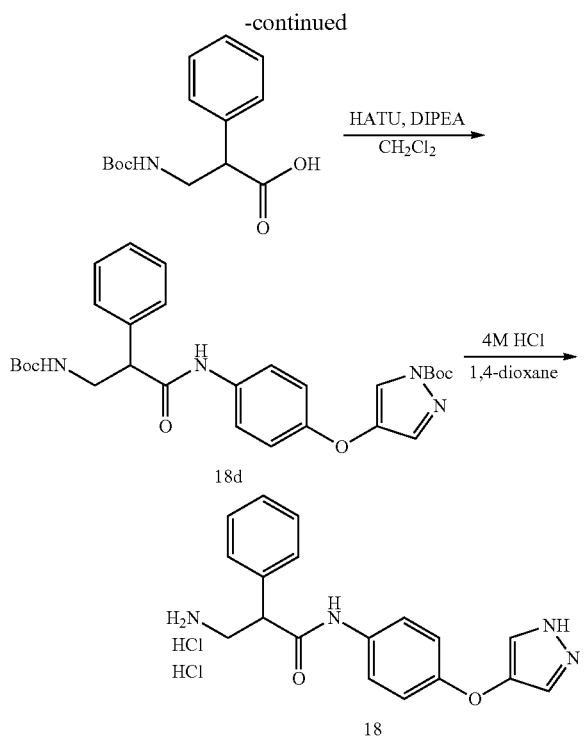

To a stirred solution of tert-butyl 4-(4,4,5,5-tetramethyl-1,3,2-dioxaborolan-2-yl)-1H-pyrazole-1-carboxylate (1540 mg, 5.24 mmol) in THF (15 mL) at 0° C., 2 M NaOH$_{(aq)}$ (5.24 mL, 10.47 mmol) was added, and then 30% hydrogen peroxide (1.19 mL, 10.47 mmol) was added. The reaction mixture mentioned above was stirred at 0° C. for 30 minutes and then room temperature for 1 hour. The reaction mixture was cooled to 0° C. and diluted with DCM, and 2 M HCl$_{(aq)}$ was added thereto till pH 2 was reached. The organic layer were collected and dried, and the solvent was removed under reduced pressure to give tert-butyl 4-hydroxy-1H-pyrazole-1-carboxylate (18a) (965 mg, 100%) which was a yellow solid. $^1$H-NMR (500 MHz, CDCl$_3$) δ: 9.28 (s, OH, 1H), 7.51 (s, 1H), 7.45 (s, 1H), 1.52 (s, 9H).

To a stirred solution of tert-butyl 4-hydroxy-1H-pyrazole-1-carboxylate (18a) (965 mg, 5.24 mmol) and 1-fluoro-4-nitrobenzene (739 mg, 5.24) in DMF (10 mL), K$_2$CO$_3$ (1447 mg, 10.47 mmol) was added. The reaction mixture mentioned above was stirred at 90° C. for 12 hours. The solvent was removed under reduced pressure, and the residue was purified by column chromatography (EtOAc/Hexane=10%) to give tert-butyl 4-(4-nitrophenoxy)-1H-pyrazole-1-carboxylate (18b) (479 mg, 30%) which was a yellow solid. $^1$H-NMR (500 MHz, CDCl3) δ: 8.22 (d, J=8.0 Hz, 2H), 8.01 (s, 1H), 7.65 (s, 1H), 7.10 (d, J=8.0 Hz, 2H), 1.67 (s, 9H).

To a solution of tert-butyl 4-(4-nitrophenoxy)-1H-pyrazole-1-carboxylate (18b) (140 mg, 0.46 mmol) in MeOH (5 mL) and EtOAc (5 mL), 10% Pd/C (49 mg, 0.046 mmol) was added. The reaction mixture mentioned above was stirred at room temperature under H$_2$ balloon atmosphere for 2 hours. The mixture was filtered, and the filtrate was evaporated by rotary evaporation to give tert-butyl 4-(4-aminophenoxy)-1H-pyrazole-1-carboxylate (18c) (118 mg, 93%) which was a brown solid.

To a stirred solution of 3-((tert-butoxycarbonyl)amino)-2-phenylpropanoic acid (114 mg, 0.43 mmol) and tert-butyl 4-(4-aminophenoxy)-1H-pyrazole-1-carboxylate (118 mg, 0.43 mmol) in CH$_2$Cl$_2$ (5 mL), DIPEA (187 μL, 1.07 mmol) and HATU (196 mg, 0.51 mmol) were added. The reaction mixture mentioned above was stirred at room temperature for 2 hours. The solvent was removed by reduced pressure, then the residue was purified with preparative reverse HPLC (80% ACN, 20% H$_2$O), and then lyophilized to get tert-butyl 4-(4-(3-((tert-butoxycarbonyl)amino)-2-phenylpropanamido)phenoxy)-1H-pyrazole-1-carboxylate (18d) (110 mg, 49%) which was white powder. $^1$H-NMR (500 MHz, CDCl$_3$) δ: 7.79 (s, 1H), 7.56 (s, 1H), 7.42 (d, =8.0 Hz, 2H), 7.39-7.29 (m, 5H), 6.98 (d, J=8.0 Hz, 2H), 5.15 (brs, 1H), 3.89 (t, J=5.0 Hz, 1H), 3.70-3.58 (m, 1H), 3.56-3.54 (m, 1H), 1.64 (s, 9H), 1.51 (s, 9H).

To a mixture of tert-butyl 4-(4-(3-((tert-butoxycarbonyl)amino)-2-phenylpropanamido)phenoxy)-1H-pyrazole-1-carboxylate (18d) (110 mg, 0.21 mmol) and 1,4-dioxane (1 mL), 4 M HCl in 1,4-dioxane (1.05 mL) was added. The reaction mixture mentioned above was stirred at room temperature for 1 hour. The reaction mixture was concentrated. The residue was treated with DCM (5 mL) and filtered. The filtered cake was collected to afford N-(4-((1H-pyrazol-4-yl)oxy)phenyl)-3-amino-2-phenylpropanamide dihydrochloride (18) (82 mg, 22%) which was white solid. $^1$H-NMR (500 MHz, CD$_3$OD) δ: 7.84 (s, 2H), 7.54 (d, J=8.5 Hz, 2H), 7.53-7.40 (m, 4H), 7.37-7.34 (m, 1H), 7.02 (d, J=8.5 Hz, 2H), 4.13-4.10 (m, 1H), 3.62-3.57 (m, 1H), 3.24 (dd, 12.5 Hz, 1H).

15. Synthesis of Compound 19

(20) Synthesis Example 20

The synthesis scheme of Compound 19 is shown in the following Scheme 17.

Scheme 17

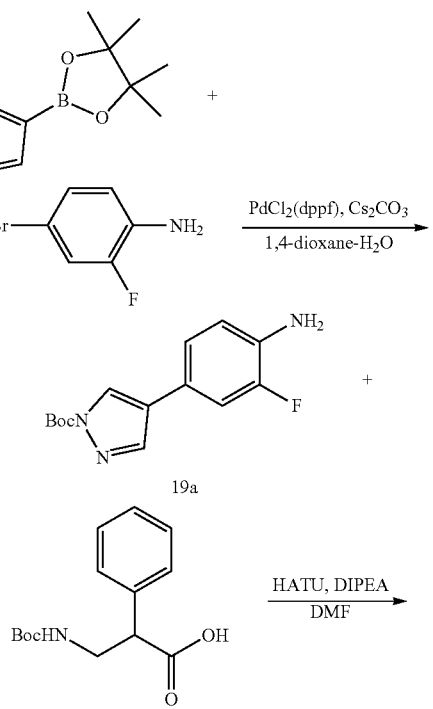

-continued

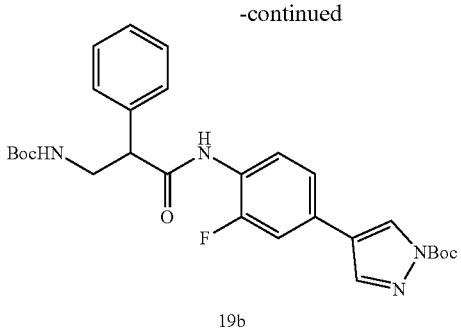

19b

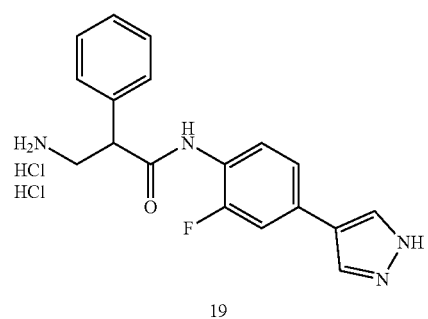

19

To a mixture of 4-bromo-2-fluoroaniline (1211 mg, 6.37 mmol), 1-Boc-4-pyrazoleboronic acid pinacol ester (1875 mg, 6.37 mmol), PdCl$_2$(dppf) (467 mg, 0.64 mmol) and Cs$_2$CO$_3$ (4153 mg, 12.75 mmol) in a sealed tube, a mixed solvent (dioxane/H$_2$O=9/1, 36 mL) was injected under argon, and then the mixture was stirred at 80° C. for 2 hours. After cooling to room temperature, the solvent was removed by rotary evaporation, and the residue was added with water and extracted with EtOAc (30 mL×3). The combined organic layers were washed with brine, dried over anhydrous Na$_2$SO$_4$ and filtered. The filtrate was concentrated, and the residue was purified by flash chromatography on silica gel (EtOAc/Hex=5% to 17%) to give tert-butyl 4-(4-amino-3-fluorophenyl)-1H-pyrazole-1-carboxylate (19a) which was oil (1362 mg, 77%). $^1$H-NMR (500 MHz, CDCl$_3$) δ: 8.17 (s, 1H), 7.89 (s, 1H), 7.15 (dd, J=2.0, 12.0 Hz, 1H), 7.11 (d, J=8.0 Hz, 1H), 6.80 (t, J=8.0 Hz, 1H), 1.67 (s, 9H).

To a stirred solution of 3-((tert-butoxycarbonyl)amino)-2-phenylpropanoic acid (346 mg, 1.31 mmol) and tert-butyl 4-(4-amino-3-fluorophenyl)-1H-pyrazole-1-carboxylate (19a) (362 mg, 1.31 mmol) in DMF (2 mL), DIPEA (569 μL, 3.26 mmol) and HATU (596 mg, 1.57 mmol) were added. The reaction mixture mentioned above was stirred at room temperature for 2 hours. The solvent was removed by reduced pressure, then the residue was purified with preparative reverse HPLC (80% ACN, 20% H$_2$O), and then lyophilized to get tert-butyl 4-(4-(3-((tert-butoxycarbonyl)amino)-2-phenylpropanamido)-3-fluorophenyl)-1H-pyrazole-1-carboxylate (19b) (321 mg, 47%) which was white powder. $^1$H-NMR (500 MHz, CDCl$_3$) δ: 8.32 (t, J=8.5 Hz, 1H), 8.25 (s, 1H), 7.92 (s, 1H), 7.42-7.33 (m, 5H), 7.29-7.26 (m, 1H), 7.19 (d, J=11.5 Hz, 1H), 5.12 (brs, 1H), 3.96 (s, 1H), 3.71-3.68 (m, 1H), 3.60-3.58 (m, 1H), 1.67 (s, 9H), 1.43 (s, 9H).

To tert-butyl 4-(4-(3-((tert-butoxycarbonyl)amino)-2-phenylpropanamido)-3-fluorophenyl)-1H-pyrazole-1-carboxylate (19b) (315 mg, 0.60 mmol) dissolved in 1,4-dioxane (1 mL), 4 M HCl in 1,4-dioxane (4.0 mL) was added. The reaction mixture mentioned above was sonicated at room temperature for 30 minutes. The white powder was collected by filtration, and that was washed with DCM and dried to afford 3-amino-N-(2-fluoro-4-(1H-pyrazol-4-yl)phenyl)-2-phenylpropanamide dihydrochloride (19) (230 mg, 96%). $^1$H-NMR (500 MHz, D$_2$O) δ: 8.05 (s, 2H), 7.42-7.38 (m, 6H), 7.28 (t, J=8.0 Hz, 2H), 4.18 (t, J=7.0 Hz, 1H), 3.58 (dd, J=7.0, 13.0 Hz, 1H), 3.39 (dd, J=7.0, 13.0 Hz, 1H). LCMS (ES, m/z): [M-2HCl+H]$^+$=326.1, [M-2HCl+Na]$^+$=348.1.

16. Synthesis of Compound 20 and Compound 21

(21) Synthesis Example 21

The synthesis scheme of Compound 20 and Compound 21 is shown in the following Scheme 18.

Scheme 18

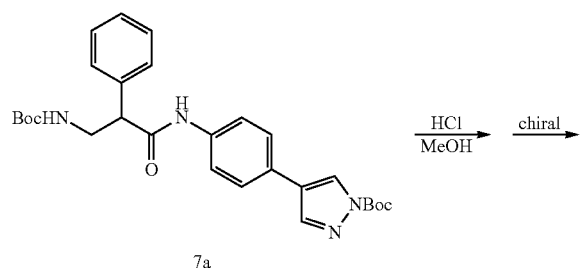

7a

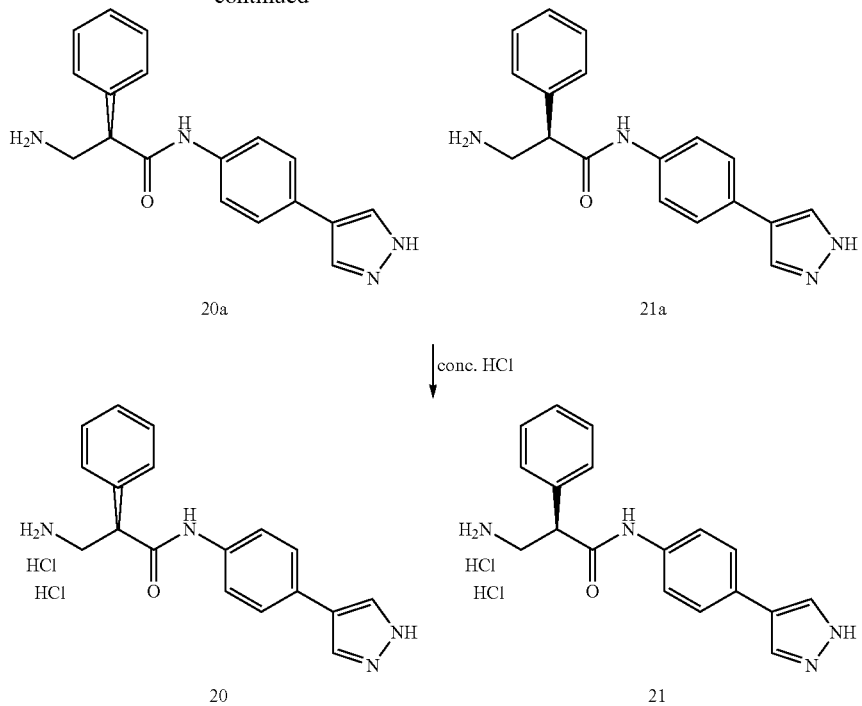

To a solution of tert-butyl 4-(4-(3-((tert-butoxycarbonyl)amino)-2-phenylpropanamido)phenyl)-1H-pyrazole-1-carboxylate (15 g, 29.6 mmol, 1.0 eq) in MeOH (150 mL), HCl/MeOH (150 mL) was added. The mixture mentioned above was stirred at room temperature overnight. The mixture was concentrated and the residue was dissolved in $H_2O$ (50 mL), adjusted pH to 9 with $NaHCO_3$ aqueous solution. The mixture was filtered, and the filtrated cake was dried in vacuo to obtain N-(4-(1H-pyrazol-4-yl)phenyl)-3-amino-2-phenylpropanamide (10 g, 100%) which was a white solid. The solid was purified by chiral resolution to obtain (S)—N-(4-(1H-pyrazol-4-yl)phenyl)-3-amino-2-phenylpropanamide (20a) and (R)—N-(4-(1H-pyrazol-4-yl)phenyl)-3-amino-2-phenylpropanamide (21a).

Separation Condition:
Column: ChiralPak AD-H Daicel chemical Industries, Ltd, 250*30 mm I.D., 10 μm
Mobile phase A: Supercritical $CO_2$; Mobile phase B: MeOH (0.1% $NH_3H_2O$)
A:B=60:40 at 50 mL/minute
Column Temp: 38° C.
Nozzle Pressure: 100 Bar; Nozzle Temperature: 60° C.; Evaporator Temperature: 20° C.; Trimmer Temperature: 25° C.; Wavelength: 220 nm To a solution of (S)—N-(4-(1H-pyrazol-4-yl)phenyl)-3-amino-2-phenylpropanamide in $H_2O$ (10 mL), concentrated HCl (2 mL) was added, and the mixture was concentrated to obtain (S)—N-(4-(1H-pyrazol-4-yl)phenyl)-3-amino-2-phenylpropanamide dihydrochloride (20) (2.1 g). $^1$H-NMR (400 MHz, DMSO-$d_6$): 10.55 (s, 1H), 8.20 (s, 3H), 8.13 (s, 2H), 7.65-7.29 (m, 9H), 4.22-4.19 (m, 1H), 3.51 (s, 1H), 3.04-3.01 (m, 1H) LCMS: $[M+H]^+$=307.1.

To a solution of (R)—N-(4-(1H-pyrazol-4-yl)phenyl)-3-amino-2-phenylpropanamide in $H_2O$ (10 mL) concentrated HCl (2 mL) was added, and the mixture was concentrated to obtain (R)—N-(4-(1H-pyrazol-4-yl)phenyl)-3-amino-2-phenylpropanamide dihydrochloride (21) (2.1 g). $^1$H-NMR (400 MHz, DMSO-d6): 10.50 (s, 1H), 8.16 (s, 3H), 8.11 (s, 2H), 7.64-7.29 (m, 9H), 4.20-4.16 (m, 1H), 3.53-3.48 (m, 1H), 3.06-3.00 (m, 1H). LCMS: $[M+H]^+$=307.1.

Example 2

In Vitro Effect Assay
A. Assay for Inhibitory Effect on Rho-Associated Protein Kinase (ROCK)
Inhibitory effect of each compound synthesized above on Rho-associated protein kinase (ROCK) was tested.
A-1. Method
1. 10 mM test compound was diluted to 1 mM with DMSO, and then further diluted to 300 nM. Netarsudil (AR-13324) is a commercial drug for decreasing intraocular pressure, and AR-13503 is an active metabolite of AR-13324.
2. The 300 nM test compound mentioned above was serially diluted to obtain test compounds with concentrations of 100 nM, 33 nM, 11 nM, 3.7 nM, 1.2 nM and 0.4 nM, respectively.
3. 1 μL of the serially diluted test compound mentioned above was added to 49 μL of the modified ROCK reaction buffer (0.05 M Trizma® hydrochloride buffer (pH 7.5) containing 0.1 M KCl, 0.01 M $MgCl_2$, 0.1 mM EGTA and 2.25 μg/mL ROCK1) to obtain an experimental group sample. 1 μL of DMSO was taken to add to 49 μL of an adjusted ROCK reaction buffer to obtain a positive control group sample (maximum value=100%). 1 μL of DMSO was taken to add to 49 μL of a buffer (0.05 M Trizma® hydrochloride buffer (pH 7.5) containing 0.1 M KCl, 0.01 M $MgCl_2$ and 0.1 mM EGTA) to obtain a vehicle control group sample (minimum value=0%).
4. 20 μL of the above prepared sample was added to a flat-bottomed 96-well plate, and 20 μL ROCK ATP buffer was added to each well.

5. The 96-well plate mentioned above was placed on an orbital shaker and reacted at room temperature for 90 minutes.

6. Next, 40 μL of Kinase-Glo luminescent kinase assay solution (Promega, RV6712) was added to the 96-well plate mentioned above, and the 96-well plate was placed on an orbital shaker and reacted at room temperature for 10 minutes.

7. The luminescence value of each well of the 96-well plate was determined by SpectraMax M5 microplate reader, and the ROCK inhibition rate (%) was calculated by the following formula.

Maximum value=The value measured using the above method in the absence of any test compound (The value measured under the condition of that the enzyme and the substrate were completely reacted was the maximum value)

Minimum value=The value measured using the above method in the absence of enzyme (The value measured under no reaction of enzyme and substrate was the minimum value)

Inhibition rate (%)=(Experimental group (the value measured under the condition of that the test compound was added)−Minimum value)/(Maximum value−Minimum value)*100%

A-2. Results

The results are shown in Table 2.

TABLE 2

| Compound | ROCK1 IC$_{50}$(nM) |
|---|---|
| AR-13324 | +++++ |
| AR-13503 (an active metabolite of AR-13324) | ++++++ |
| Compound 1 | +++ |
| Compound 2 | ++++ |
| Compound 3 | +++ |
| Compound 4 | +++++ |
| Compound 5 | +++++ |
| Compound 6 | ++++ |
| Compound 7 | +++++ |
| Compound 8 | +++++ |
| Compound 9 | +++++ |
| Compound 10 | +++ |
| Compound 11 | +++++ |
| Compound 12 | ++++ |
| Compound 13 | ++++++ |
| Compound 14 | +++++ |
| Compound 15 | +++ |
| Compound 16 | + |
| Compound 17 | +++ |
| Compound 18 | + |
| Compound 19 | ++++ |
| Compound 20 | +++++ |
| Compound 21 | +++ |

Note:
++++++ represents IC$_{50}$ < 1 nM;
+++++ represents IC$_{50}$ = 1-10 nM;
++++ represents IC$_{50}$ = 10~100 nM;
+++ represents IC$_{50}$ = 100-1000 nM;
++ represents IC$_{50}$ > 1,000 nM;
+ represents IC$_{50}$ > 10,000 nM.

B. Assay for Inhibitory Effect on Myosin Light Chain Kinase 4 (MYLK-4)

The experimental procedure referred to the LanthaScreen Eu Kinase Binding Assay Screening Protocol and Assay Conditions provided by ThermoFisher Scientific.

B-1. Material Preparation 3-fold serial dilution was performed on the test compound stock solution (1 mM) prepared in 100% DMSO was for 10 times for ready to use to determine the IC$_{50}$ of the test compound on MYLK-4.

Kinase/Antibody Mixture was pre-diluted with Kinase Buffer to 2× working concentration.

B-2. Analytical Method 1. 3.84 μL of kinase buffer was added to a white 384-well flat plate (Greiner, Cat. NO. 784207), then 8.0 μL of the kinase/antibody mixture mentioned above was added thereto, and then 4.0 μL of the tracer (AlexaFluor labeled Tracer) was added thereto, and after that 160 nL of the above diluted test compound at an appropriate concentration was added thereto, and the culture plate was shaken for 30 seconds.

2. Next, the culture plate was placed at room temperature and incubated for 60 minutes, and then the data was read and analyzed with a fluorescence plate reader. The emission ratio of the reaction liquid in each hole was calculated by using the following formula.

Emission ratio (ER)=AF647 Emission (665 nm)/Europium emission (615 nm)

In addition, a control group for the binding analysis of LanthaScreen Eu kinase was also set up in the analysis mentioned above: Inhinitoin 0% control (0% displacement control): the reaction of which contained no known inhibitor, and was used as the maximum emission ratio; Inhinitoin 100% control (100% displacement control): which contained a known inhibitor with highest concentration, and was used as the minimum emission ratio; wherein the known inhibitor was Sunitinib.

The reaction components of the binding analysis of LanthaScreen Eu Kinase are shown in Table 3. The IC$_{50}$ of the known inhibitor, sunitinib, was 19.0 nM, which was in line with the expected IC$_{50}$ range.

TABLE 3

The reaction components of LanthaScreen Eu kinase binding analysis

| Reaction components | Concentration (nM)/IC$_{50}$ (nM) |
|---|---|
| Kinase (MYLK4) | 5 |
| Antibody (Eu-anti-GST) | 2 |
| Tracer (Tracer 222) | 100 (Kd was 173 nM) |
| Buffer A (containing HEPES, BRIJ-35, MgCl$_2$ and EGTA) | 50 mM HEPES (pH 7.5), 0.01% BRIJ-35, 10 mM MgCl$_2$ and 1 mM EGTA |

3. The inhibition rate of the test compound at different concentrations on MYLK-4 could be obtained according to the following formula:

Inhibition %=[(ER$_{Inhibitoin\ 0\%\ control}$−ER$_{Sample}$)/(ER$_{Inhibitoin\ 0\%\ control}$−ER$_{Inhibitoin\ 100\%\ control}$)]*100

4. IC$_{50}$ of the test compound on MYLK-4 was calculated by the above determined inhibition rates of the test compound at different concentrations on MYLK-4.

B-3. Results

The results are shown in Table 4.

TABLE 4

IC$_{50}$ of the test compound on MYLK-4

| Compound | MYLK4 IC$_{50}$(nM) |
|---|---|
| AR-13324 | ++ |
| AR-13503 | +++ |
| Compound 1 | +++ |
| Compound 2 | +++ |
| Compound 5 | +++ |
| Compound 6 | +++ |
| Compound 7 | ++++ |

TABLE 4-continued

IC$_{50}$ of the test compound on MYLK-4

| Compound | MYLK4 IC$_{50}$(nM) |
|---|---|
| Compound 8 | ++++ |
| Compound 10 | ++ |
| Compound 11 | +++ |
| Compound 12 | +++ |
| Compound 13 | +++ |
| Compound 14 | +++ |
| Compound 15 | +++ |
| Compound 16 | + |
| Compound 17 | + |
| Compound 19 | +++ |
| Compound 20 | ++++ |
| Compound 21 | +++ |

Note:
++++++ represents IC$_{50}$ < 1 nM;
+++++ represents IC$_{50}$ = 1-10 nM;
++++ represents IC$_{50}$ = 10-100 nM;
+++ represents IC$_{50}$ = 100-1000 nM;
++ represents IC$_{50}$ > 1,000 nM;
+ represents IC$_{50}$ > 10,000 nM.

C. Assay for Inhibitory Effect on YSK-4

The experimental procedure referred to the Z'-LYTE Screening Protocol and Assay Conditions provided by ThermoFisher Scientific.

C-1. Material Preparation 3-fold serial dilution was performed on the test compound stock solution (1 mM) prepared in 100% DMSO was for 10 times for ready to use to determine the IC$_{50}$ of the test compound on YSK-4.

Peptide/Kinase Mixture was pre-diluted with Kinase Buffer to 2× working concentration.

ATP solution was pre-diluted with Kinase Buffer (50 mM HEPES pH 7.5, 0.01% BRIJ-35, 10 mM MgCl$_2$, 1 mM EGTA) to 4× working concentration.

The development reagent solution is Novel PKC Lipid Mix, which contains 2 mg/mL Phosphatidyl Serine, 0.2 mg/mL DAG in 20 mM HEPES, pH 7.4 and 0.3% CHAPS, and was pre-diluted 10 fold with development buffer.

C-2. Analytical Method 1. 100 nL of the above diluted test compound and 2.4 μL of kinase buffer were added to a black 384-well plate (Corning, Cat. NO. 4514), then add 5 μL of the peptide/kinase mixture mentioned above was added thereto, and after that 2.5 μL of ATP solution was added thereto, and the culture plate was shaken for 30 seconds.

2. Next, the culture plate was placed at room temperature and incubated for 60 minutes.

3. After that 5 μL of the development reagent solution was added and the culture plate was shaken for 30 seconds in the dark, and then the data was read and analyzed with a fluorescence plate reader.

In addition, for the kinase, the following control group was prepared and placed on the same culture plate as the kinase:

(1) 0% Phosphorylation Control (100% Inhibition Control)

The maximum Emission Ratio is established by the 0% Phosphorylation Control (100% Inhibition Control), which contains no ATP and therefore exhibits no kinase activity. This control yields 100% cleaved peptide in the Development Reaction.

(2) 100% Phosphorylation Control

A synthetically phosphorylated peptide of the same sequence as the peptide substrate is used as the 100% Phosphorylation Control. This control yields a very low percentage of cleaved peptide in the Development Reaction.

The Phosphorylation percent achieved in a specific reaction well (Experimental group) was calculated based on the 0% Phosphorylation Control and 100% Phosphorylation Control.

The Z'-LYTE substrate used in the binding analysis reaction for Z'-LYTE Screening Kinase was Ser/Thr 07 peptide, and ATP reaction concentration was 5 μM (Km of YSK4). The known inhibitor used as a control in this analysis was Staurosporine. The IC$_{50}$ in the system was 12.7 nM, which was in line with the expected IC$_{50}$ range. The inhibition rate of the test compound on YSK-4 at different concentrations was calculated based on the measured value of each hole according to the formula below, and IC$_{50}$ of the test compound on YSK-4 was calculated thereby.

Correction for Background Fluorescence=Fluorescence Intensity$_{sample}$−Fluorescence Intensity$_{TCFI\ control}$ Emission Ratio=Coumarin Emission (445 nm)/Fluorescein Emission (520 nm) (using values corrected for background fluorescence)

% Phosphorylation=1−(Emission Ratio×$F_{100\%}$−$C_{100\%}$)/{($C_{0\%}$−$C_{100\%}$)+[Emission Ratio×($F_{100\%}$−$F_{0\%}$)]}*100

% Inhibition=(1−% Phosphorylation$_{sample}$/% Phosphorylation$_{0\%\ inhibition\ Control}$)*100

C100%: Average Coumarin emission signal of the 100% Phosphorylation Control
C0%: Average Coumarin emission signal of the 0% Phosphorylation Control
F100%: Average Fluorescein emission signal of the 100% Phosphorylation Control
F0%: Average Fluorescein emission signal of the 0% Phosphorylation Control
DRI: Development Reaction Interference
TCFI: Test Compound Fluorescence Interference C-3. Results The results are described as Table 5.

TABLE 5

IC$_{50}$ of the test compound on YSK4

| Compound | YSK4 IC$_{50}$ (nM) |
|---|---|
| AR-13324 | n.a. |
| AR-13503 | n.a. |
| Compound 1 | + |
| Compound 2 | + |
| Compound 5 | + |
| Compound 6 | + |
| Compound 7 | ++ |
| Compound 8 | ++ |
| Compound 10 | + |
| Compound 11 | ++ |
| Compound 12 | ++ |
| Compound 13 | ++ |
| Compound 14 | ++ |
| Compound 15 | + |
| Compound 16 | + |
| Compound 17 | + |
| Compound 19 | ++ |

Note:
++++++ represents IC$_{50}$ < 1 nM;
+++++ represents IC$_{50}$ = 1-10 nM;
++++ represents IC$_{50}$ = 10-100 nM;
+++ represents IC$_{50}$ = 100-1000 nM;
++ represents IC$_{50}$ > 1,000 nM;
+ represents IC$_{50}$ > 10,000 nM.

According to the foregoing results, it can be known that the compounds synthesized in the present disclosure have inhibitory effects on ROCK, MYLK-4 and YSK4, and have synergistic target inhibitory effects, especially Compound 7 and Compound 20.

Moreover, since it is currently known that through inhibiting ROCK expression, the effects of protection of optic nerve (see for example, Rothschild et al., ROCK-1 mediates diabetes-induced retinal pigment epithelial and endothelial cell blebbing: Contribution to diabetic retinopathy. Scientific Reports. (2017) 7:8834 and Tanna et al., Rho Kinase Inhibitors as a Novel Treatment for Glaucoma and Ocular Hypertension. Ophthalmology. (2018) 125:1741-1756.) and alleviation and/or treatment of high intraocular pressure (see for example, Tanna et al., Rho Kinase Inhibitors as a Novel Treatment for Glaucoma and Ocular Hypertension. Ophthalmology. (2018) 125:1741-1756), glaucoma (see, for example, Tanna et al., Rho Kinase Inhibitors as a Novel Treatment for Glaucoma and Ocular Hypertension. Ophthalmology. (2018) 125:1741-1756), ocular stroke (see for example, Yi et al., Protective Effects of Intravitreal Injection of the Rho-Kinase Inhibitor Y-27632 in a Rodent Model of Nonarteritic Anterior Ischemic Optic Neuropathy (rAION). J Ophthalmol. (2020) 2020:1485425 and Nourinia R, et al. ROCK inhibitors for the treatment of ocular diseases. Br J Ophthalmol 2018; 102:1-5.), macular degeneration (see, for example, Sadiq et al. Pharmacological agents in development for diabetic macular edema Int J Retin Vitr (2020) 6:29.), macular edema (see, for example, Sadiq et al. Pharmacological agents in development for diabetic macular edema Int J Retin Vitr (2020) 6:29.), diabetic retinopathy (see, for example, Nourinia R, et al. ROCK inhibitors for the treatment of ocular diseases. Br J Ophthalmol 2018; 102:1-5), Fuchs endothelial corneal dystrophy (FECD) (see, for example, Okumura et al. The ROCK Inhibitor Eye Drop Accelerates Corneal Endothelium Wound Healing Invest Ophthalmol Vis Sci. (2013) 54:2439-2502.), corneal fibrosis (see, for example, Sloniecka et al., Substance P induces fibrotic changes through activation of the RhoA/ROCK pathway in an in vitro human corneal fibrosis model. J Mol Med (Berl). 2019; 97(10): 1477-1489), etc. can be achieved, the compounds with the effect of inhibiting ROCK of the present disclosure mentioned above, can also be used in ophthalmology related applications, such as protection of optic nerve, and/or prevention and/or treatment of high intraocular pressure, glaucoma, ocular stroke, macular degeneration, macular edema, diabetic retinopathy, Fuchs endothelial corneal dystrophy (FECD) and/or corneal fibrosis, etc.

Furthermore, since it is also currently known that through inhibiting ROCK expression, the effects of alleviation and/or treatment of pulmonary hypertension (see, for example, Zhang et al., Effects of Fasudil on Patients with Pulmonary Hypertension Associated with Left Ventricular Heart Failure with Preserved Ejection Fraction: A Prospective Intervention Study. Can Respir J. (2018) 2018:314825), chronic obstructive pulmonary disease (COPD) (see, for example, Liu et al., Influence of Rho kinase inhibitor Fasudil on late endothelial progenitor cells in peripheral blood of COPD patients with pulmonary artery hypertension. Bosn J Basic Med Sci. (2014) 14(1):40-4), idiopathic pulmonary fibrosis (IPF) (see, for example, Knipe et al., The Rho Kinase Isoforms ROCK1 and ROCK2 Each Contribute to the Development of Experimental Pulmonary Fibrosis. Am J Respir Cell Mol Biol. (2018) 58(4): 471-481.), pulmonary emphysema (see, for example, Bewley et al., Differential Effects of p38, MAPK, PI3K or Rho Kinase Inhibitors on Bacterial Phagocytosis and Efferocytosis by Macrophages in COPD. PLoS One. (2016) 11(9): e0163139.), lung cancer (see, for example, Vigil et al., ROCK1 and ROCK2 are Required for Non-Small Cell Lung Cancer Anchorage-Independent Growth and Invasion. Cancer Res. (2012) 15:72(20).), etc. can be achieved, the compounds with the effect of inhibiting ROCK of the present disclosure mentioned above, can also be used in lung-related applications such as prevention and/or treatment of pulmonary hypertension, chronic obstructive pulmonary disease (COPD), idiopathic pulmonary fibrosis (IPF), pulmonary emphysema and/or lung cancer, etc.

Example 3

The maximal effect (Emax) dose evaluation of the intraocular pressure reduction model in normal rabbit A. Compound 20

1. Method

Animals: Male New Zealand white rabbits (n=7/each group);

Formulation for test compound: 0.01% Compound 20; 0.03% Compound 20; 0.1% Compound;

Administration: 50 µL of the test compound was instilled in the right eye (dosed eye) and 50 µL of the vehicle (without the test compound) in the left eye (control eye) of each experimental animal. The 3 formulation mentioned above were administered once a day for 3 consecutive days.

The intraocular pressure of each animal was measured by Tono-Vet (iCare) before administration (0 hours) and 2, 4, 6 and 8 hours after administration on Day 1 and Day 3.

2. Results

Figure 1B:
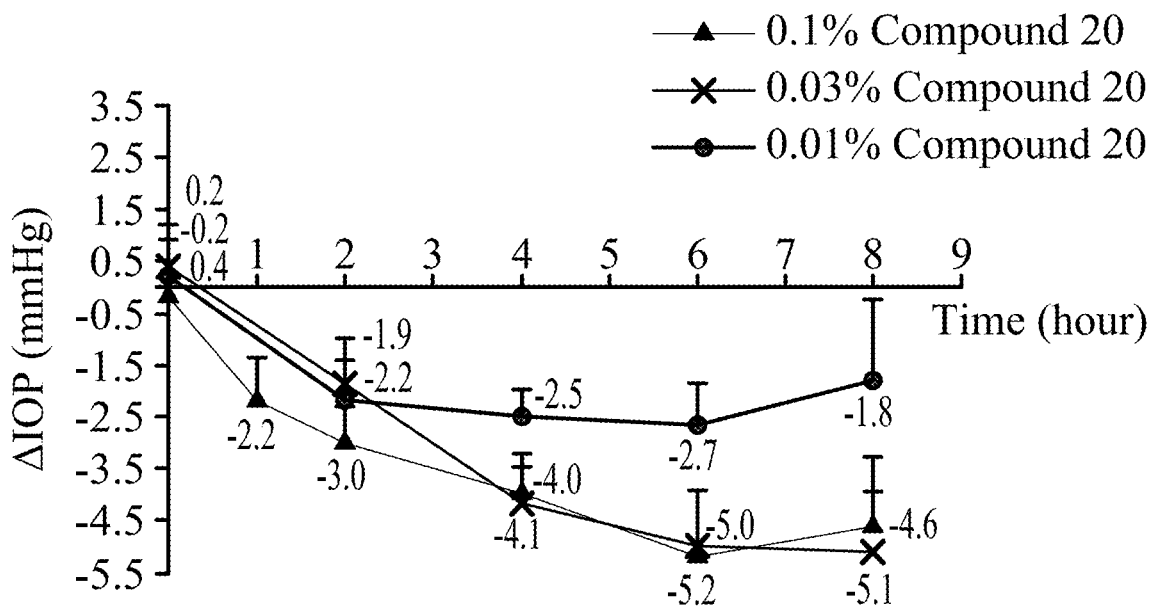
FIG. 1B shows the results of intraocular pressure measurements for administration of the compound of the present disclosure with different concentration in rabbit eyes with normal intraocular pressure on the Day 3.

The results are shown in FIG. 1A and FIG. 1B and Table 6 and Table 7.

TABLE 6

Results of intraocular pressure measurement on Day 1

| Concentration of Compound 20 | The magnitude of intraocular pressure reduction ($\Delta$IOP) (mmHg) | The maximum magnitude of the reduction in intraocular pressure | $T_{max}$ (hour) |
|---|---|---|---|
| 0.10% | −5.3 ± 0.6 | 32.2% | 8 |
| 0.03% | −4.3 ± 1.2 | 28.3% | 8 |
| 0.01% | −2.9 ± 1.1 | 18.7% | 6 |

The maximum magnitude of the reduction in intraocular pressure %=(Intraocular pressure of the control eye−Intraocular pressure of the dosed eye)/Intraocular pressure of the control eye*100

TABLE 7

Results of intraocular pressure measurement on Day 3

| Concentration of Compound 20 | The magnitude of intraocular pressure desc ($\Delta$IOP) (mmHg) | The maximum magnitude of the reduction in intraocular pressure | $T_{max}$ (hour) |
|---|---|---|---|
| 0.10% | −5.2 ± 1.3 | 32.6% | 6 |
| 0.03% | −5.1 ± 1.2 | 30.5% | 8 |
| 0.01% | −2.7 ± 0.8 | 15.4% | 6 |

The maximum magnitude of the reduction in intraocular pressure %=(Intraocular pressure of the control eye−Intraocular pressure of the dosed eye)/Intraocular pressure of the control eye*100

FIG. 1A and Table 6 show the results of intraocular pressure measurement on Day 1 of administration. FIG. 1B and Table 7 show the results of intraocular pressure measurement on Day 3 of administration.

The results show that Compound 20 exhibits a dose dependent effect in reduction of intraocular pressure, wherein the group administered with 0.03% Compound 20 and the group administered with 0.1% Compound 20 have similar magnitude and trend in lowering intraocular pressure.

In addition, after continuous administration for 3 days, the group administered 0.03% Compound 20 had a slight accumulation of drug effect (the reduction in intraocular pressure on Day 3 increased by nearly 1 mmHg on average compared to Day 1) (see Table 6 and Table 7). This result shows that Compound 20 at a concentration of 0.03% should be close to the intraocular pressure test limit of this model, and thus the cumulative difference of medicinal effect (Emax) shown thereby it is not significant.

The data presented in this experiment is the data that has removed the unqualified data (white rabbits with an intraocular pressure difference ≥2 mmHg (n=1) in the two eyes on Day 1 and >5 mmHg in the two eyes before the administration on the Day 3 (n=1) have been removed) and removed the rebound high intraocular pressure (n=3). The n value of each group ≥3; in addition, the n value of the group administered with 0.01% Compound 20 was 6.

Based on the results mentioned above, it can be known that the concentration of 0.03% should be the maximum effect (Emax) dose of Compound 20 in the normal intraocular pressure rabbit model.

B. Compounds 4, 5, 7, 8, 11, 12 and 14

Using a similar method to Compound 20, the maximum effective doses of compounds 4, 5, 7, 8, 11, 12, and 14 in a normal intraocular pressure rabbit model were confirmed.

The results show that the maximum effective doses of compounds 4, 5, 7 and 8 were all 1%, and the maximum effective doses of compounds 11, 12 and 14 were 0.5%, 0.25% and 0.5%, respectively.

Example 4

Evaluation of the Effect of Decreasing Intraocular Pressure in a Model of Rabbit with Normal Intraocular Pressure A. Compound 20

1. Material and Method

Experimental animal: New Zealand white rabbit, male, weighing more than 2 kg. New Zealand white rabbits were purchased from Huijun Farm (Changhua, Taiwan). After a one-week quarantine period, they were raised in MASTER LABORATORY Co., Ltd under the environmental conditions of 16-22° C., 30-70% relative humidity (RH), 8 hours day/16 hours night.

Experimental Method:

(1) Evaluation of the Effect of Reducing Intraocular Pressure

After weighing 12 New Zealand white rabbits (2.0-4.0 kg) and grouping them (n=3-6 in each group), the white rabbits were fixed with a wrap. After the white rabbit was in a stable state, the lower eyelid of its right eye were opened, and 50 μL of the test sample (eye drops containing 0.1% or 0.03% Compound 20) was instilled into the conjunctival sac of the right eye of the white rabbit, and the eyelid was closed, and the white rabbit was kept in a stable state for at least 2 minutes to avoid the white rabbit shaking its head causing the eye drops to flow out of the eye; the left eye was administered by vehicle (without test compound) as a control group. 0.02% AR-13324 was used as a benchmark to evaluate the medicinal effect competitiveness of the tested compounds. The intraocular pressure detection time points were before administration (0 hour) and 1, 2, 4, 6 and 8 hours after administration.

(2) Irritation Evaluation

After measuring the intraocular pressure, the appearance of rabbit eyes were photographed, and adverse event on the cornea, iris, or conjunctiva of the rabbit's eyes resulted from the test substance were evaluated according to the eye irritation test guidelines (OECD/OCDE 405) stipulated by the Organization for Economic Cooperation and Development (OECD).

The scoring manner of OECD/OCDE 405 for cornea, iris or conjunctiva is shown in Table 8.

TABLE 8

| Eye irritation level | |
|---|---|
| Opacity | Degree of density (readings should be taken from most dense area)* |
| No ulceration or opacity | 0 |
| Scattered or diffuse areas of opacity (other than slight dulling of normal luster); details of iris clearly visible | 1 |
| Easily discernible translucent area; details of iris slightly obscured | 2 |
| Nacrous area; no details of iris visible; size of pupil barely discernible | 3 |
| Opaque cornea; iris not discernible through the opacity | 4 |

Maximum possible: 4
*The area of corneal opacity should be noted (3) Observation of Cornea Eye drops of 0.1% Compound 20 was used as a test sample while the experimental method was the same as the experimental method described in the above "(1) Evaluation of the effect of reducing intraocular pressure". Administration was performed continuously for 7 days (once a day), an then the corneal state was observed with a slit lamp.

(4) Content Analysis for Candidate Drug in Aqueous Humor (AH) after Administration Compound 20 was administered to normal rabbits, and the content of the compound in aqueous humor was confirmed at different time points.

2. Results

Figure 2:
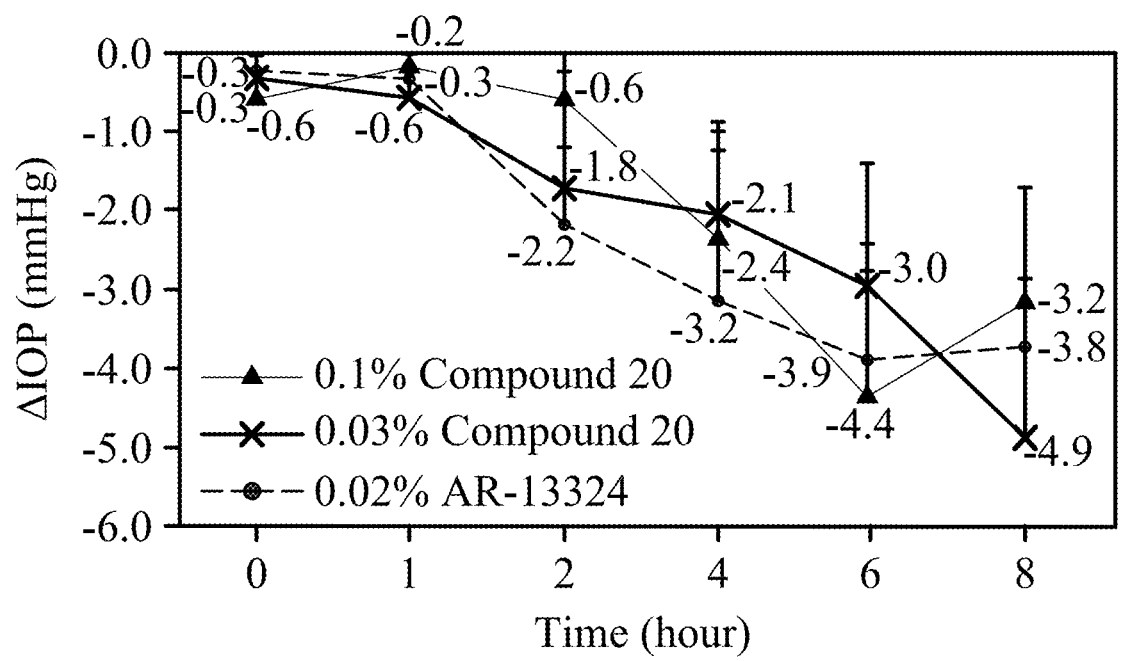
FIG. 2 shows the intraocular pressure reducing effects of the compound of the present disclosure and a commercial drug in rabbit eyes with normal intraocular pressure.

The results of evaluation of the effect of reducing intraocular pressure are shown in FIG. 2.

According to FIG. 2, it is known that the eye drops containing 0.1% Compound 20 and the eye drops containing 0.03% Compound 20 show the maximum effects (Emax) at 6-8 hours after administration, and the maximum magnitude of the reduction in intraocular pressure thereof are about 4.4-4.9 mmHg, and eye irritation thereof is slight.

In addition, the result also shows that the eye drops containing 0.03% Compound 20 in the normal intraocular pressure rabbit model has reached the maximum effect of reducing intraocular pressure.

Figure 3A:
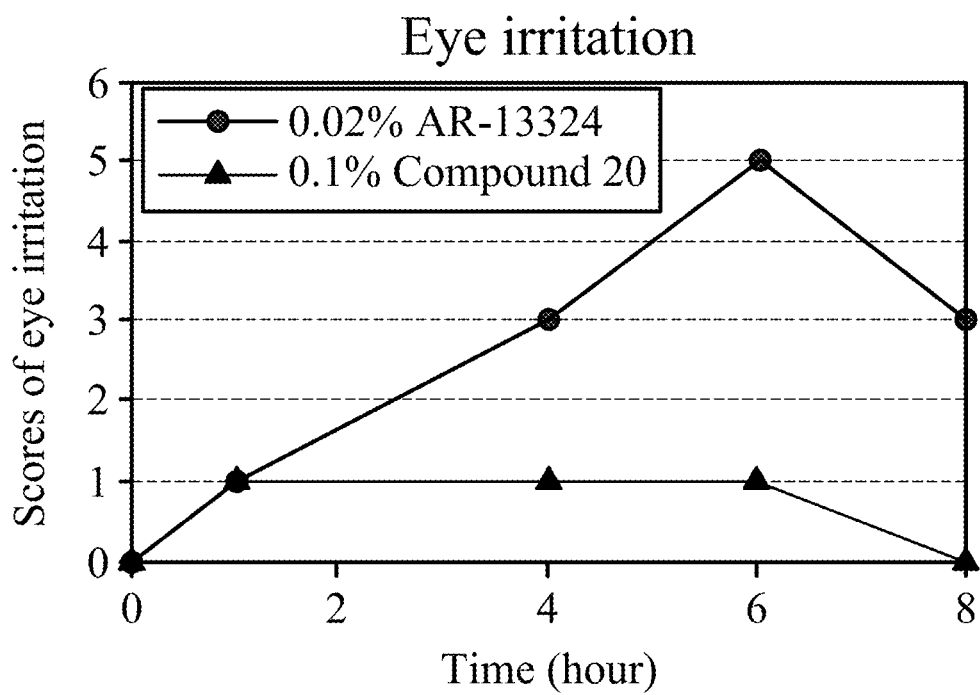
FIG. 3A shows the scores of eye irritation evaluation of the compound of the present disclosure and a commercial drug.
Figure 3B:
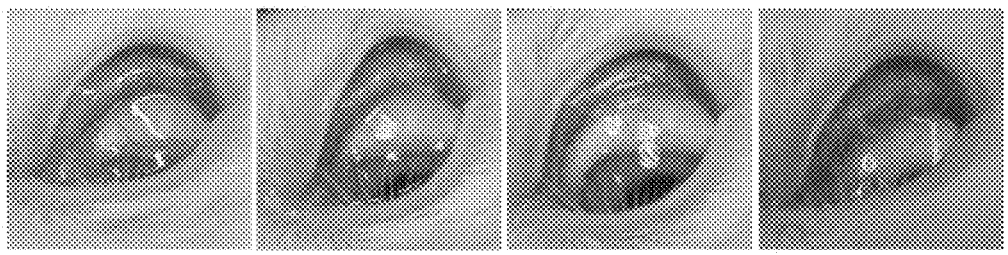
FIG. 3B shows photographs of rabbit eyes treated with the compound of the present disclosure and a commercial drug in the eye irritation evaluation.
Figure 3B:
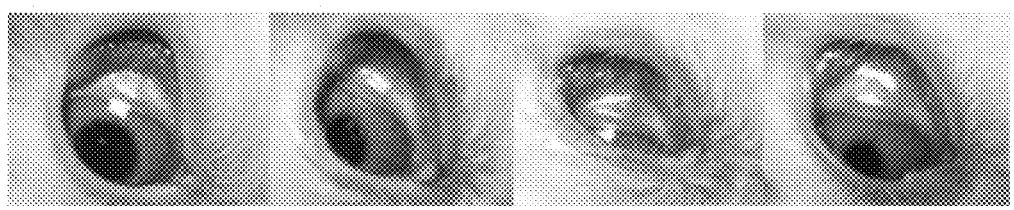
Figure 3C:
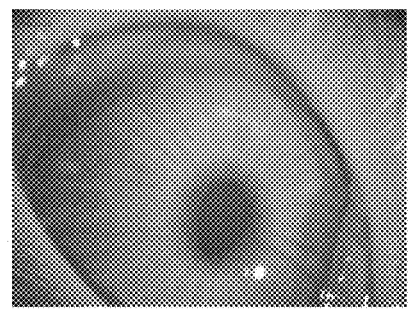
FIG. 3C shows a photograph showing that the cornea of the rabbit eyes administered with the compound of the present disclosure continuously for 7 days shows no turbidity and damage in the eye irritation evaluation.

The results of eye irritation evaluation are shown in FIG. 3A, FIG. 3B and FIG. 3C.

Based on FIG. 3A and FIG. 3B, it is known that the eye irritation of Compound 20 at the maximum dose effect dose (0.1%) is still lower than AR-13324 (0.02%).

In addition, FIG. 3C shows that the cornea is still free of damage and turbidity after continuous administration for 7 days.

Figure 4:
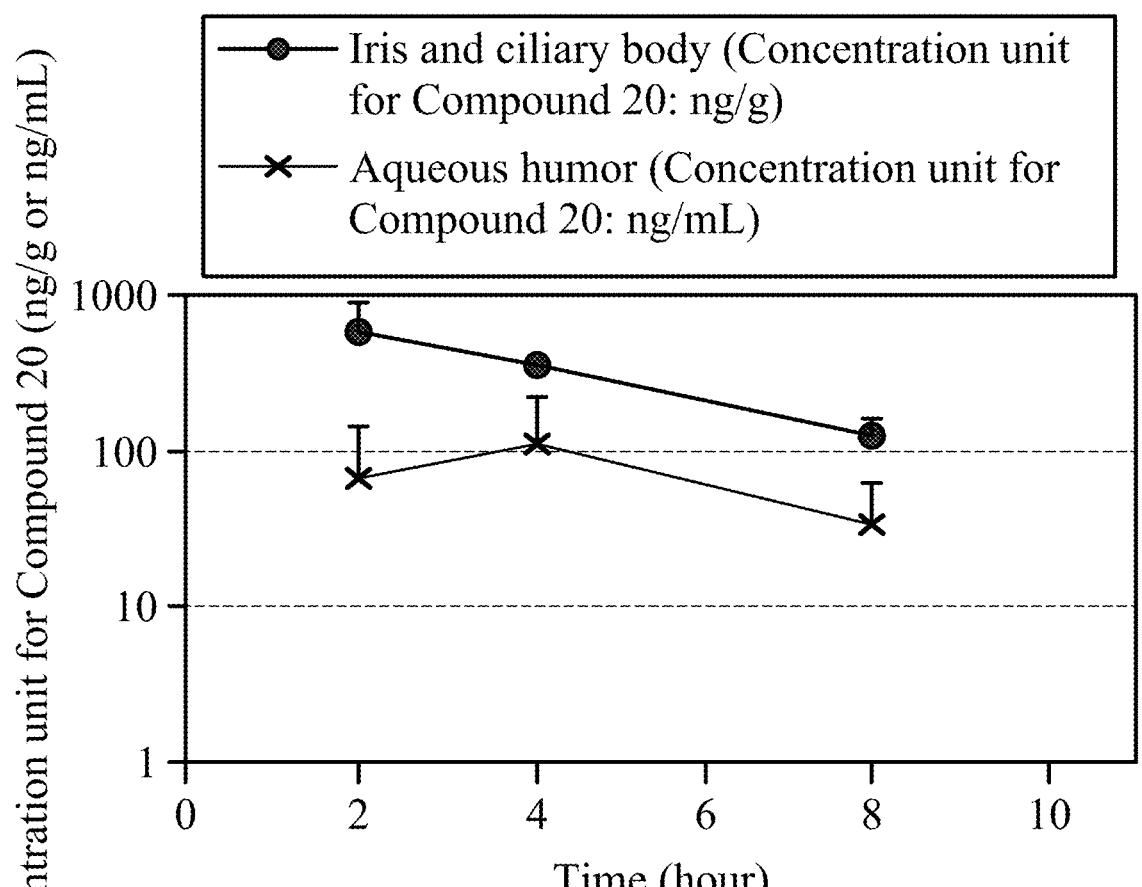
FIG. 4 shows the test result in which in rabbit eyes with normal intraocular pressure, the drug concentration of the compound of the present disclosure at the target tissue reaches the target effect $IC_{90}$ or more within 8 hours. For the iris and ciliary body, the concentration of Compound 20 is measured in unit ng/g; for aqueous humor, the concentration of Compound 20 is measured in unit ng/mL.

The content analysis results of Compound 20 presenting in the iris and ciliary body and aqueous humor after administration are shown in FIG. 4. For the iris and ciliary body, the concentration of Compound 20 was measured in unit of ng/g; for aqueous humor, the concentration of Compound 20 is measured in unit of ng/mL.

According to FIG. 4, it is known that after administration, the content of Compound 20 in the aqueous humor can reach the requirement of ROCK inhibition.

B. Compounds 4, 5, 7, 8, 11, 12 and 14

1. Method (1) Evaluation of the Effect of Reducing Intraocular Pressure

Using a similar method to Compound 20, the effects of reducing intraocular pressure of compounds 4, 5, 7, 8, 11, 12, 14, 20 and 21 (using the maximum effect dose) in a normal intraocular pressure rabbit model were confirmed.

(2) Safety Margin Assay

Compound 7 was taken as a representative, the eye drops containing 2% Compound 7 were administered to rabbit eyes (3 doses a day, with an interval of 3 hours each time, and observation was performed before administration and 1 hour after each administration). In addition, Eye drops containing 0.04% Compound 7 were administered to rabbit eyes (one dose a day, and observation was performed before administration and 1 hour and 6 hours after administration). According to the eye irritation test guidelines (OECD/OCDE 405) stipulated by the Organization for Economic Cooperation and Development (OECD) mentioned above, the eye irritation of Compound 7 was evaluated.

2. Results

The results of Evaluation of the effect of reducing intraocular pressure are shown in Table 9.

TABLE 9

The results of evaluation of the effect of reducing intraocular pressure

| Compound | Intraocular pressure difference (mmHg)/dose/time point at which maximum effect is achieved |
|---|---|
| AR-13324 | 4.5/1%/6 hours |
| Compound 4 | 4.2/1%/2 hours |
| Compound 5 | 1.5/1%/6 hours |
| Compound 7 | 5.1/1%/4 hours |
| Compound 8 | 5.2/1%/6 hours |
| Compound 11 | 2.0/0.5%/1 hours |
| Compound 12 | 2.0/0.25%/6 hours |
| Compound 14 | 2.5/0.5%/6 hours |
| Compound 20 | 4.9/0.03%/8 hours |
| Compound 21 | 1.3/0.03%/8 hours |

Figure 5:
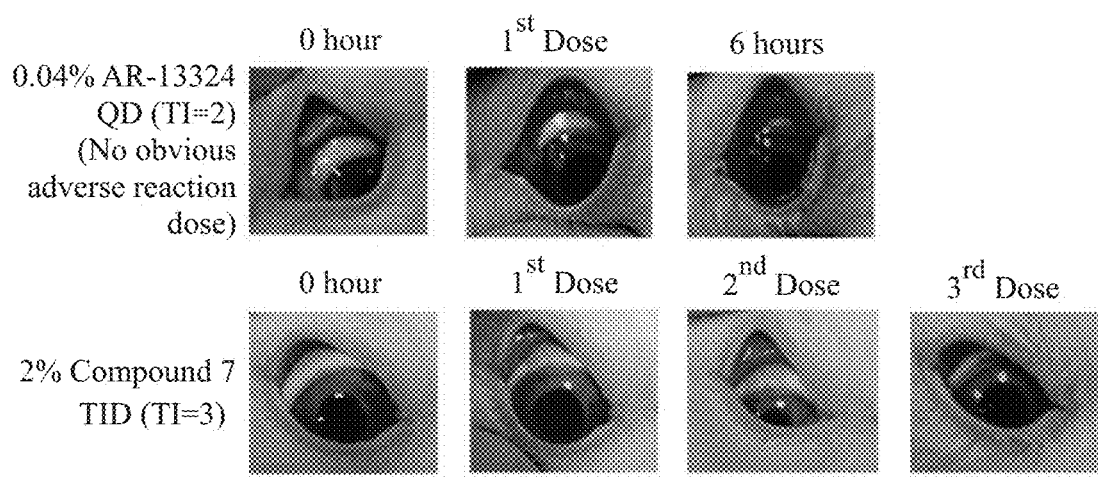
FIG. 5 shows the results of the safety margin test of the compound of the present disclosure in rabbit eyes with normal intraocular pressure.

The results of safety margin assay are shown in FIG. 5 and Table 10.

TABLE 10

The results of safety margin assay

| Safety margin | AR-13324 | Compound 7 |
|---|---|---|
| Therapeutic index (TI) | 2 | 3 |

| OECD Score | | |
|---|---|---|
| | AR-13324 (Therapeutic index: 2) | Compound 7 (Therapeutic index: 3) |
| Redness | 1 | 1 |
| Chemosis | 1 | 0 |
| Discharge | 2 | 1 |
| Total | 4 | 2 |

Based on FIG. 5 and Table 10, it is known that when AR-133247 is at a therapeutic index of 2, the total score of OECD405 is 4, and when Compound 7 is at a therapeutic index of 3, the total score of OECD405 is 2. Therefore, the safety margin of Compound 7 is better than AR-13324.

Example 5

Animal Model of Macaque

1. Material and Method

Eye drop containing 0.1% or 0.03% Compound 20 was administered to normal macaques. 0.02% AR-13324 was used as a benchmark to evaluate the medicinal effect competitiveness of the tested compounds. The intraocular pressure of animals was measured by a pneumatic tonometer (Model 30™ Pneumatonometer). Animal anesthesia was required before intraocular pressure measurement. After topical administration (once a day), the intraocular pressure of the animals was measured at the set time points.

2. Results

The results are shown in Table 6.

Figure 6:
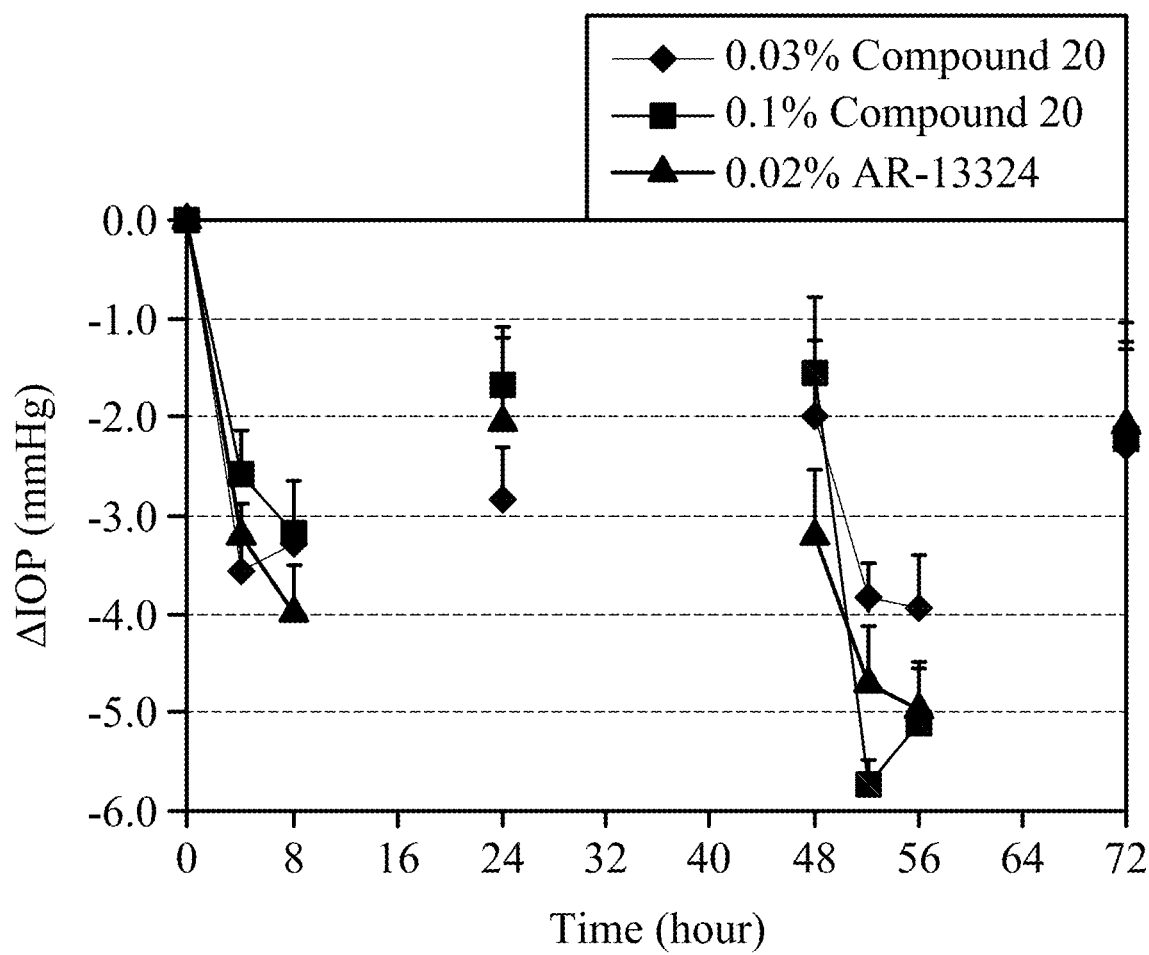
FIG. 6 shows the intraocular pressure reducing effects of the compound of the present disclosure and a commercial drug in macaques with normal intraocular pressure.

Based on FIG. 6, it can be known that Compound 20 can achieve an effect of reducing intraocular pressure which is equivalent to or better than that of AR-13324 in normal intraocular pressure macaque without obvious side effects, such as pink eye.

Example 6

Evaluation of the effect of reducing intraocular pressure in model of hypertonic saline induced high intraocular pressure rabbit (acute high intraocular pressure model)

1. Material and Method

Experimental animal: New Zealand white rabbit, male, weighing 2.0-3.0 kg. New Zealand white rabbits were purchased from a qualified laboratory animal rabbit farm in Taiwan before the experiment and were raised in the Animal Center of National Chiao Tung University.

Test sample: Eye drop containing 0.1% Compound 20

Negative control 1: Physiological saline

Negative control 2: Vehicle without test substance (containing 5% mannitol, 20 mM boric acid and 0.125% nonoxynol-9)

Experimental method: male New Zealand white rabbits were weighed and grouped and then anesthetized. 160 μL of hypertonic saline (5% NaCl) was injected into the vitreous bodies of the left and right eyes of the rabbit under anesthesia, so that the rabbit eyes became a state of high intraocular pressure. Next, 50 μL of physiological saline (0.9% NaCl), an eye drop containing 0.1% Compound 20, a vehicle used to prepare eye drop of Compound 20 (without Compound 20), and an eye drop containing 0.02% AR-13324 were instilled into the left and right eyes of each group of rabbits. The intraocular pressure (TOP) detection time points were before anesthesia (0 hours) and 0.5, 1, 1.5, 3, and 5 hours after administration. Physiological saline and a vehicle without test substance were used as a negative control group, and an eye drop containing 0.02% AR-13324 was used as a benchmark to evaluate the effect of Compound 20 in reducing intraocular pressure in a rabbit model of hyperosmotic saline-induced hypertension.

2. Results

Figure 7:
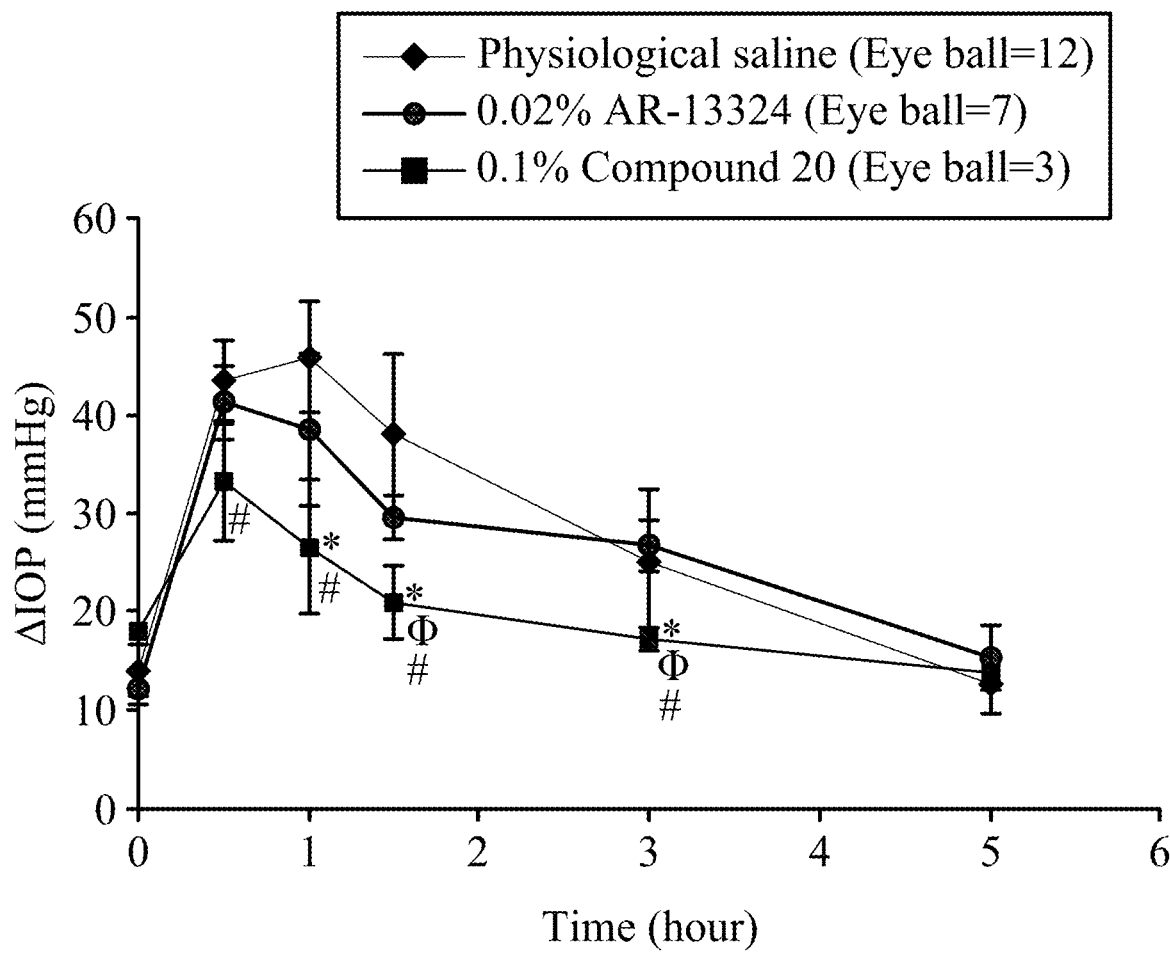
FIG. 7 shows the intraocular pressure reducing effects of the compound of the present disclosure and a commercial drug in rabbit eyes with high intraocular pressure induced by hypertonic saline. *: t-test, p-value <0.05 (compared to physiological saline); #: t-test, p-value <0.05 (compared to vehicle); ϕ: t-test, p-value <0.05 (compared to commercial drug (AR-13324)).

The results are shown in FIG. 7 and Table 11.

TABLE 11

Test results of reducing intraocular pressure in a rabbit model of high intraocular pressure
Transient ocular hypertension rabbits

| | Dose | Maximum intraocular pressure difference (mm Hg) | Maximum intraocular pressure difference (%) | AUC |
|---|---|---|---|---|
| Physiological saline | — | — | — | 139.7 |
| AR-13324 | 0.02% | −7.7 ± 4.2 | −20.8% | 132.9 |
| Vehicle used to prepare eye drop of Compound 20 (without Compound 20) | — | +7.2 ± 5.2 | +16.2% | NA |
| Compound 20 | 0.1% | −18.0 ± 6.8 | −40.4% | 99.1 |

Maximum intraocular pressure difference: The difference between an individual's TOP readings and the average TOP readings of the negative control group 1 (physiological saline) at the time point at which the maximum response is recorded (J Ocul Pharmacol Ther. 2010 April; 26(2): 125-132)

The results show that in the rabbit model of hyperosmolar saline-induced high intraocular pressure, the eye drop containing 0.1% Compound 20 can reduce the intraocular pressure by about 18.0±6.8 mmHg while the eye drop containing 0.02% AR-13324 can reduce the intraocular pressure by about 7.7±4.2 mmHg. It shows that the effect of Compound 20 in reducing intraocular pressure is significantly better than that of AR-13324 (t-test p<0.05). Moreover, compared with the physiological saline, the vehicle has no statistically significant difference (t-test). Compared with the physiological saline or the vehicle, AR-13324 also has no statistically significant difference (t-test).

Example 7

Evaluation of the effect of reducing intraocular pressure in model of magnetic bead induced high intraocular pressure rabbit (high intraocular pressure model with intraocular pressure >30 mmHg)

Exfoliation glaucoma (XFG) is considered to be more serious than primary open angle glaucoma. The maximum intraocular pressure (38.2 vs 26.9 mmHg), minimum intraocular pressure (24.7 vs 18.4 mmHg), and mean intraocular pressure change (13.5 vs 8.5 mmHg) in exfoliative glaucoma and primary corner open glaucoma are statistically significant difference. Furthermore, there are currently no known diet therapies, drugs or other interventions that can prevent the occurrence of exfoliation syndrome or slow down its development (Progress in Retinal and Eye Research Vol. 19, No. 3, pp. 345 to 368, 2000). According to the foregoing, it is known that the intraocular pressure of exfoliative glaucoma can reach >30 mmHg, and there is currently no effective drug for it, and thus a high intraocular pressure model with an intraocular pressure >30 mmHg is provided here to evaluate the feasibility of the compound of the present disclosure in the treatment of exfoliative glaucoma and ocular hypertension with intraocular pressure >30 mmHg.

A. Compound 20

1. Material and Method

Experimental animal: New Zealand white rabbit, male, body weight 2.0-3.0 kg. New Zealand white rabbits were purchased from Huijun Farm (Changhua, Taiwan) before the experiment and were raised in the Animal Center of National Chiao Tung University.

Test sample: Eye drop containing 0.1% Compound 20

Negative control 1: Vehicle without test Compound 20 (containing 5% mannitol, 20 mM boric acid and 0.125% nonoxynol-9)

Negative control 2: Vehicle without test compound AR-13324 (containing 4.7% D-mannitol and 0.05% boric acid)

Experimental method: After weighing and grouping male New Zealand white rabbits, the New Zealand white rabbits were anesthetized with Zoletil 50 0.2 mL/kg. 50 μL of magnetic bead solution (50 mg/mL, magnetic bead size of 10 μm) was injected into the left and right anterior eye chambers of the rabbit under anesthesia to make rabbit eyes become a state of high intraocular pressure. After the injection to the anterior chamber of the eye, a strong rubidium iron magnet ring was immediately put around the eye for 10-20 minutes to make the magnetic beads completely block the drainage tissue of the aqueous humor. After disinfecting the eyeball with antibiotics, moisturizing eye ointment was provided to restore the eyeball, and the intraocular pressure rising was waited. After about 3 days, the intraocular pressure can reach a high intraocular pressure >30 mmHg, and can last for at least 10 days. After the intraocular pressure reaches the target intraocular pressure >30 mmHg, the eye drop containing 0.03% or 0.1% of Compound 20 (right eye), the vehicle used to prepare the eye drop of Compound 20 (without Compound 20) (left eye), and the eye drop containing 0.02% AR-13324 (right eye), and the vehicle used to prepare AR-13324 eye drop (without AR-13324) (left eye) were respectively instilled one drop (about 35 μL) into the left and right eyes of the rabbits in each group. The intraocular pressure (TOP) detection time points were before administration (0 hour) and 2, 4, 6, and 8 hours after administration. The experiment was conducted for 2 consecutive days. The eye drop containing 0.02% AR-13324 was used as a benchmark to evaluate the effect of Compound 20 in reducing intraocular pressure in the model of magnetic bead induced high intraocular pressure rabbit (intraocular pressure >30 mmHg).

2. Results

Figure 8:
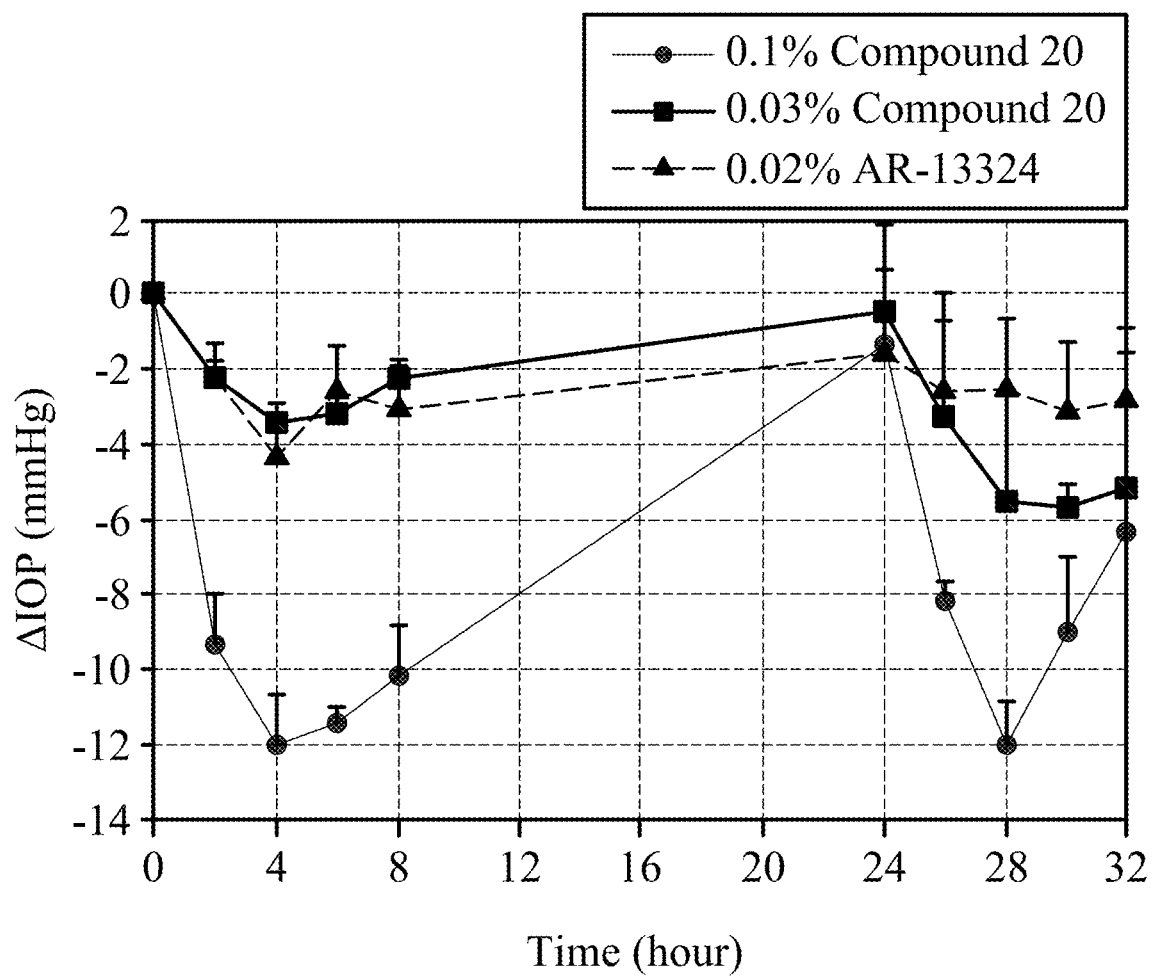
FIG. 8 shows the intraocular pressure reducing effects of the compound of the present disclosure and a commercial drug in rabbit eyes with high intraocular pressure induced by magnetic beads.

The results are shown as Table 12 and FIG. 8.

TABLE 12

Test results of reducing intraocular pressure of Compound 20 in a model of magnetic bead induced high intraocular pressure rabbit

| Compound 20 | Dose | Maximum intraocular pressure difference (mmHg) |
|---|---|---|
| AR-13324 | 0.02% | 4.3 ± 1.4 |
| Compound 20 | 0.03% | 5.7 ± 0.6 |
| | 0.1% | 12.1 ± 1.4 |

The results show that in the model of magnetic bead induced high intraocular pressure rabbit (the high intraocular pressure model with intraocular pressure >30 mmHg), the eye drop containing 0.03% Compound 20 can reduce the intraocular pressure by about 5.7±0.6 mmHg (by about 15.3%), and the eye drop containing 0.1% Compound 20 can reduce intraocular pressure by about 12.1±1.4 mmHg (by about 28.8%). Namely, the eye drop containing 0.03% Compound 20 and the eye drop containing 0.1% Compound 20 have better intraocular pressure reducing effects than those containing 0.02% AR-13324 (reducing intraocular pressure by about 4.3±1.4 mmHg (reducing by about 11.0%)), and the eye drop containing 0.1% Compound 20 can even be more than twice as effective as eye drops containing 0.02% AR-13324.

B. Compound 7

Using a similar method to that for Compound 20, the effect of Compound 7 (using maximum effect dose of 0.5% and 1%) in reducing intraocular pressure in a model of normal intraocular pressure rabbit was confirmed.

The results are shown in Table 13.

TABLE 13

Test results of reducing intraocular pressure of Compound 7 in a model of magnetic bead induced high intraocular pressure rabbit

| Compound | Dose | Maximum intraocular pressure difference (mmHg) |
| --- | --- | --- |
| AR-13324 | 0.02% | 3.6 ± 2.1 |
| Compound 7 | 0.5% | 6.7 ± 1.6 |
|  | 1% | 11.8 ± 0.8 |

According to Table 12, it is known that in the a model of magnetic bead induced high intraocular pressure rabbit (the high intraocular pressure model with intraocular pressure >30 mmHg), the eye drop containing 0.5% Compound 7 and the eye drop containing 1% Compound 7 have better intraocular pressure reducing effects than those containing 0.02% AR-13324, wherein the eye drop containing 1% Compound 7 can even be more than 3 times as effective as eye drops containing 0.02% AR-13324.

Example 8

1. Expression of MYLK-4 in Cells
(1) Method

Human Trabecular Meshwork (HTM) cells (Cat. NO. 6590) were obtained from ScienCell Research Laboratories. HTM cells were maintained in Trabecular Meshwork Cell Medium (TMCM) (Cat. NO. 6591). TMCM formulated from 500 mL basal medium, 10 mL FBS (Cat. NO. 0010), 5 mL trabecular meshwork cell growth supplement (TMCGS, Cat. NO. 6592) and 5 mL penicillin/streptomycin solution (P/S, Cat. NO. 503). When the cell growth reached 70-80% saturation, the HTM cells were treated overnight with 50 μg/mL dexamethasone (Cat. NO. 4902, Sigma).

The expression of MYLK4 and GAPDH in cell lysates was analyzed by Western blotting method. The expression of MYLK4 and GAPDH in cell lysates was analyzed by Western blotting method. First, the cells were collected and washed with 1×RIPA (50 mM Tris-HCl, pH 7.4, 150 mM NaCl, 0.25% deoxycholic acid, 0.1% NP-40, 1 mM EDTA, phosphatase inhibitor and protease inhibitor mixture). Next, the cell lysates were separated by SDS-PAGE (sodium dodecyl sulfate polyacrylamide gel electrophoresis) and transferred to PVDF membrane (iBlot™ 2 Transfer Stacks, polyvinylidene fluoride membrane, Invitrogen). Immunoblotting was performed on the membrane with primary antibodies (mouse anti-MYLK4 antibody (1:1,000, Cat. NO. SAB1412951) and mouse anti-GAPDH antibody (1:1,000, Cat. NO. G8795)), wherein GAPDH was used as a loading control. After that, the membrane was washed 3 times with 1×TBST. Next, the film and the secondary antibody (Cat. NO. 111-0350003, Cat. NO. 111-035-164) were incubated for 1 hour at room temperature. The membrane was visualized by an enhanced chemiluminescence (WBKLS0500, Millipore) detection system (Fisher Scientific, US).

(2) Results

Figure 9:
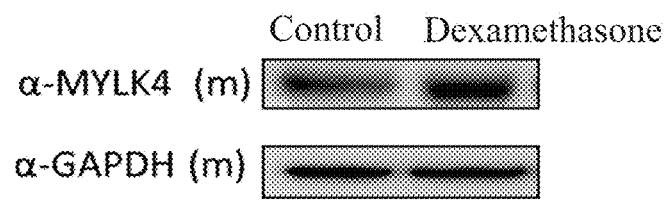
FIG. 9 shows the expression of myosin light chain kinase 4 (MYLK-4) in rabbit eyes with high intraocular pressure induced by magnetic beads.

The results are shown in FIG. 9.

According to FIG. 9, it is known that the expression level of MYLK-4 in HTM cells treated with dexamethasone (disease state cells) is higher than that of normal HTM cells.

2. MYLK-4 expression in magnetic bead-induced disease target tissue (1) Method

50 μL of magnetic bead solution (50 mg/mL, magnetic bead size of 10 μm) was injected into the anterior chamber of the left and right eyes of the rabbit under anesthesia, so that the rabbit's eyes became a state of high intraocular pressure. The white rabbits not treated with the magnetic bead solution were used as the control group. After that, the rabbits were sacrificed, the eyeballs were taken out, and histopathological analysis was performed.

Histopathological Interpretation Method:
Microscope: MoticEasyScan
Photomicrography system: MoticEasyScan
Interpretation Method:

GLOBAL VIEW BIOTECHNOLOGY INC. was entrusted to perform immunohistochemical (IHC staining) for rabbit eyeball paraffin tissue sections, and in addition to the interpretation of the results of the trabecular meshwork, a score sheet of interpretation results and photomicrographs of different magnifications were also provided.

After the removed eyeball tissues were fixed with formalin, they were dehydrated and embedded in paraffin, and then 3 μm thick paraffin tissue sections were made. The biomarkers for IHC staining are MYLK-4 and MLC-2.

According to the histopathological sections made by the specimen, the tissue lesions were observed and recorded under a microscope at 20 times, 40 times, 100 times, 200 times, and 400 times. According to the severity of the lesion, the range of distribution and the percentage of the tissue it occupies, the lesion is scored based on the 5-level grading method recommended by INHAND (International Harmonization of Nomenclature and Diagnostic Criteria): Grade 0 means that there is no obvious pathological change and the lesions account for less than 1% of the total tissue; Grade 1 means that the disease is minimal (1-5%); Grade 2 means that the disease is mild (mild, 6-25%); Grade 3 Represents moderate disease (moderate, 26-50%); Level 4 represents moderately severe disease (51-75%); Level 5 represents severe disease (severe/high, >76%).

(2) Results

Figure 10:
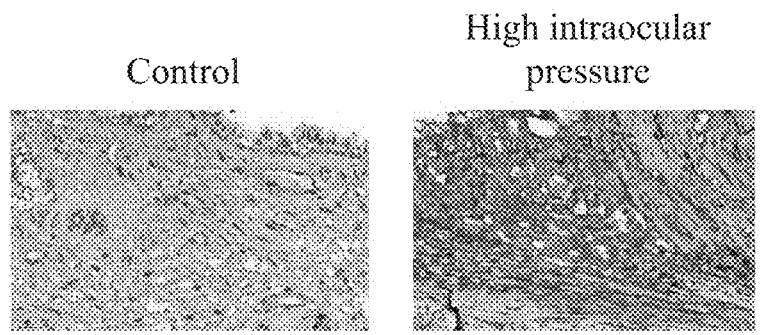
FIG. 10 shows the immunohistochemical staining of tissue sections of rabbit eyes with high intraocular pressure induced by magnetic beads.

The immunohistochemical staining results are shown in FIG. 10, and the scoring results are shown in Table 14.

TABLE 14

Scoring results of immunohistochemical staining

| Group | Score |
| --- | --- |
| Control | 0 |
| High intraocular pressure | 3.3 ± 0.6 |

According to FIG. 10 and Table 14, it can be known that whether it is diseased cells or diseased animal tissues (rabbit eyes induced by magnetic beads), the expression level of MYLK-4 is higher than that of normal cells and tissues. Therefore, it is presumed that the compound of the present disclosure with MYLK-4 inhibitory effect can effectively reduce intraocular pressure by inhibiting MYLK-4 in addition to by ROCK inhibitory effect.

Integrating the foregoing experimental results shows that, compared to AR-13324 only targeting ROCK, the Compound 20 of the present disclosure can simultaneously targets ROCK, MYLK-4 and YSK-4. In addition, in the model of hypertonic saline-induced high intraocular pressure rabbit (acute high intraocular pressure model) and the model of magnetic bead-induced high intraocular pressure rabbit (the high intraocular pressure model with intraocular pressure >30 mmHg), the intraocular pressure reducing effects of the Compound 20 of the present disclosure are better than those of AR-13324. In addition, Compound 20 of the present disclosure at the maximum effective dose has lower irritation than AR-13324.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A compound represented by Formula (I), Compound 16 or Compound 17, or a pharmaceutically acceptable salt or ester, hydrate, solvate or crystalline form thereof:

Formula (I)

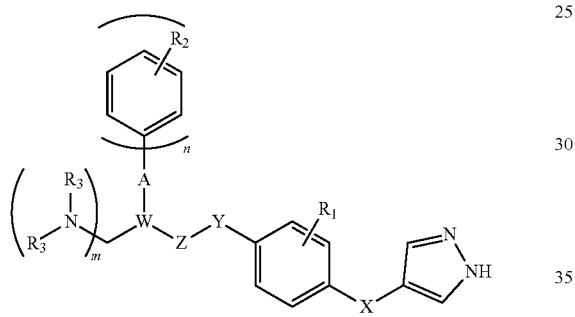

Compound 16

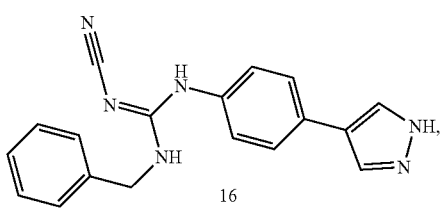

Compound 17

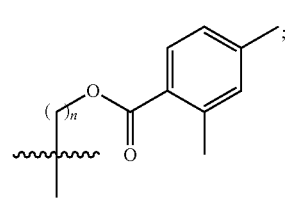

wherein the compound represented by Formula (I), Compound 16 and Compound 17 are β-amino acid derivatives, and in Formula (I):

X is a single bond or O;

Y is NH;

Z is C=O, C=S, NH, or

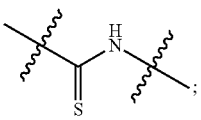 [SMILES: *NC(*)=S]

W is CH or NH;

when n is 0, then A is OH or $N_3$; when n is 1, then A is a single bond, O, $OCH_2$ or

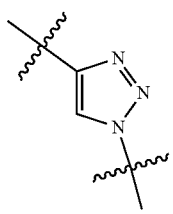 [SMILES: *c1cn(*)nn1]

or $N_3$;

$R_1$ is H or F;

$R_2$ is H, F, OH, $CF_3$, $CH_2OH$, CHO or $R_3$ is H;

n is 0 or 1: and m is 1.

2. The compound represented by Formula (I), Compound 16 or Compound 17, or a pharmaceutically acceptable salt or ester, hydrate, solvate or crystalline form thereof as claimed in claim 1, wherein the compound represented by Formula (I), Compound 16 or Compound 17 is present in the form of the individual optical isomers, a mixture of the individual enantiomers or a racemate, and the compound represented by Formula (I) comprises a compound selected from a group consisting of Compound 1 to Compound 15 and Compound 18 to Compound 21 shown in the following:

| Compound Number | Compound 1 | Compound 2 |
|---|---|---|
| Structure | 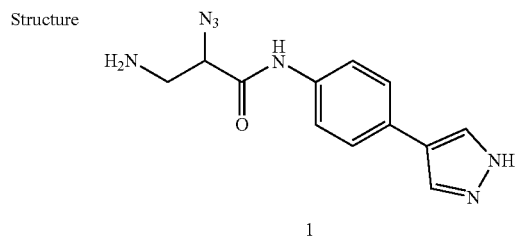 | 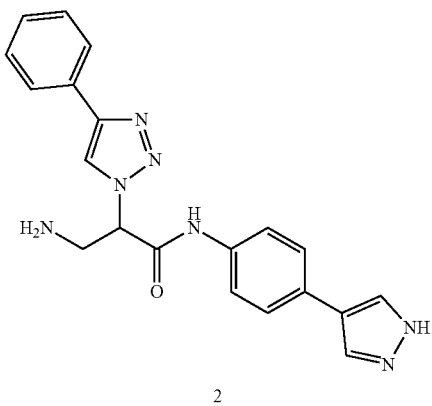 [SMILES: NCC(C(=O)Nc1ccc(-c2cn[nH]c2)cc1)n1cc(-c2ccccc2)nn1] |
| Compound Number | Compound 3 | Compound 4 |
|---|---|---|
| Structure | 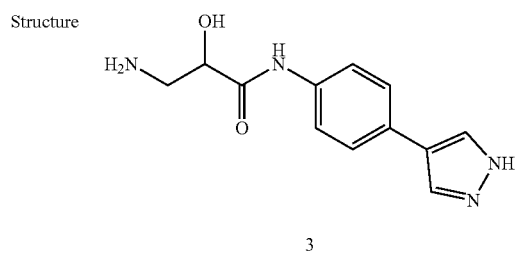 | 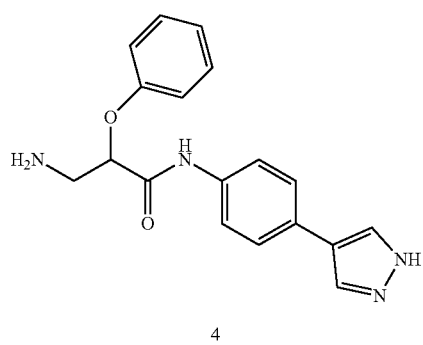 [SMILES: NCC(Oc1ccccc1)C(=O)Nc1ccc(-c2cn[nH]c2)cc1] |
| Compound Number | Compound 5 | Compound 6 |
|---|---|---|
| Structure | 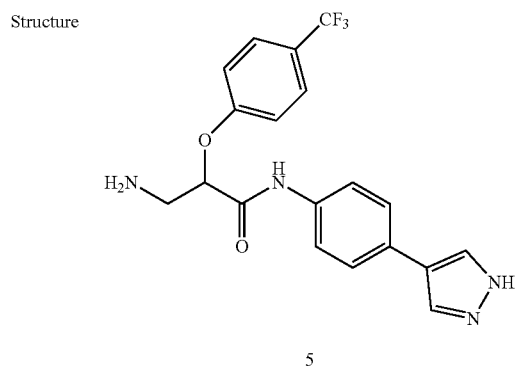 | 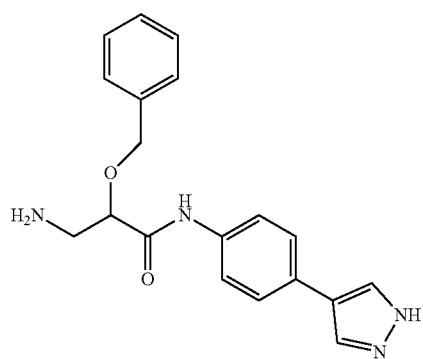 |

-continued
| Compound Number | Compound 7 | Compound 8 |
|---|---|---|
| Structure | 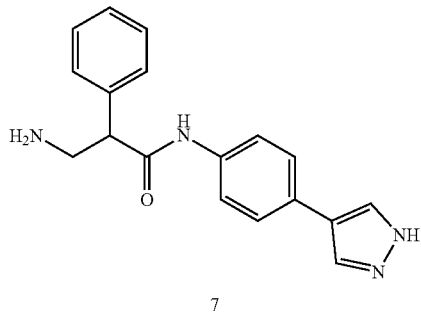 [SMILES: NCC(C(=O)Nc1ccc(-c2cn[nH]c2)cc1)c1ccccc1] | 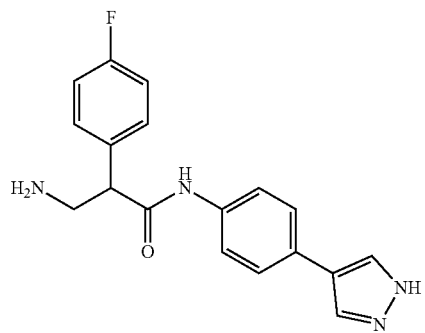 |
| Compound Number | Compound 9 | Compound 10 |
|---|---|---|
| Structure | 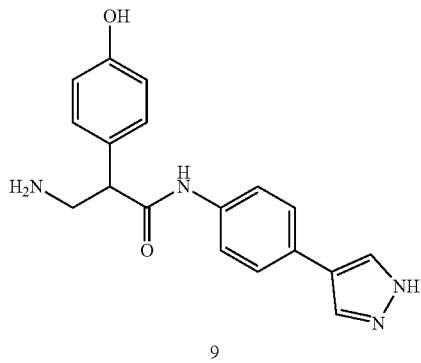 [SMILES: NCC(C(=O)Nc1ccc(-c2cn[nH]c2)cc1)c1ccc(O)cc1] | 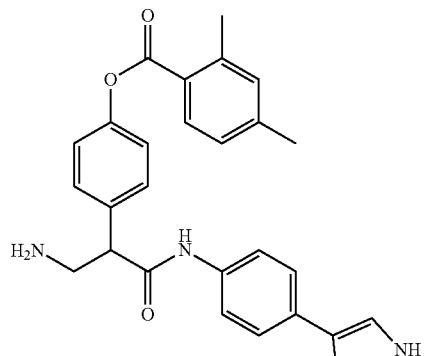 |
| Compound Number | Compound 11 | Compound 12 |
|---|---|---|
| Structure | 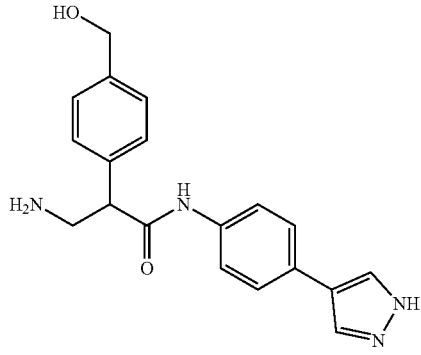 | 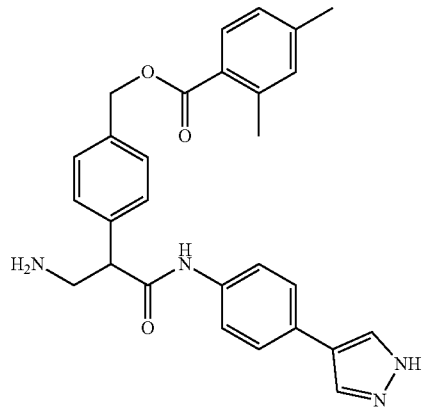 |

-continued
| Compound Number | Compound 13 | Compound 14 |
|---|---|---|
| Structure | 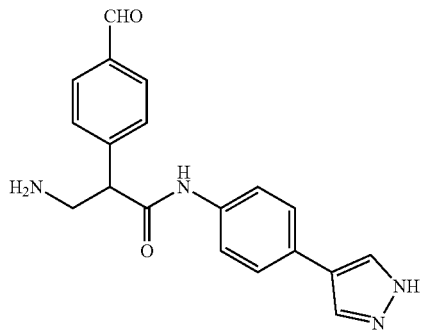 13 | 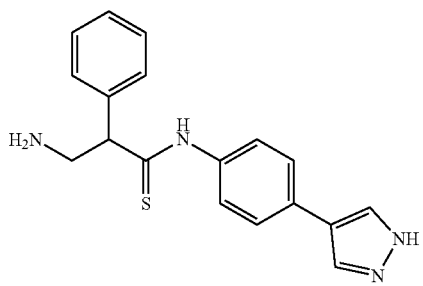 14 |
| Compound Number | Compound 15 | Compound 18 |
| Structure | 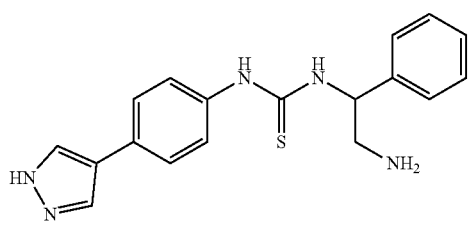 15 | 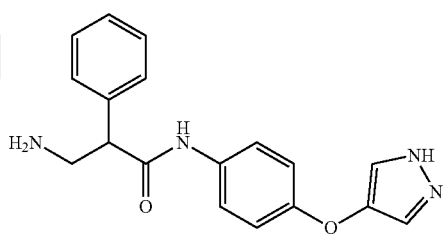 18 |
| Compound Number | Compound 19 | Compound 20 |
| Structure | 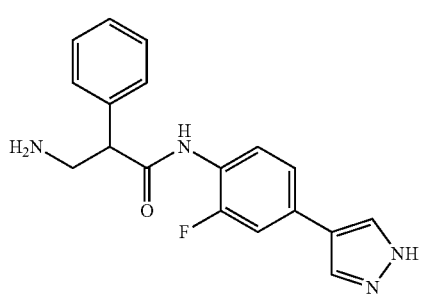 19 | 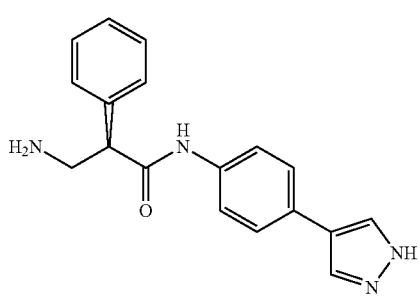 20 |
| Compound Number | Compound 21 | |
| Structure | 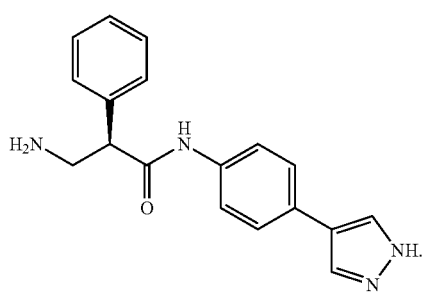 21 | |

3. A kinase inhibitor, comprising:
   the compound represented by Formula (I), Compound 16 or Compound 17, or a pharmaceutically acceptable salt or ester, hydrate, solvate or crystalline form thereof as claimed in claim 1.

4. The kinase inhibitor as claimed in claim 3, wherein the compound represented by Formula (I), Compound 16 or Compound 17 is present in the form of the individual optical isomers, a mixture of the individual enantiomers or a racemate, and the compound represented by Formula (I) comprises a compound selected from a group consisting of Compound 1 to Compound 15 and Compound 18 to Compound 21 shown in the following:

| Compound Number | Compound 1 | Compound 2 |
|---|---|---|
| Structure | 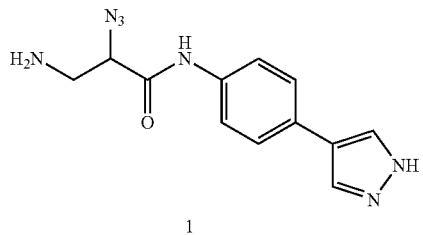 | 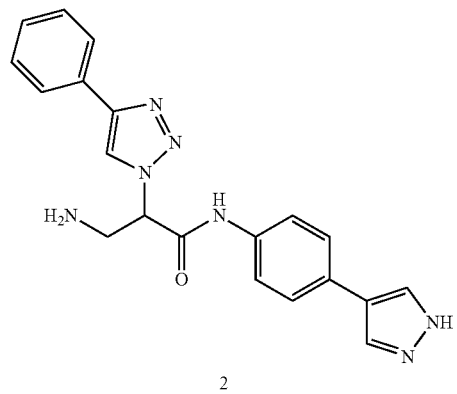 |

| Compound Number | Compound 3 | Compound 4 |
|---|---|---|
| Structure | 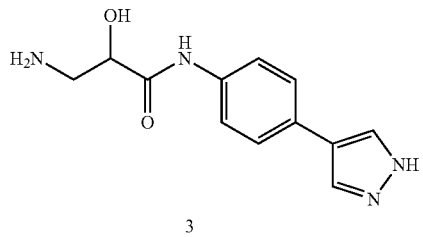 | 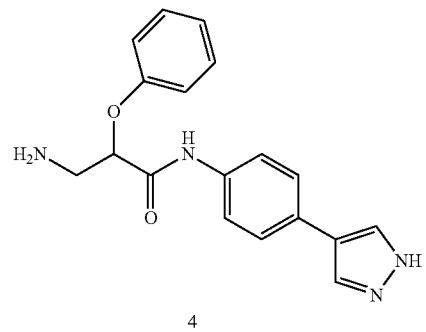 |

| Compound Number | Compound 5 | Compound 6 |
|---|---|---|
| Structure | 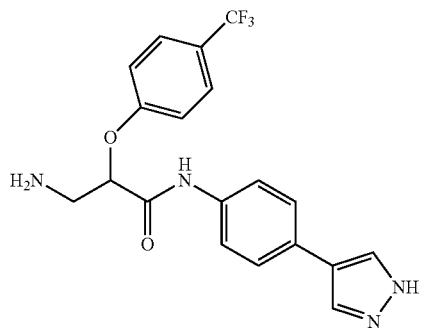 | 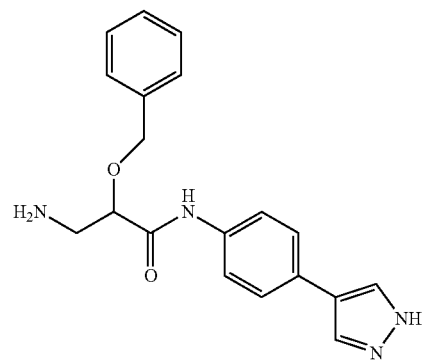 |

| Compound Number | Compound 7 | Compound 8 |
|---|---|---|
| Structure | 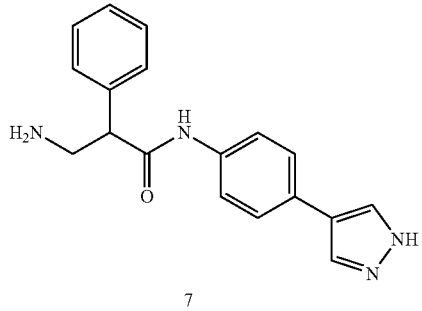 | 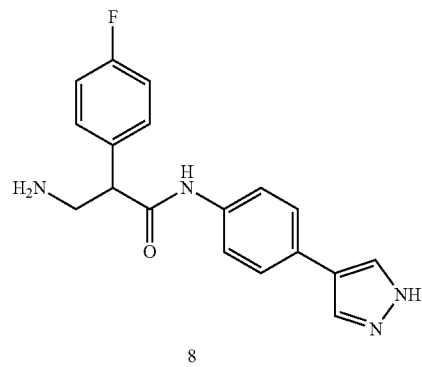 |
| Compound Number | Compound 9 | Compound 10 |
|---|---|---|
| Structure | 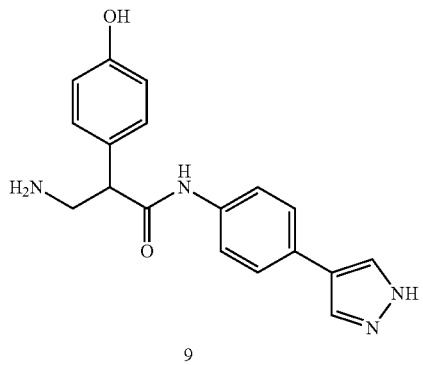 | 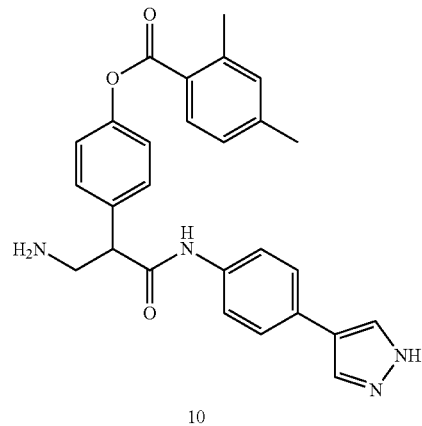 |
| Compound Number | Compound 11 | Compound 12 |
|---|---|---|
| Structure | 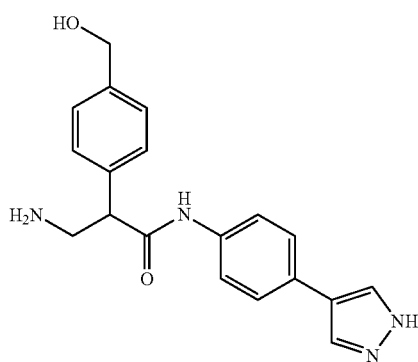 | 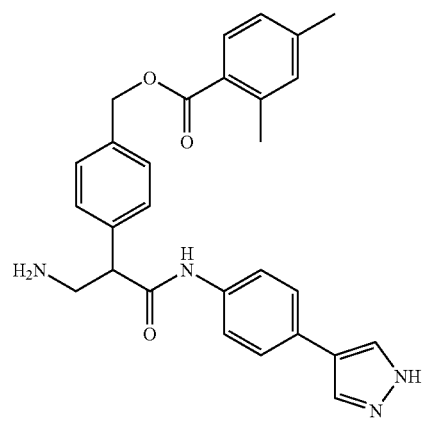 |

-continued
| Compound Number | Compound 13 | Compound 14 |
|---|---|---|
| Structure | 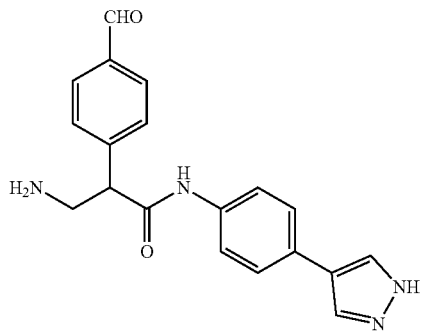<br>13 | 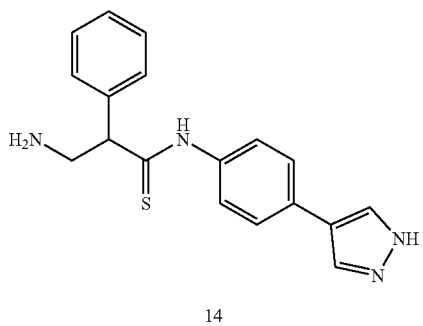 [SMILES: NCC(C(=S)Nc1ccc(-c2cn[nH]c2)cc1)c1ccccc1]<br>14 |
| Compound Number | Compound 15 | Compound 18 |
| Structure | 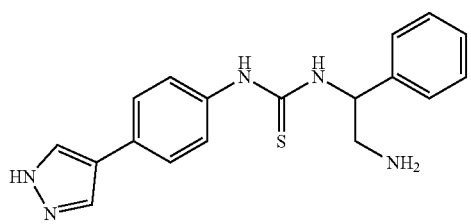<br>15 | 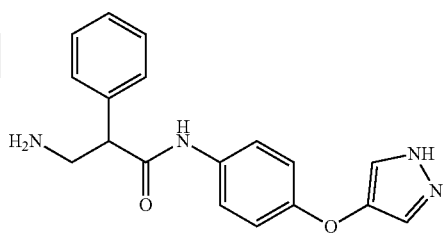<br>18 |
| Compound Number | Compound 19 | Compound 20 |
| Structure | 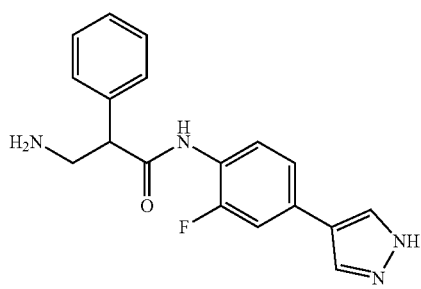<br>19 | 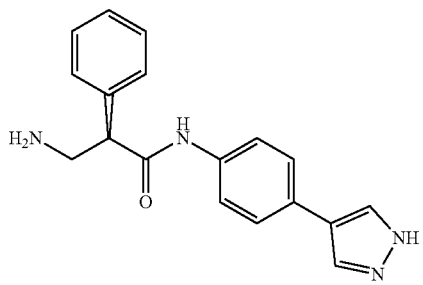<br>20 |
| Compound Number | Compound 21 | |
| Structure | 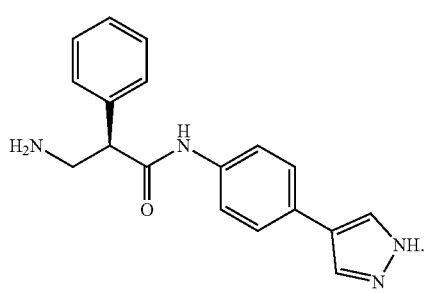<br>21 | |

5. The kinase inhibitor as claimed in claim 3, wherein the compound represented by Formula (I), Compound 16 or Compound 17 is capable of inhibiting myosin light chain kinase 4 (MYLK-4) and/or mitogen-activated protein kinase 19 (MAPK19, YSK-4).

6. The kinase inhibitor as claimed in claim 5, wherein the compound represented by Formula (I), Compound 16 or Compound 17 is further capable of inhibiting a Rho-associated protein kinase (ROCK).

7. The kinase inhibitor as claimed in claim 6, wherein the Rho-associated protein kinase (ROCK) comprises Rho-associated protein kinase-1 (ROCK-1).

8. A pharmaceutical composition, comprising: the compound represented by Formula (I), Compound 16 or Compound 17, or a pharmaceutically acceptable salt or ester, hydrate, solvate or crystalline form thereof as claimed in claim 1.

9. The pharmaceutical composition as claimed in claim 8, wherein the compound represented by Formula (I), Compound 16 or Compound 17 is present in the form of the individual optical isomers, a mixture of the individual enantiomers or a racemate, and the compound represented by Formula (I) comprises a compound selected from a group consisting of Compound 1 to Compound 15 and Compound 18 to Compound 21 shown in the following:

| Compound Number | Compound 1 | Compound 2 |
|---|---|---|
| Structure | 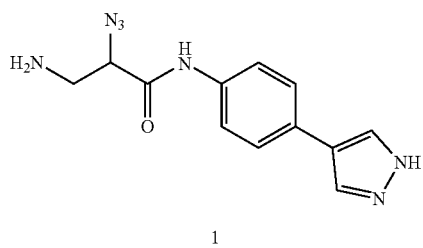 [SMILES: [N-]=[N+]=NC(CN)C(=O)Nc1ccc(-c2cn[nH]c2)cc1] | 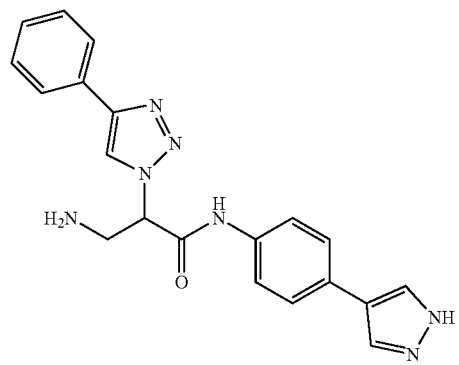 |
|  | 1 | 2 |

| Compound Number | Compound 3 | Compound 4 |
|---|---|---|
| Structure | 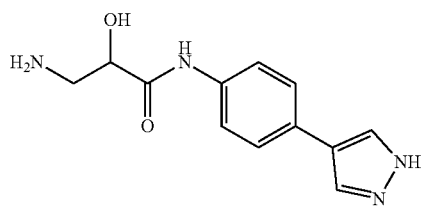 | 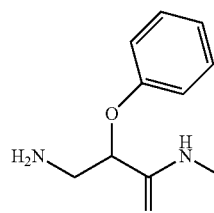 |
|  | 3 | 4 |

| Compound Number | Compound 5 | Compound 6 |
|---|---|---|
| Structure | 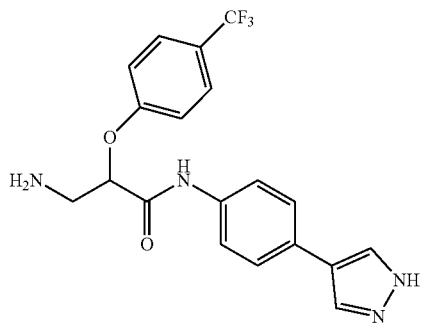 | 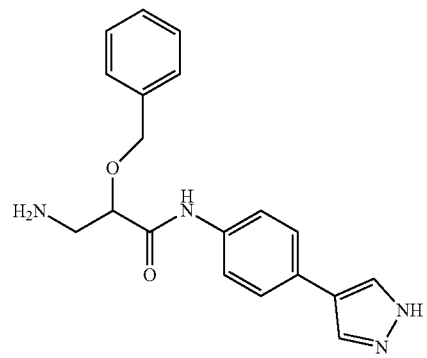 |
|  | 5 | 6 |
| Compound Number | Compound 7 | Compound 8 |
|---|---|---|
| Structure | 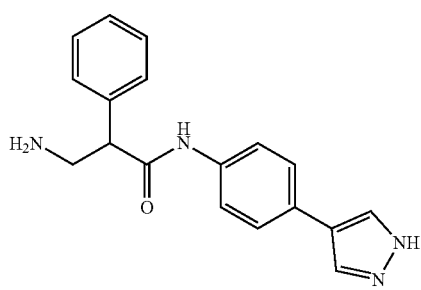 | 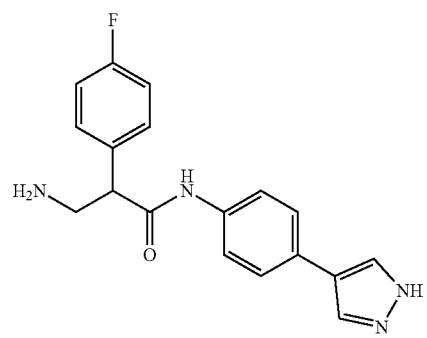 |
|  | 7 | 8 |
| Compound Number | Compound 9 | Compound 10 |
|---|---|---|
| Structure | 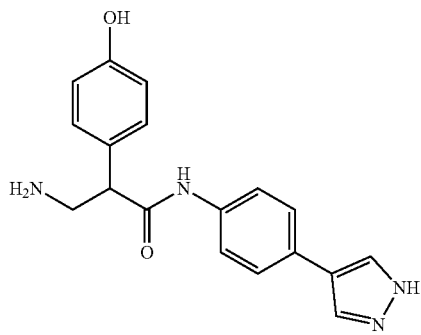 | 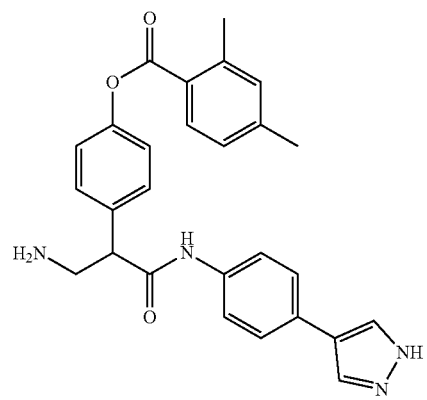 |
|  | 9 | 10 |

| Compound Number | Compound 11 | Compound 12 |
|---|---|---|
| Structure | 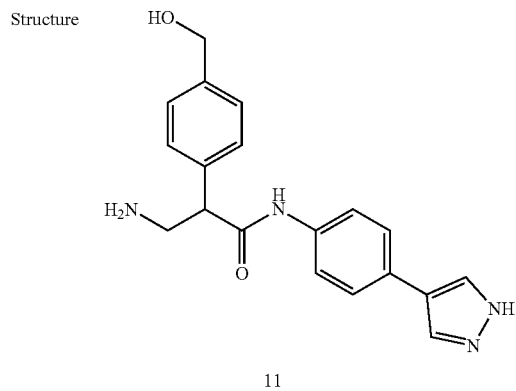 | 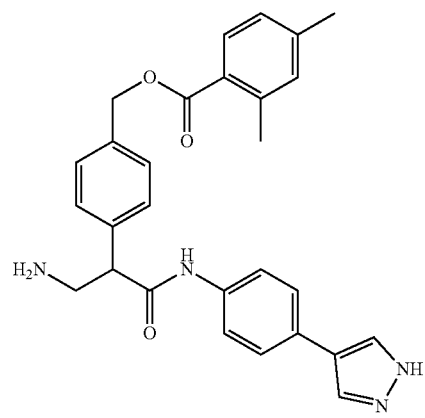 |
| Compound Number | Compound 13 | Compound 14 |
|---|---|---|
| Structure | 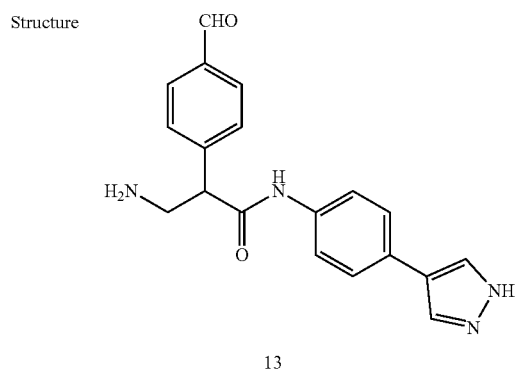 | 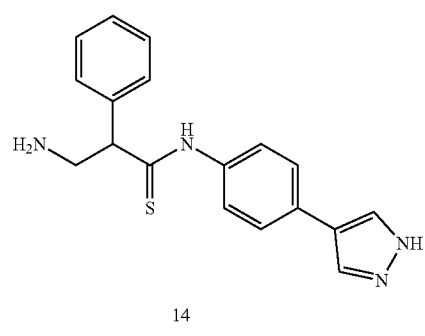 [SMILES: NCC(C(=S)Nc1ccc(-c2cn[nH]c2)cc1)c1ccccc1] |
| Compound Number | Compound 15 | Compound 18 |
|---|---|---|
| Structure | 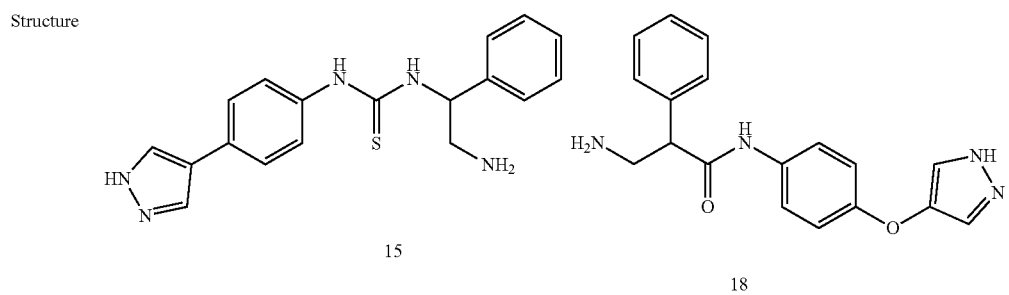 | 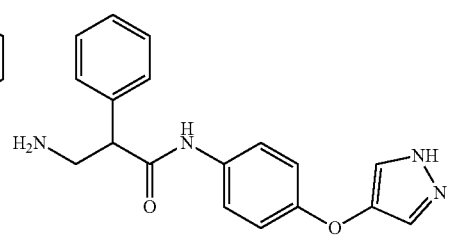 |

| Compound Number | Compound 19 | Compound 20 |
|---|---|---|
| Structure | 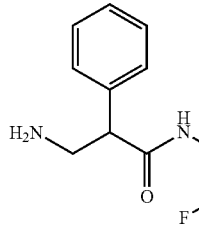 19 | 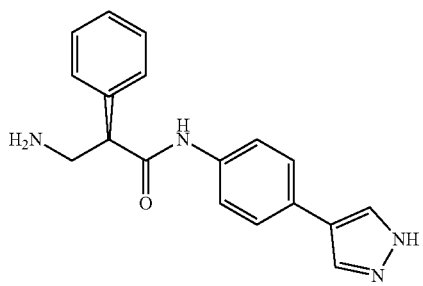 20 |

| Compound Number | Compound 21 |
|---|---|
| Structure | 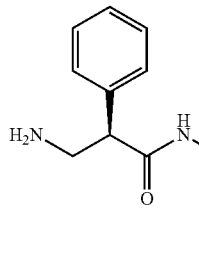 21 |

10. The pharmaceutical composition as claimed in claim 8, further comprising a pharmaceutically acceptable carrier or salt.

11. The pharmaceutical composition as claimed in claim 8, wherein the pharmaceutical composition is used for reducing intraocular pressure.

12. The pharmaceutical composition as claimed in claim 8, wherein the pharmaceutical composition is used for treatment of ocular hypertension or a disease with ocular hypertension.

13. A method for performing an in vivo related application that benefits from the inhibition of a kinase, comprising:
administering the compound represented by Formula (I), Compound 16 or Compound 17, or a pharmaceutically acceptable salt or ester, hydrate, solvate or crystalline form thereof as claimed in claim 1 to a subject in need thereof, wherein the kinase is at least one selected from a group consisting of:

myosin light chain kinase 4;
mitogen-activated protein kinase 19; and
a Rho-associated protein kinase,
wherein the in vivo related application comprises an ophthalmology-related application, and the ophthalmology-related application comprises treatment of high intraocular pressure or glaucoma.

14. The method for performing an in vivo related application that benefits from the inhibition of a kinase as claimed in claim 13, wherein the compound represented by Formula (I), Compound 16 or Compound 17 is present in the form of the individual optical isomers, a mixture of the individual enantiomers or a racemate, and the compound represented by Formula (I) comprises a compound selected from a group consisting of Compound 1 to Compound 15 and Compound 18 to Compound 21 shown in the following:

| Compound Number | Compound 1 | Compound 2 |
|---|---|---|
| Structure | 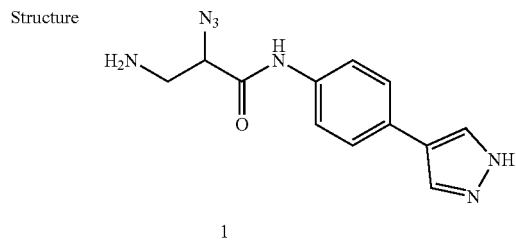 | 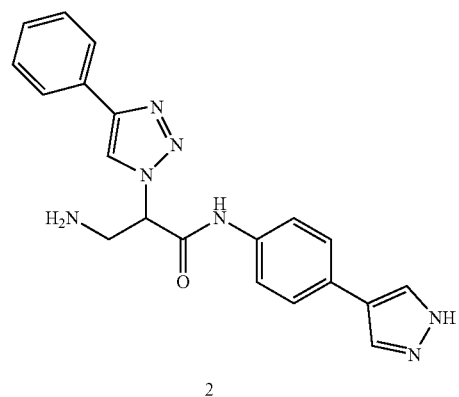 [SMILES: NCC(C(=O)Nc1ccc(-c2cn[nH]c2)cc1)n1cc(-c2ccccc2)nn1] |
| Compound Number | Compound 3 | Compound 4 |
|---|---|---|
| Structure | 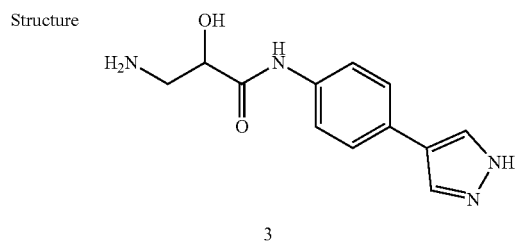 | 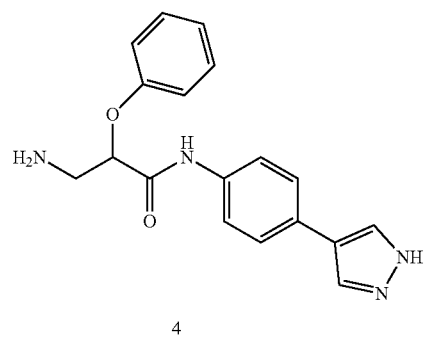 [SMILES: NCC(Oc1ccccc1)C(=O)Nc1ccc(-c2cn[nH]c2)cc1] |
| Compound Number | Compound 5 | Compound 6 |
|---|---|---|
| Structure | 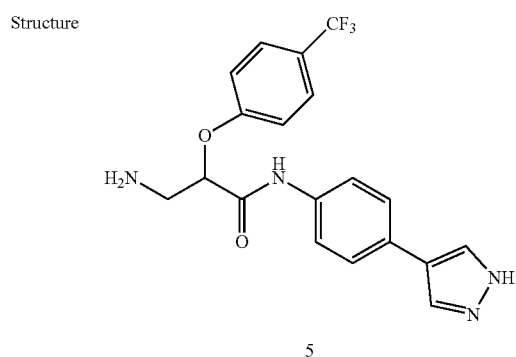 | 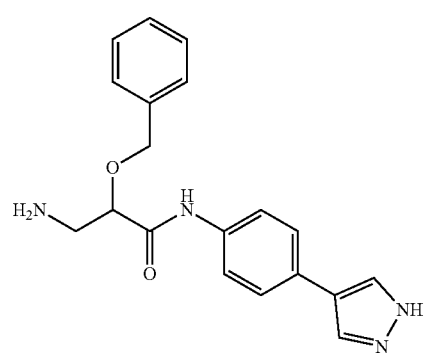 |

-continued
| Compound Number | Compound 7 | Compound 8 |
|---|---|---|
| Structure | 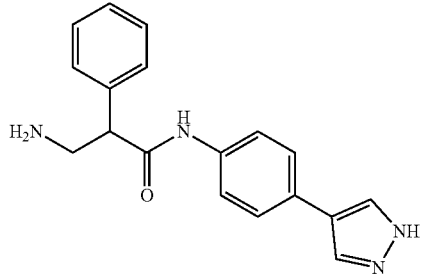 | 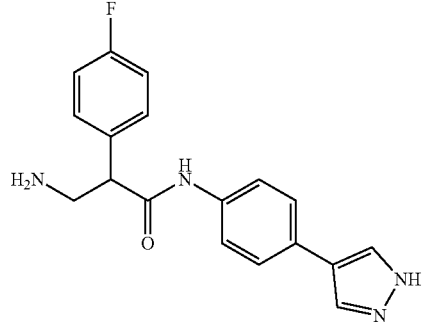 |
| | 7 | 8 |
| Compound Number | Compound 9 | Compound 10 |
|---|---|---|
| Structure | 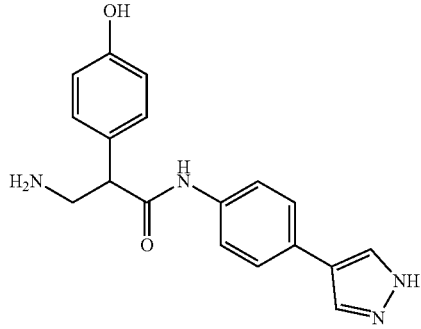 | 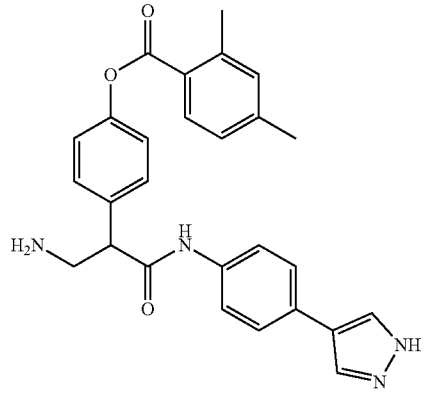 |
| | 9 | 10 |
| Compound Number | Compound 11 | Compound 12 |
|---|---|---|
| Structure | 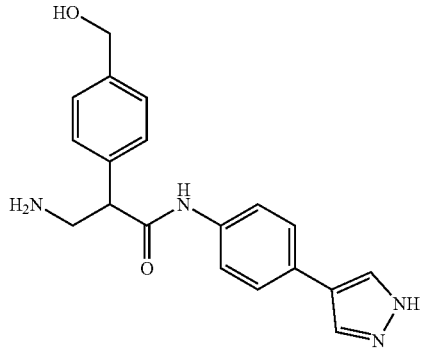 | 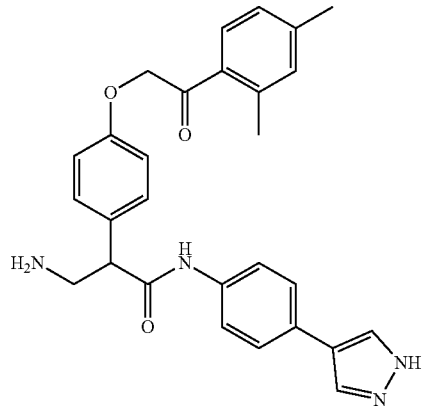 |
| | 11 | 12 |

-continued
| Compound Number | Compound 13 | Compound 14 |
|---|---|---|
| Structure | 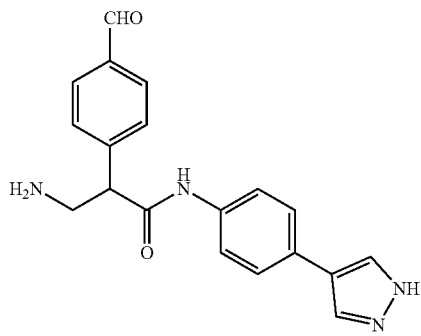 13 | 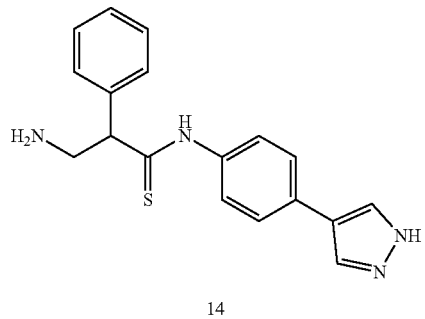 [SMILES: NCC(C(=S)Nc1ccc(-c2cn[nH]c2)cc1)c1ccccc1] 14 |
| Compound Number | Compound 15 | Compound 18 |
|---|---|---|
| Structure | 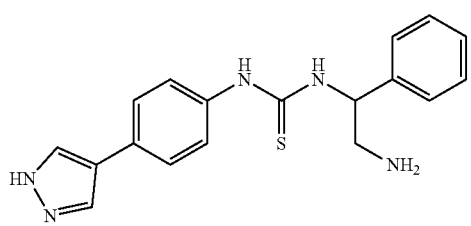 15 | 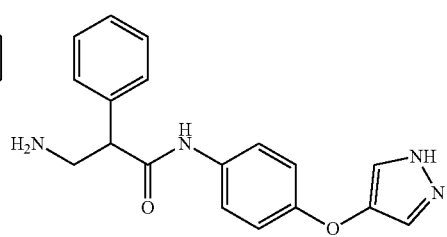 18 |
| Compound Number | Compound 19 | Compound 20 |
|---|---|---|
| Structure | 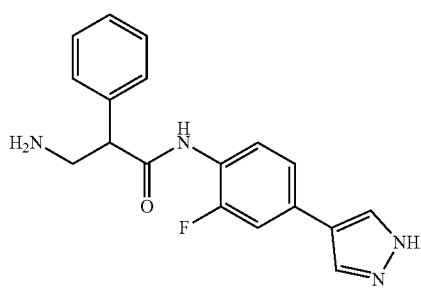 19 | 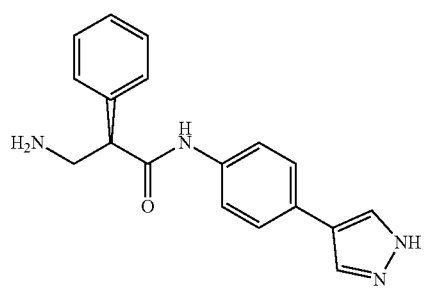 20 |
| Compound Number | Compound 21 |
|---|---|
| Structure | 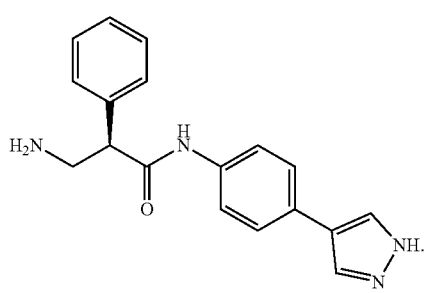 21 |

15. The method for performing an in vivo related application that benefits from the inhibition of a kinase as claimed in claim 13, wherein the ophthalmology-related application is treatment of high intraocular pressure.

16. The method for performing an in vivo related application that benefits from the inhibition of a kinase as claimed in claim 13, wherein the ophthalmology-related application is treatment of glaucoma.

17. The method for performing an in vivo related application that benefits from the inhibition of a kinase as claimed in claim 16, wherein the glaucoma comprises exfoliation glaucoma (XFG).

\* \* \* \* \*